US011446110B2

(12) United States Patent
Rousche et al.

(10) Patent No.: US 11,446,110 B2
(45) Date of Patent: Sep. 20, 2022

(54) NEEDLE SAFETY SYSTEMS

(71) Applicant: Hemotek Medical Incorporated, Healdsburg, CA (US)

(72) Inventors: Patrick Rousche, Healdsburg, CA (US); Peter Tek, Orland Park, IL (US); Charles Ventura, Cary, IL (US); Richard A. Scribner, Shingle Springs, CA (US); Andrew Black, Round Lake, IL (US); Andrew Leopold, Hawthorn Woods, IL (US); Mark Carlson, Fox River Grove, IL (US); Todd Macy, Powell, OH (US); Daniel Lane, Hilliard, OH (US); Adam Hensel, Gahanna, OH (US); Edward Browka, Oneida, NY (US)

(73) Assignee: Hemotek Medical Incorporated, Healdsburg, CA (US)

( * ) Notice: Subject to any disclaimer, the term of this patent is extended or adjusted under 35 U.S.C. 154(b) by 387 days.

(21) Appl. No.: 16/447,139

(22) Filed: Jun. 20, 2019

(65) Prior Publication Data
US 2020/0008898 A1 Jan. 9, 2020

Related U.S. Application Data

(63) Continuation of application No. PCT/US2017/068021, filed on Dec. 21, 2017.
(Continued)

(51) Int. Cl.
*A61B 90/00* (2016.01)
*A61B 5/15* (2006.01)
(Continued)

(52) U.S. Cl.
CPC ............ *A61B 90/03* (2016.02); *A61B 5/1422* (2013.01); *A61M 5/158* (2013.01);
(Continued)

(58) Field of Classification Search
CPC .............. A61M 5/158; A61M 5/16813; A61M 39/281; A61M 2005/1586; A61M 39/284;
(Continued)

(56) References Cited

U.S. PATENT DOCUMENTS 4,407,434 A 10/1983 Kempf
4,551,128 A 11/1985 Hakim et al.
(Continued)

FOREIGN PATENT DOCUMENTS

CN 101730555 A 6/2010
FR 1426230 * 1/1966 .......... A61M 1/7413
(Continued)

*Primary Examiner* — Theodore J Stigell
*Assistant Examiner* — Rachel T. Smith
(74) *Attorney, Agent, or Firm* — Levine Bagade Han LLP

(57) ABSTRACT

Tissue access devices and methods of using the same are disclosed. The devices can have a sensor configured to occlude a flow path by deflecting a membrane into the flow path when the devices become dislodged from tissue. The sensor can be configured to partially or fully occlude the flow path. The sensor can have a spring. The spring can be biased to move the sensor from a sensor first configuration to a sensor second configuration when a force applied by the sensor first surface against a non-sensor surface changes from a first force to a second force less than the first force. The membrane can be deflected into the flow path when the sensor is in the sensor second configuration.

17 Claims, 71 Drawing Sheets

Related U.S. Application Data

(60) Provisional application No. 62/579,129, filed on Oct. 30, 2017, provisional application No. 62/576,752, filed on Oct. 25, 2017, provisional application No. 62/504,713, filed on May 11, 2017, provisional application No. 62/458,041, filed on Feb. 13, 2017, provisional application No. 62/437,096, filed on Dec. 21, 2016.

(51) Int. Cl.
  *A61M 5/158* (2006.01)
  *A61M 5/168* (2006.01)

(52) U.S. Cl.
  CPC ... *A61M 5/16813* (2013.01); *A61B 2090/036* (2016.02); *A61M 2005/1586* (2013.01); *A61M 2005/1588* (2013.01)

(58) Field of Classification Search
  CPC ........ A61M 2039/1005; A61M 1/3656; A61M 39/26; A61M 2005/13; A61B 5/1422
  See application file for complete search history.

(56) References Cited

U.S. PATENT DOCUMENTS

| | | |
|---|---|---|
| 4,960,259 A | 10/1990 | Sunnanvader et al. |
| 5,108,374 A | 4/1992 | Lemieux |
| 5,300,043 A | 4/1994 | Devlin et al. |
| 5,522,806 A | 6/1996 | Schonbachler et al. |
| 6,126,637 A | 10/2000 | Kriesel et al. |
| 7,044,936 B2 | 5/2006 | Harding et al. |
| 8,313,497 B2 | 11/2012 | Walberg et al. |
| 8,926,571 B1 | 1/2015 | Keith |
| 10,213,548 B2 | 2/2019 | Rousche et al. |
| 10,994,075 B2 | 5/2021 | Rousche et al. |
| 2001/0003158 A1 | 6/2001 | Kensey et al. |
| 2008/0281276 A1 | 11/2008 | Shekalim |
| 2008/0312666 A1 | 12/2008 | Ellingwood et al. |
| 2009/0069844 A1 | 3/2009 | Green et al. |
| 2013/0218073 A1 | 8/2013 | Ekdahl et al. |
| 2016/0175563 A1 | 6/2016 | Woehr et al. |
| 2017/0021098 A1 | 1/2017 | Rousche et al. |
| 2019/0143033 A1 | 5/2019 | Rousche et al. |
| 2021/0046241 A1 | 2/2021 | Rousche et al. |
| 2021/0228802 A1* | 7/2021 | Rousche ............. A61M 39/281 |

FOREIGN PATENT DOCUMENTS

| | | |
|---|---|---|
| JP | 2006-000646 | 1/2006 |
| JP | 2010-526578 | 8/2010 |
| WO | WO 1993/024173 | 12/1993 |
| WO | WO 1995/015779 | 6/1995 |
| WO | WO 2015/156850 | 10/2015 |
| WO | WO 2018/119309 | 6/2018 |
| WO | WO 2019/213598 | 11/2019 |

\* cited by examiner

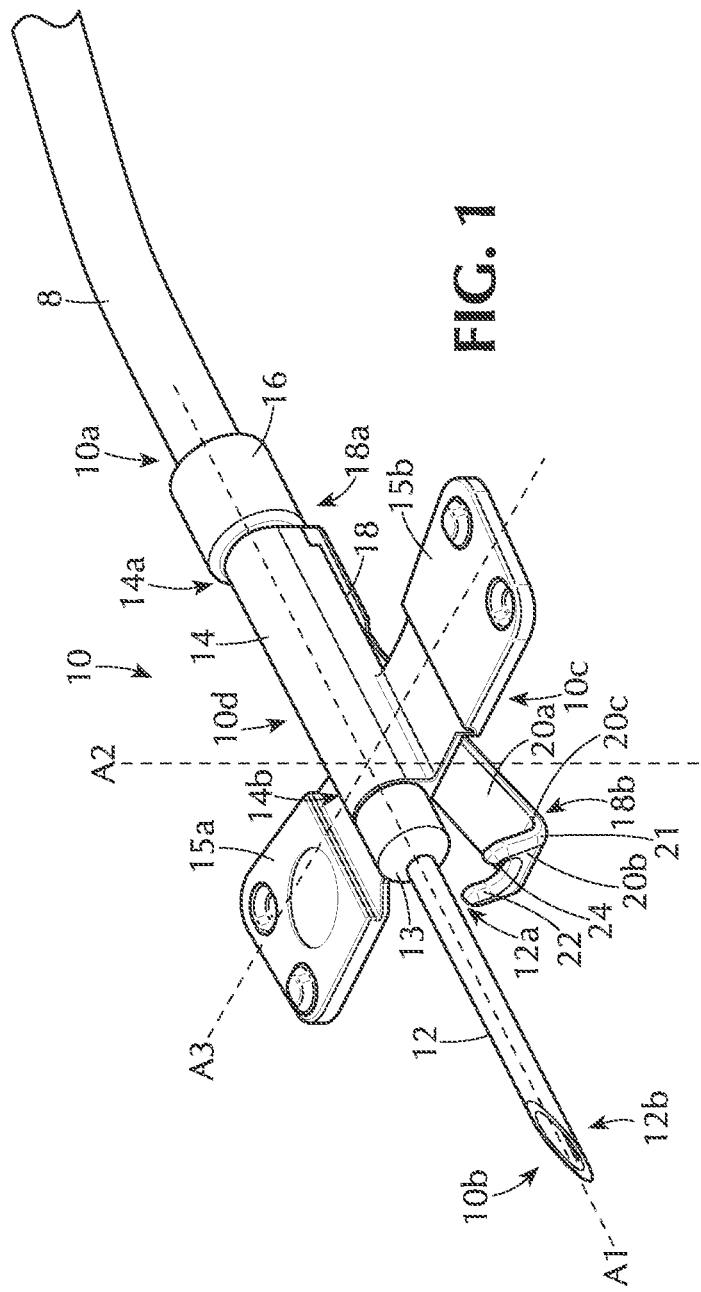

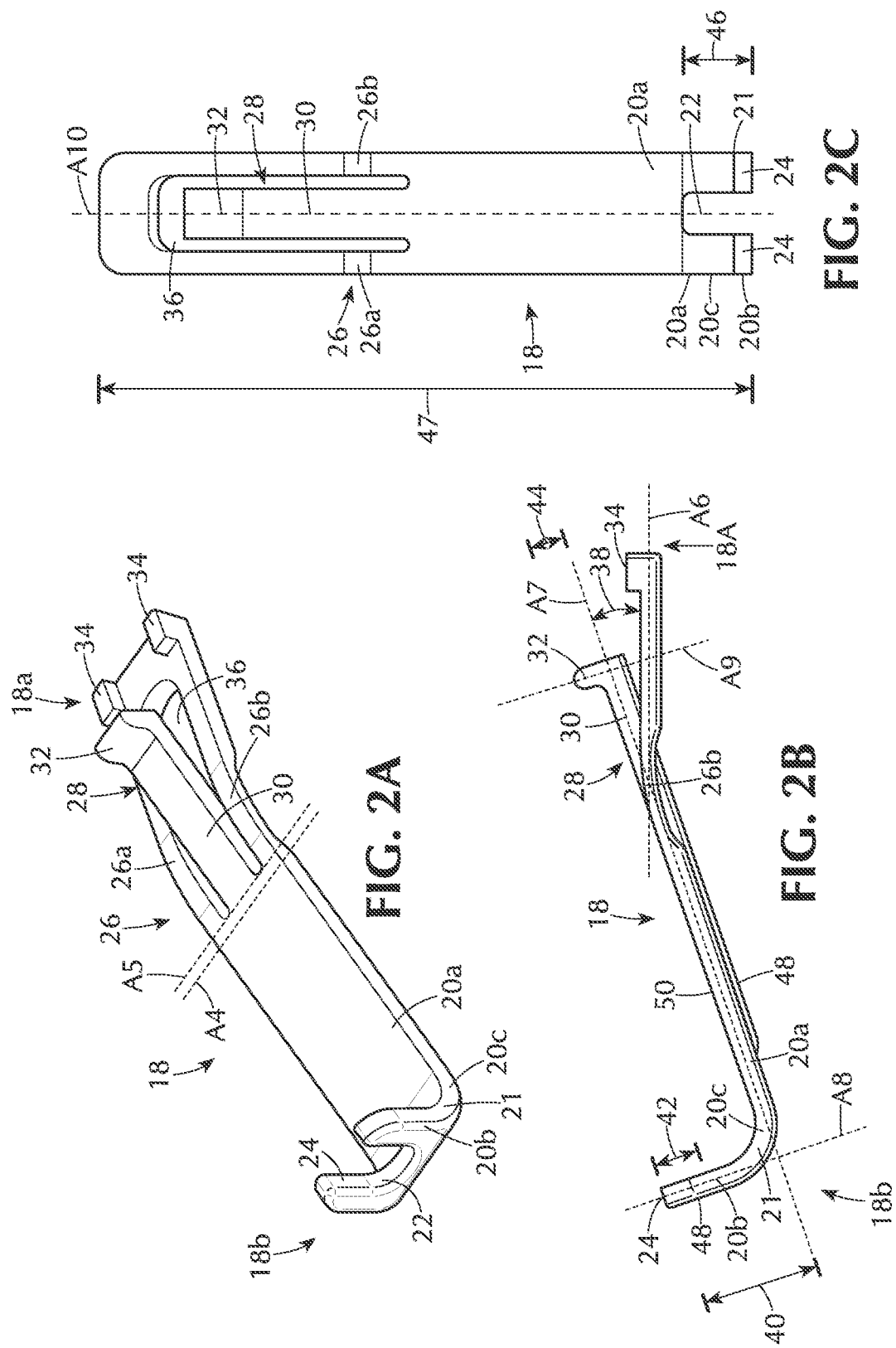

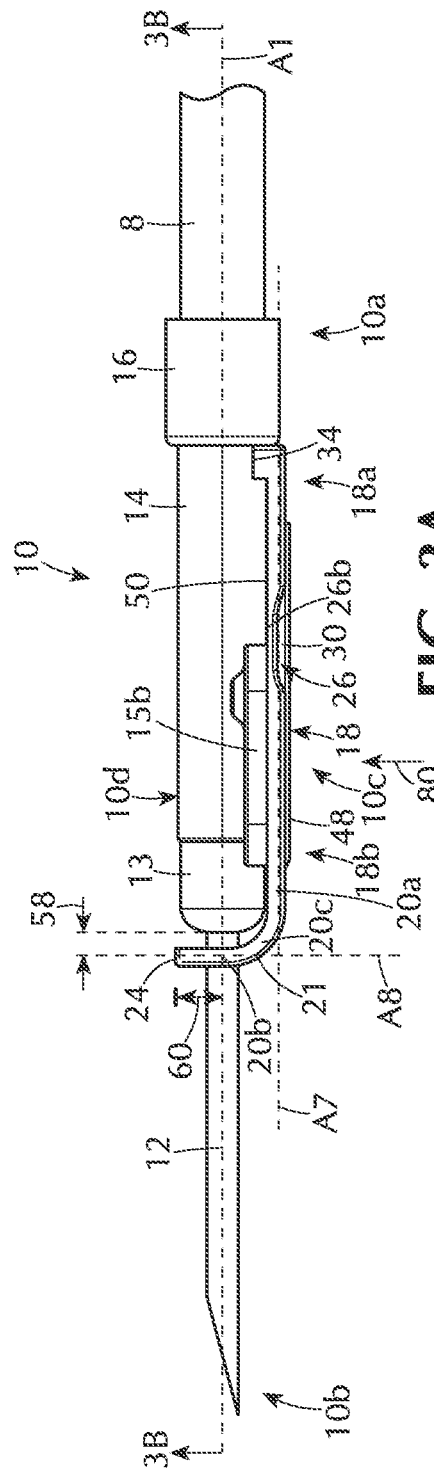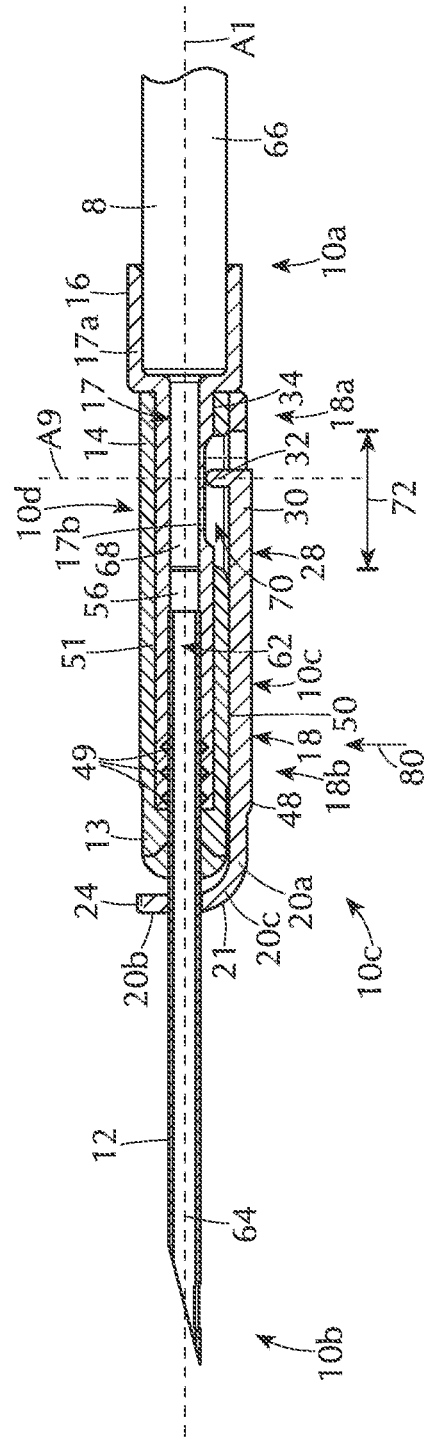

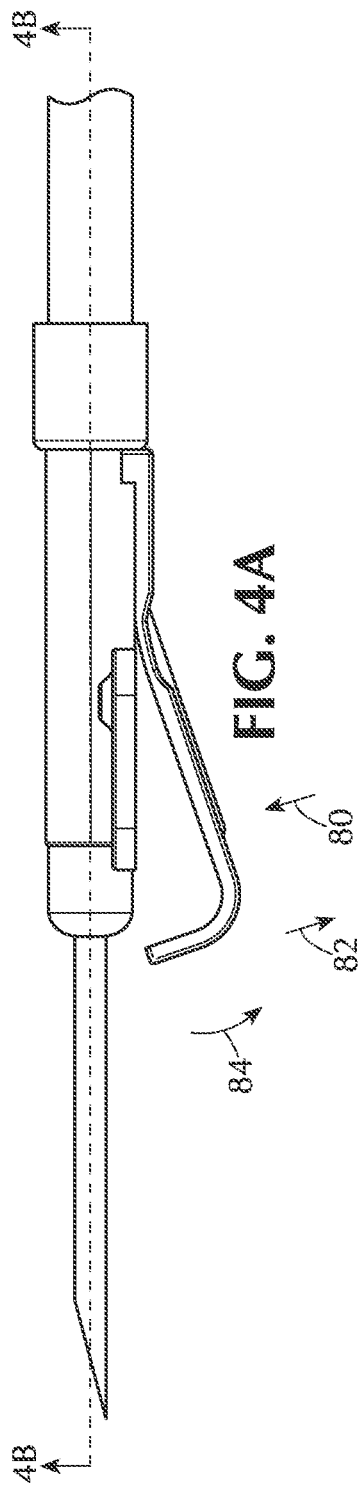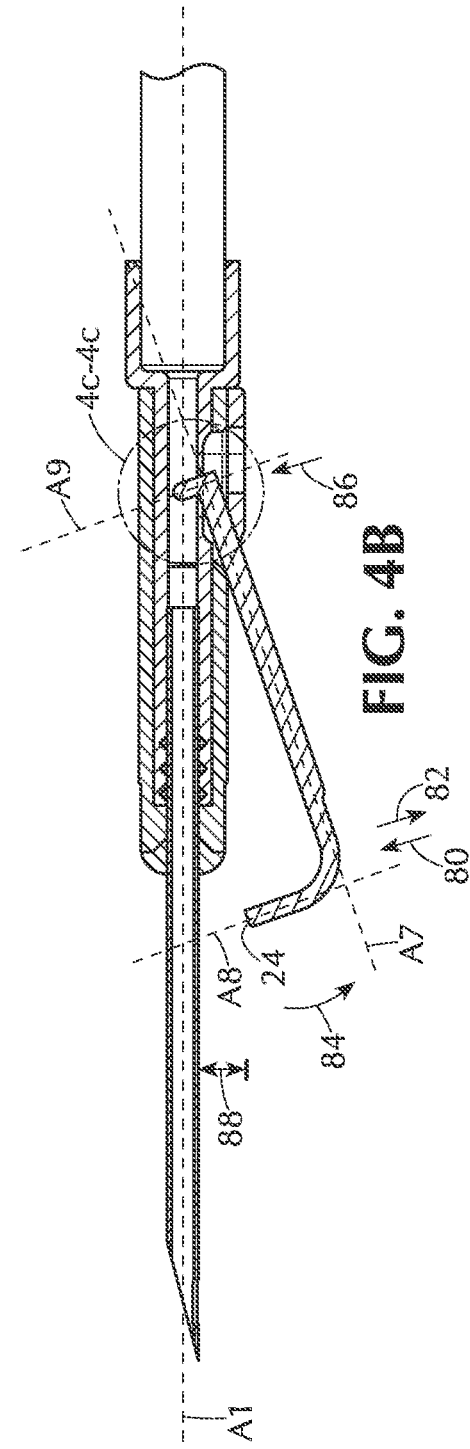

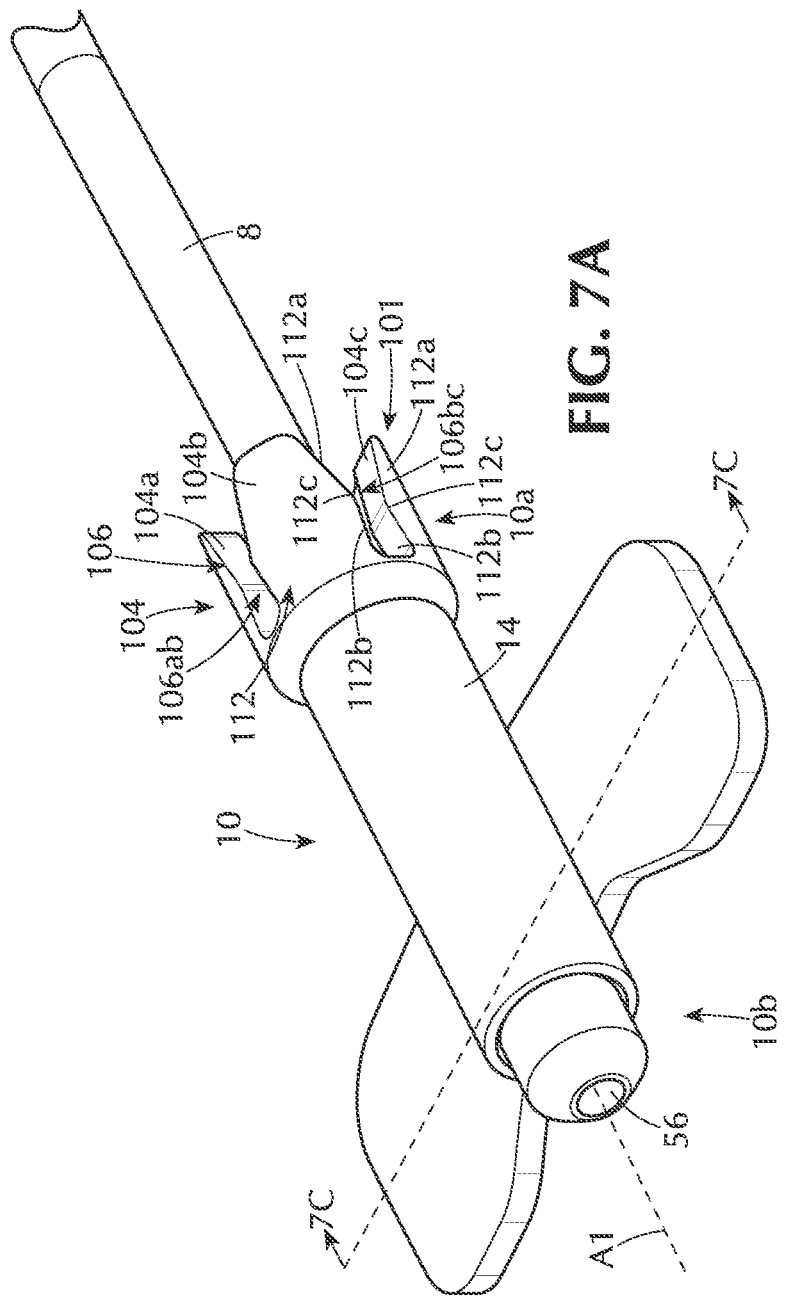

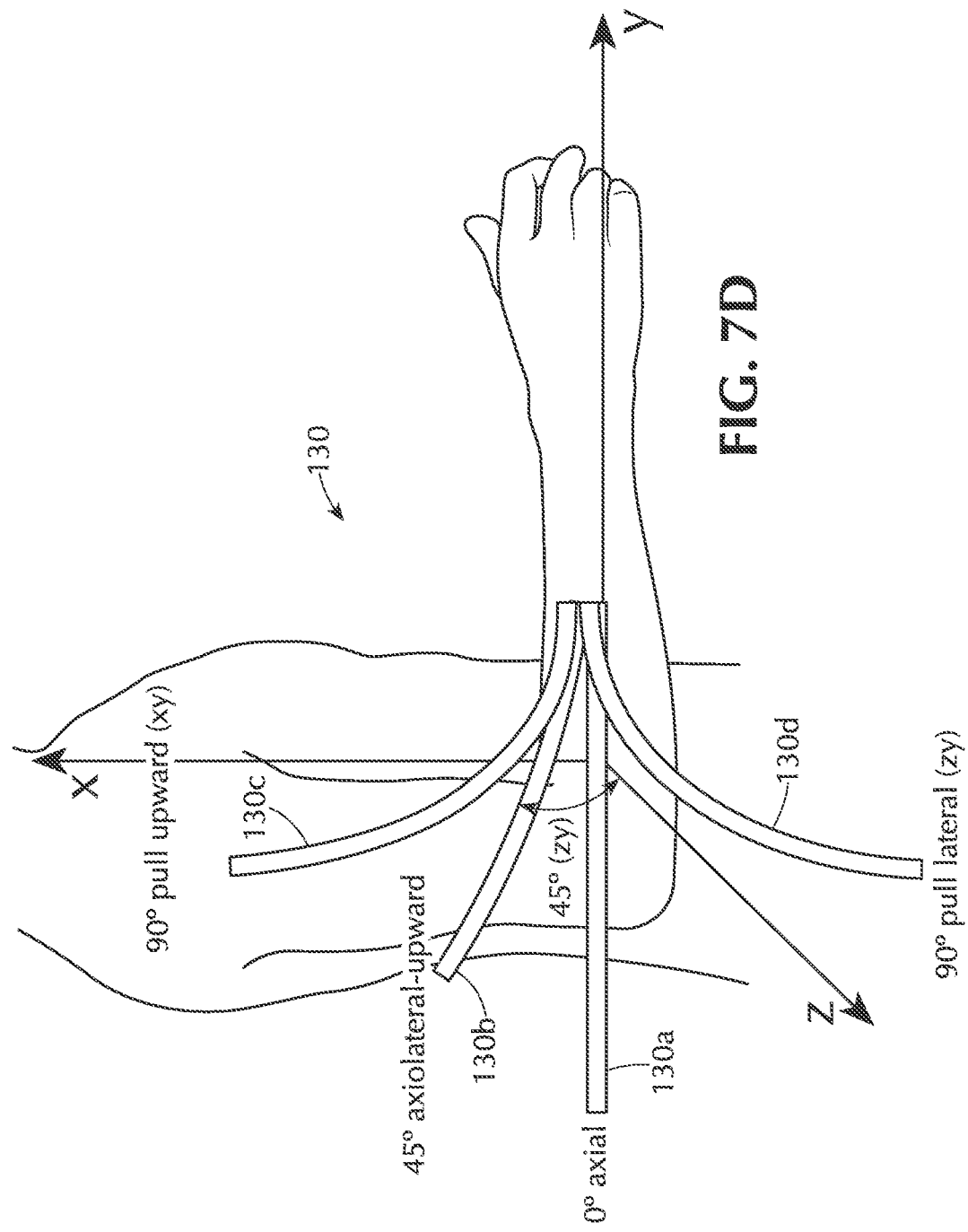

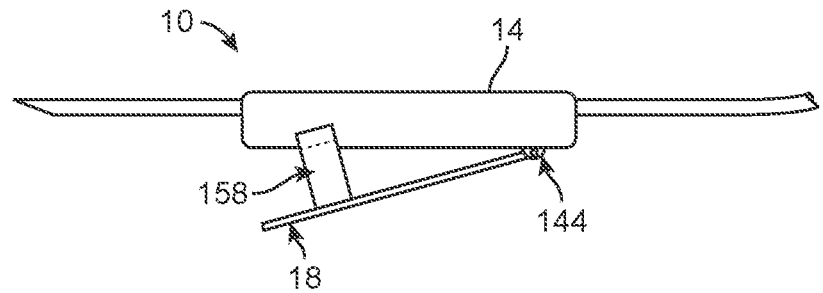
FIG. 13A
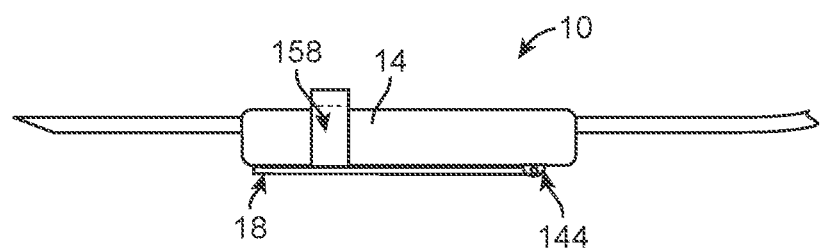
FIG. 13B
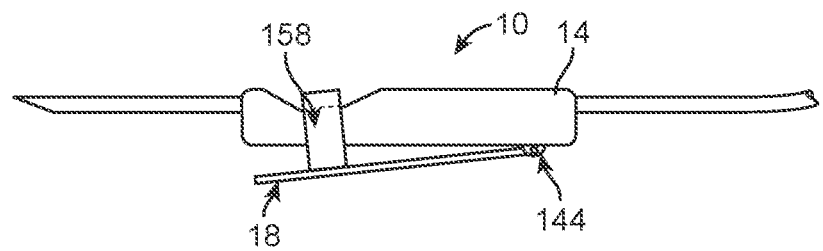
FIG. 13C
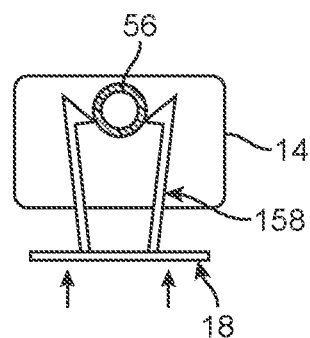 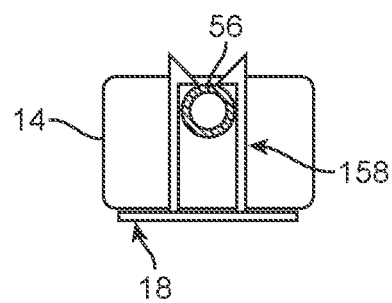
FIG. 13D          FIG. 13E

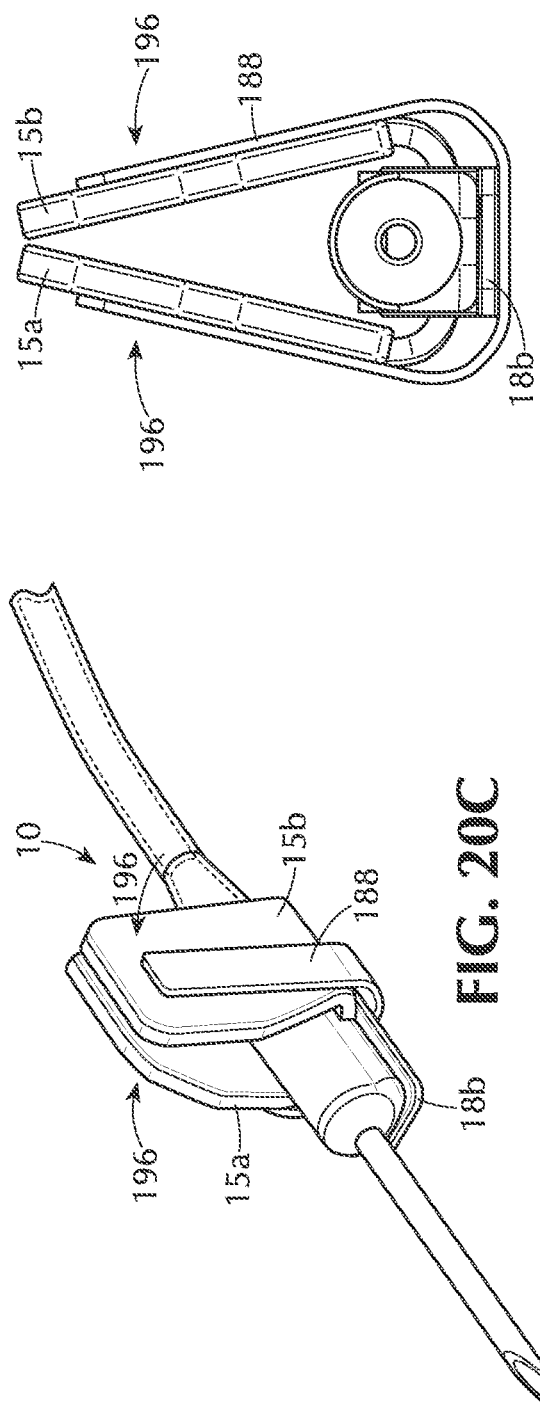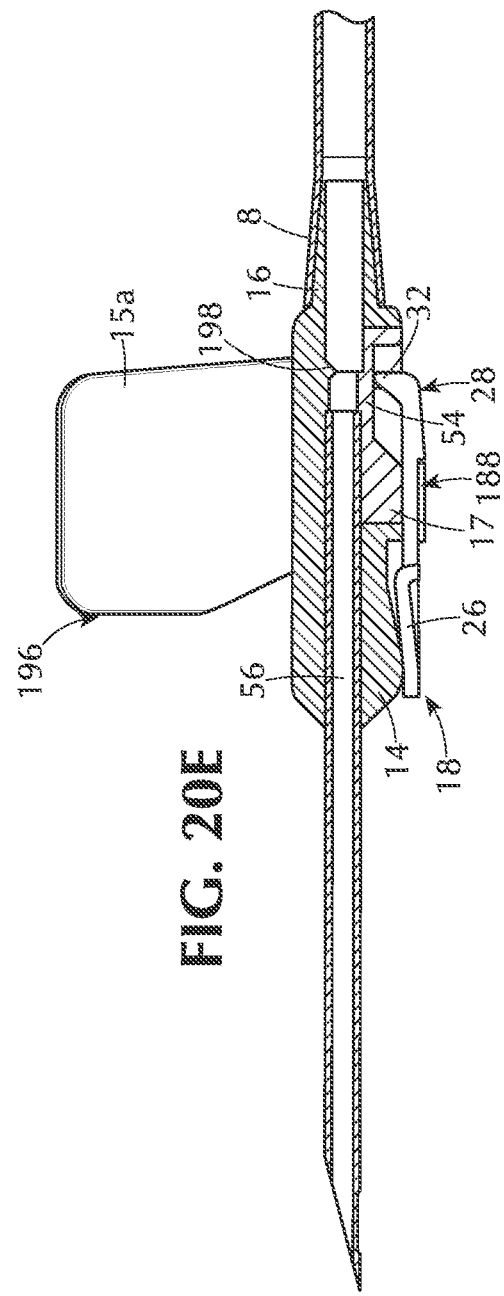

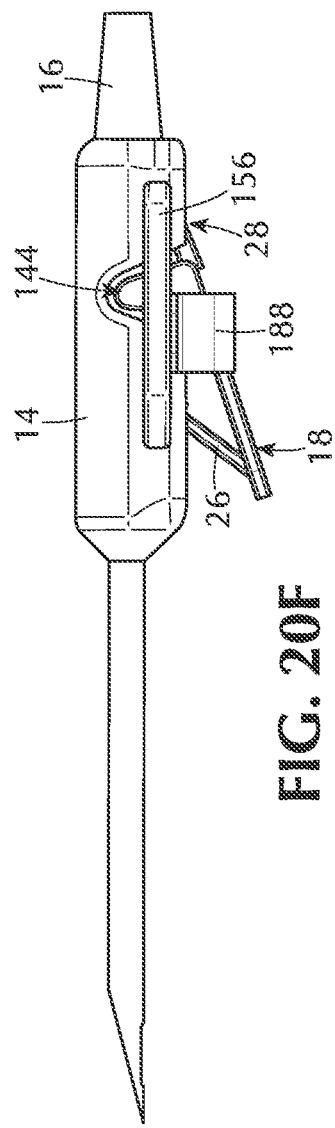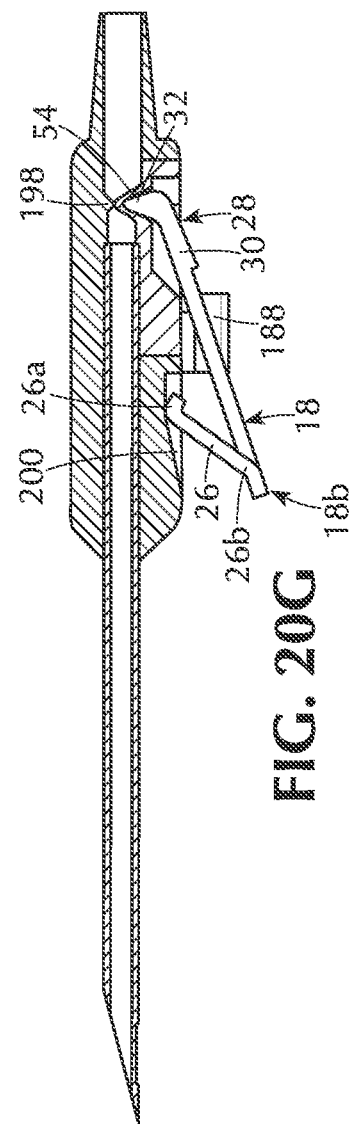
FIG. 20F
FIG. 20G

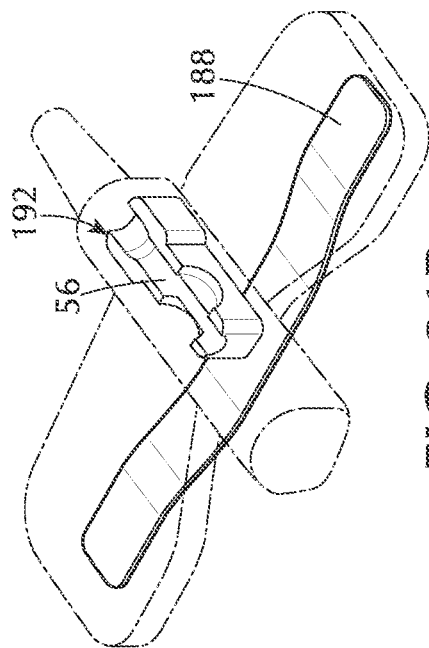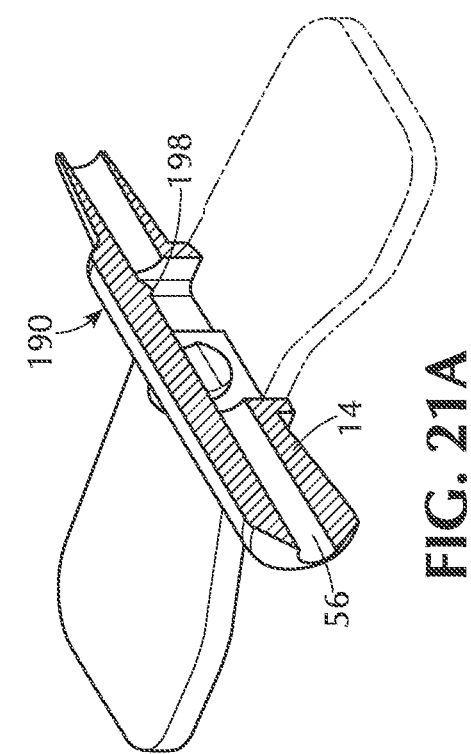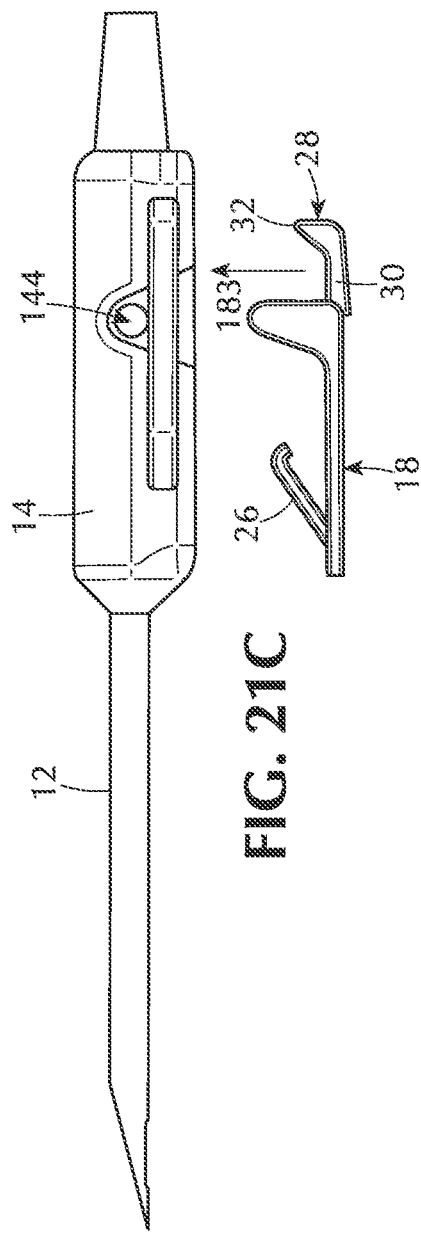
FIG. 21B
FIG. 21A
FIG. 21C

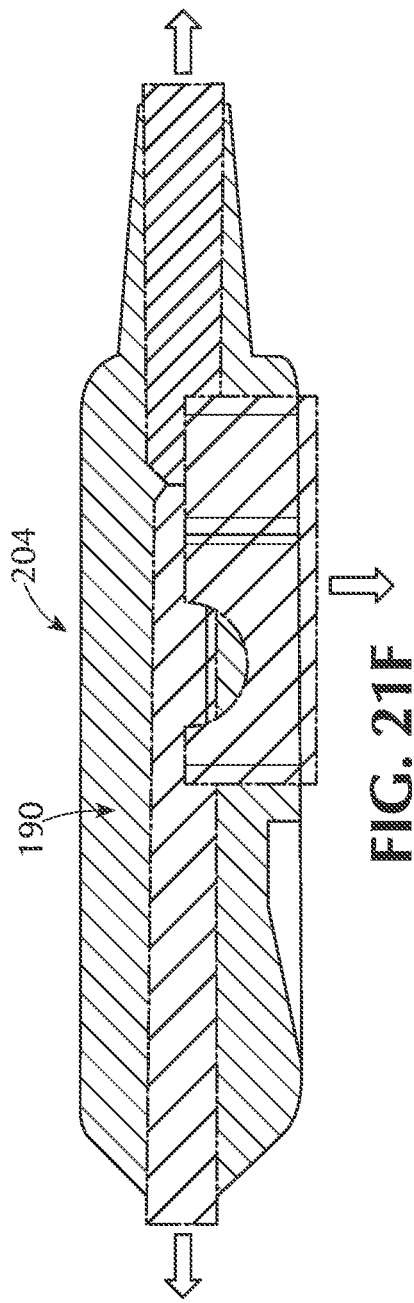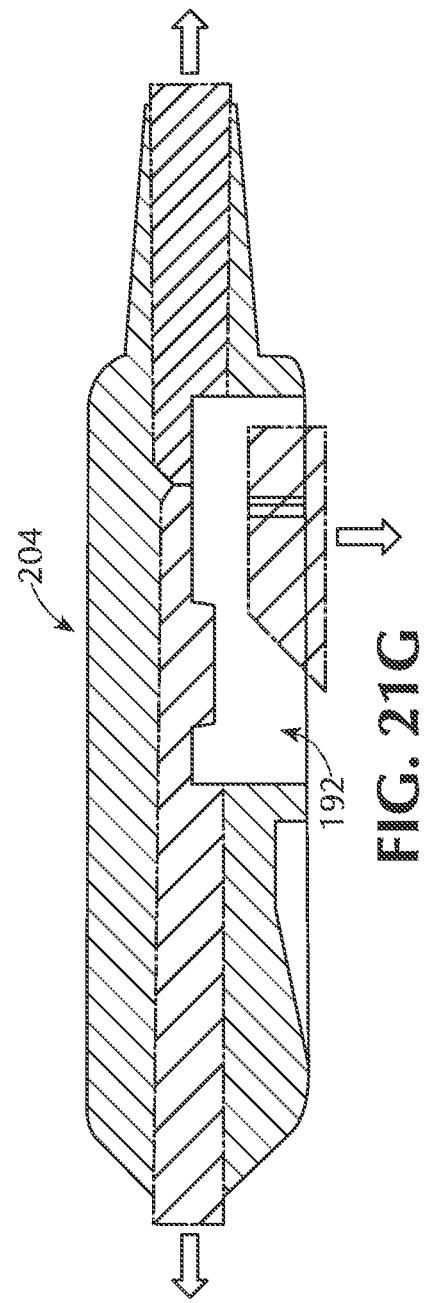

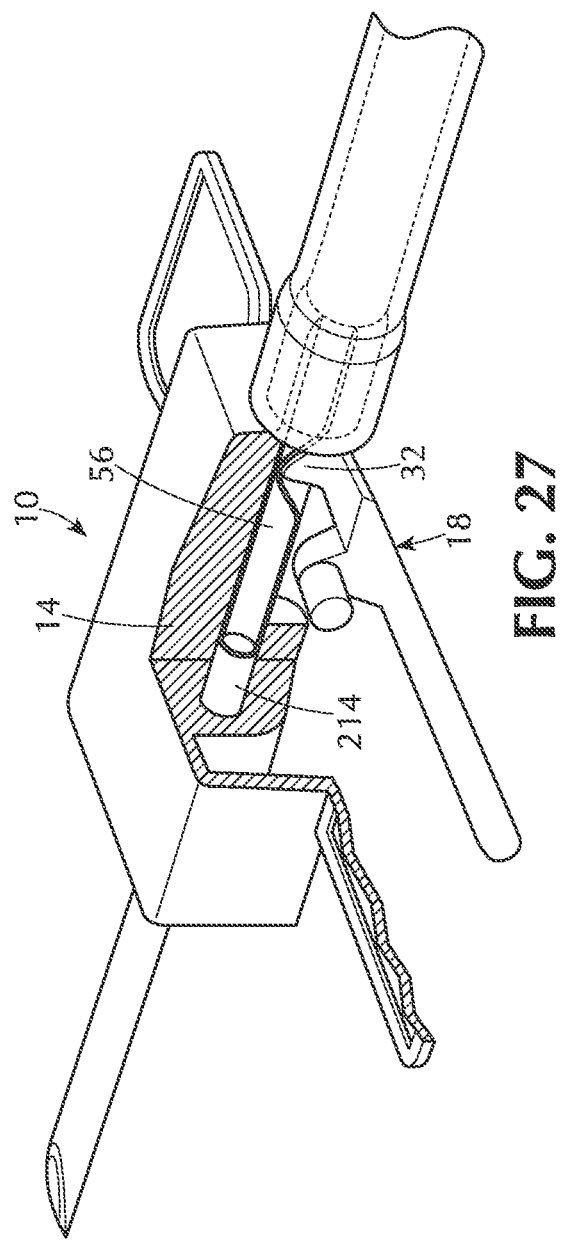

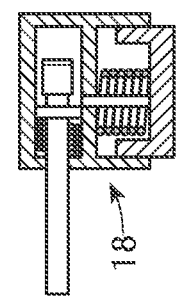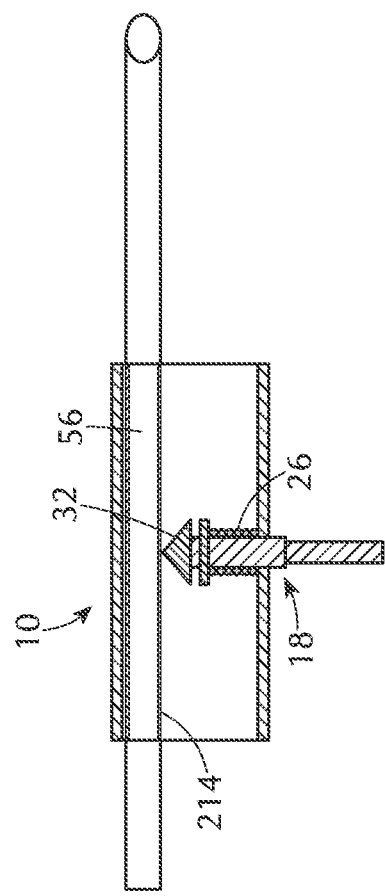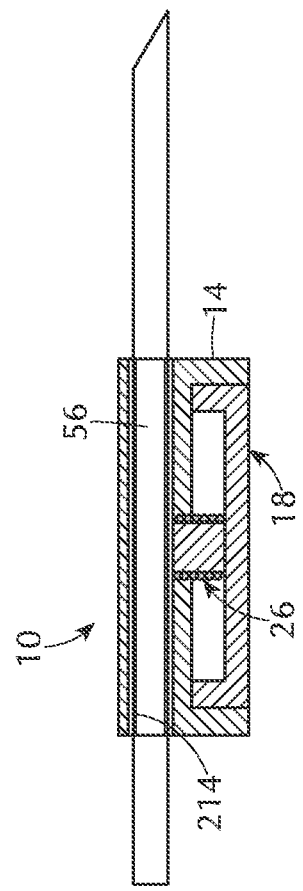

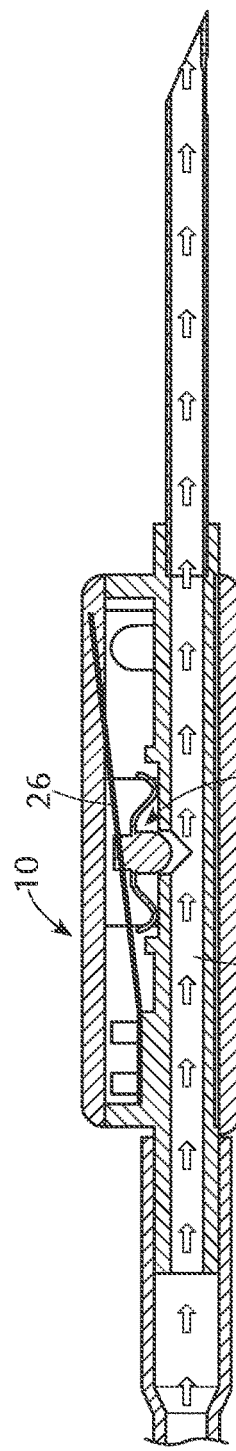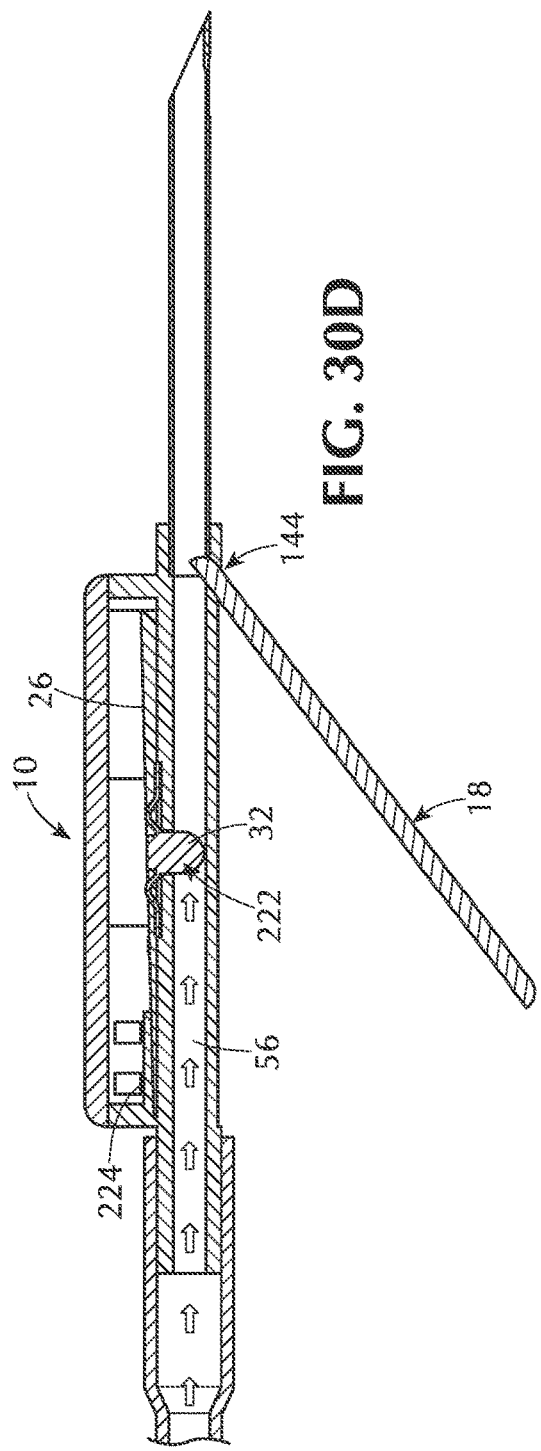

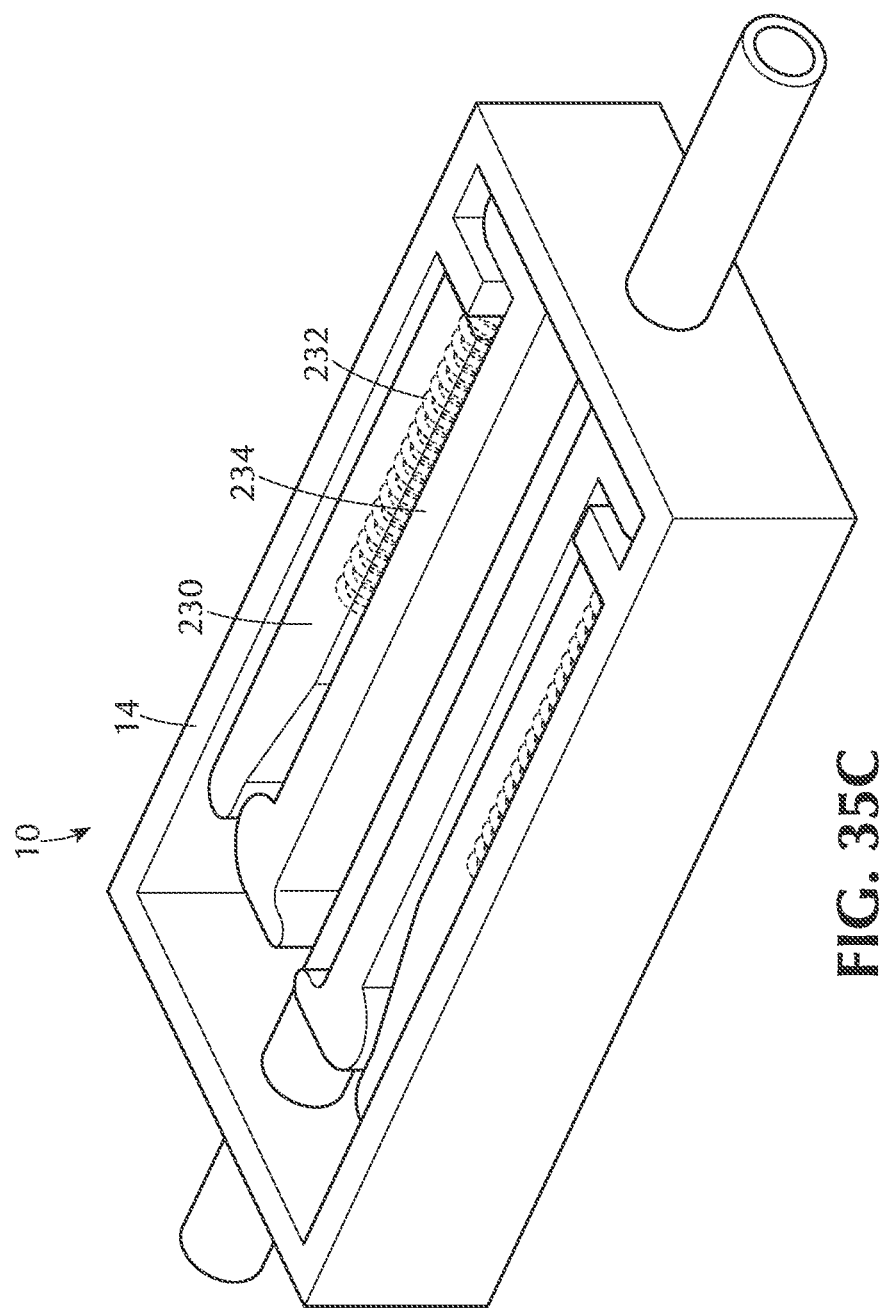

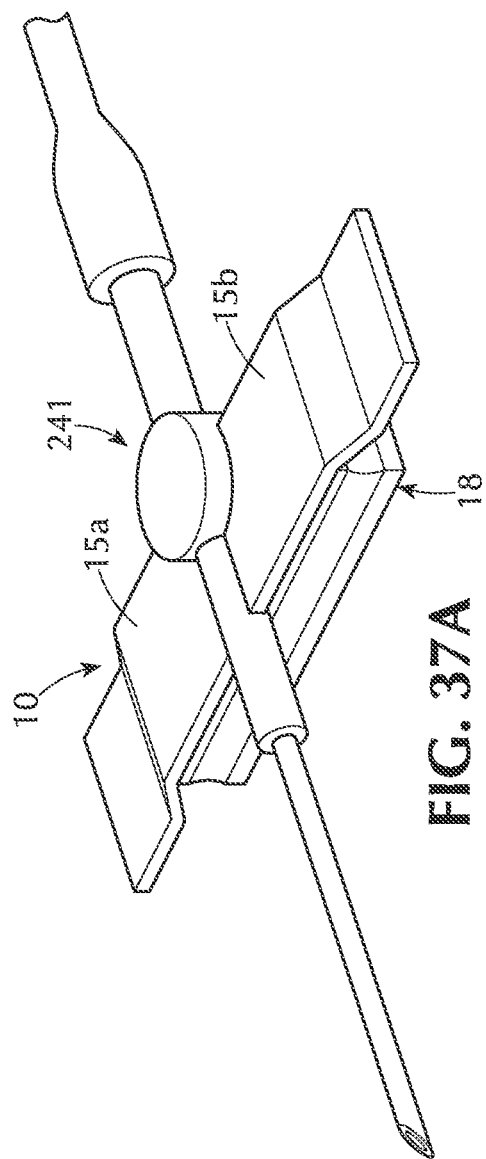
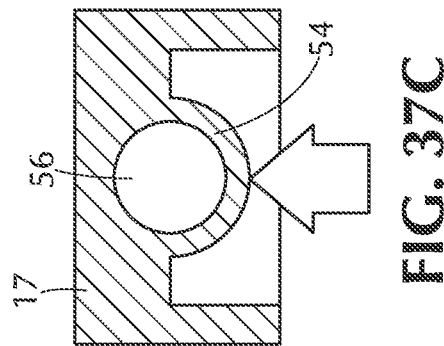
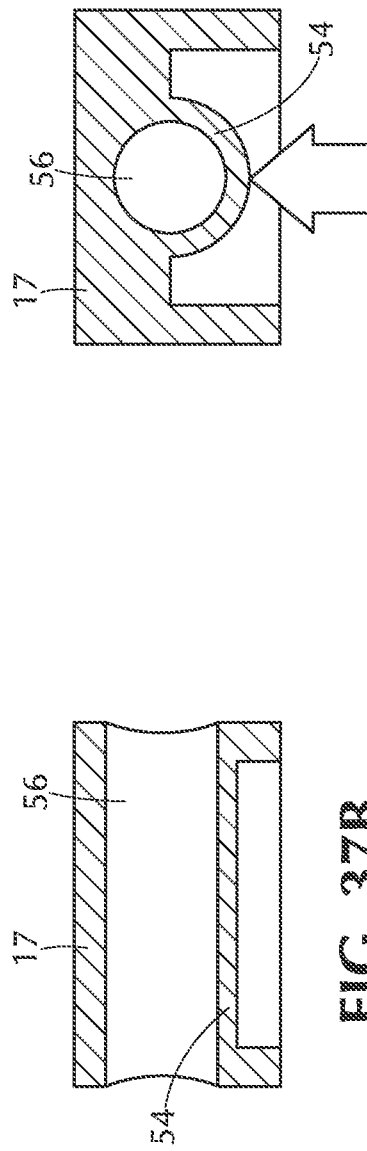
FIG. 37A
FIG. 37B
FIG. 37C

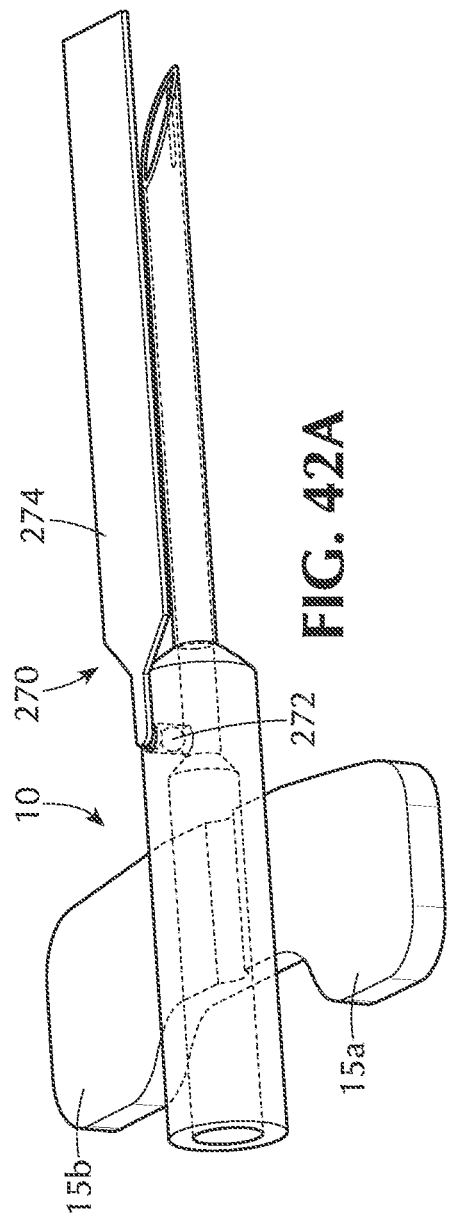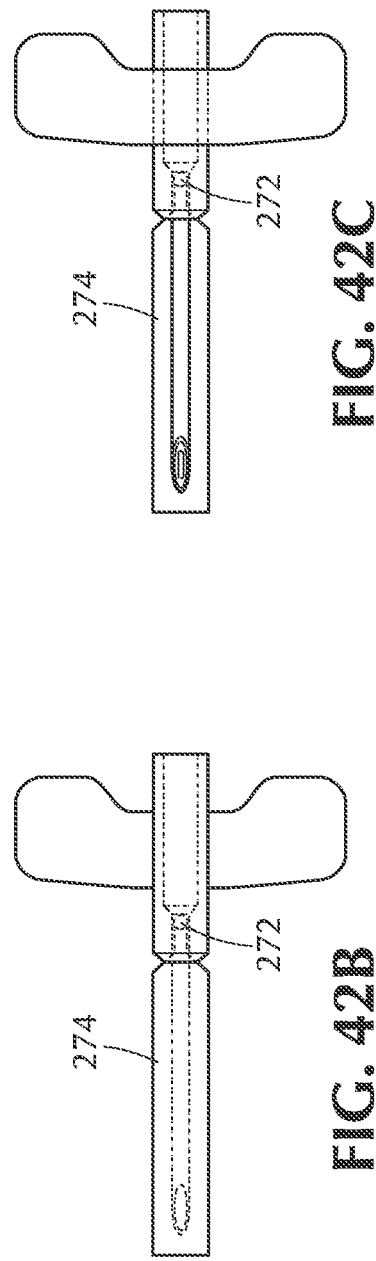

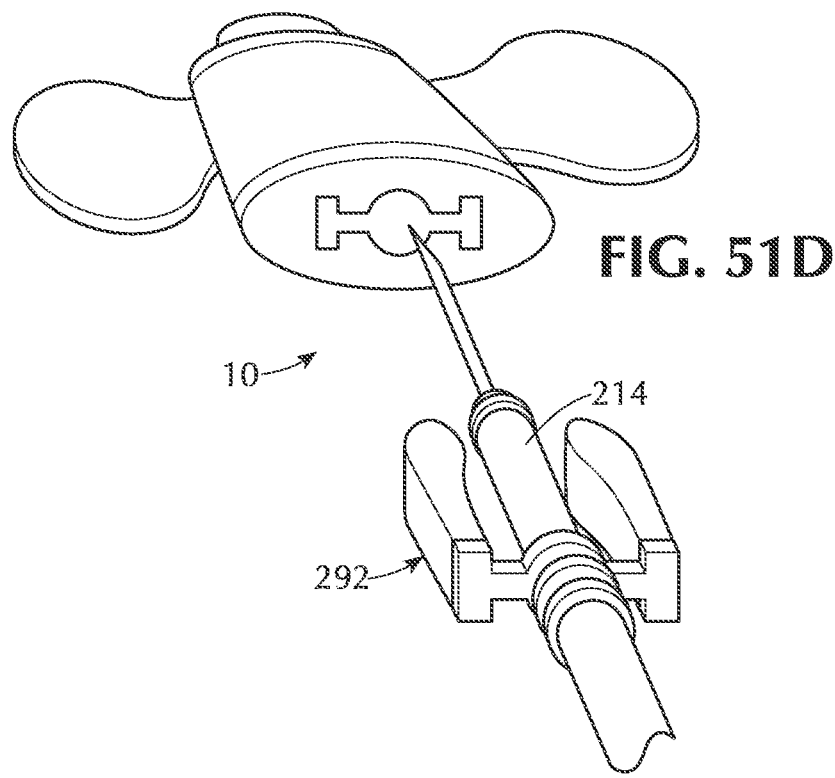
FIG. 51D
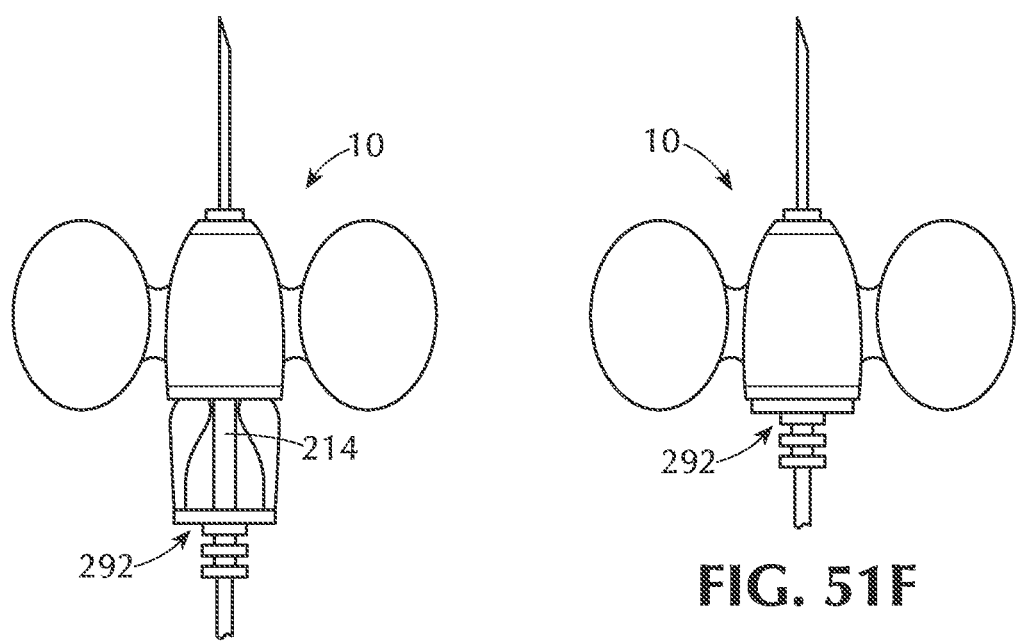
FIG. 51E  FIG. 51F

NEEDLE SAFETY SYSTEMS

CROSS-REFERENCE TO RELATED APPLICATIONS

This application is a continuation of International Application No. PCT/US2017/068021, filed Dec. 21, 2017, which claims priority to U.S. Provisional Application No. 62/437,096 filed Dec. 21, 2016 titled Needle Safety Systems, U.S. Provisional Application No. 62/458,041 filed Feb. 13, 2017 titled Needle Safety Systems II, U.S. Provisional Application No. 62/504,713 filed May 11, 2017 titled Needle Safety Systems III, U.S. Provisional Application No. 62/576,752 filed Oct. 25, 2017 titled Needle Safety Systems IV, and U.S. Provisional Application No. 62/579,129 filed Oct. 30, 2017 titled Needle Safety Systems V. Each of these applications is incorporated herein by reference in its entirety for all purposes.

BACKGROUND

1. Technical Field

Tissue access devices and methods of using the same are disclosed. More specifically, tissue access devices that can automatically occlude flow when dislodged from tissue and methods of using the same are disclosed.

2. Background of the Art

There are a number of techniques that can detect an errant flow of fluid through a vascular connection leading fluid from the outside of the body to the inside of the body. Common to many of these is the use of a 'continuity sensor' that looks for an interruption of energy-based signal or some mechanical connection from the tubing to the body. Such systems often use mechanical connectors, a small electrical current, a capacitance, a magnet or even ultrasound as a means of monitoring the fidelity of the connection between the body and the fluid passing element. Others use techniques designed to look for 'wetness' on the theory that a dislodged needle will leak fluid and fluid detection can be used as a surrogate marker for needle dislodgement.

Accordingly, a need exists to identify if there is a state whereby errant flow from a dislodged needle is present with a simple mechanical based system that 'detects' presence of the needle on the skin and therefore can be used to determine if the needle is or is not inserted into the patient during the fluid delivery process. A need also exists to prevent needle dislodgement from external forces pulling on the tube connected to the needle before the needle is dislodged.

BRIEF SUMMARY

This disclosure relates generally to tissue access devices and vascular connections.

More specifically, tissue access devices that can automatically occlude flow when dislodged from tissue and methods of using the same are disclosed. By blocking fluid flow after a tissue access device becomes dislodged, errant fluid flow during medical therapy can be reduced or prevented, providing essential safety to the patient. Tissue access devices that can prevent dislodgement and methods of using the same are also disclosed. By blocking fluid flow before a tissue access device becomes dislodged, errant fluid flow during medical therapy can be avoided altogether, providing essential safety to the patient.

Tissue access devices are disclosed. For example, a vessel access device is disclosed having a device longitudinal axis. The device can have a needle having a needle proximal end and a needle distal end. The device can have a housing having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The movable footplate can have a footplate first configuration when the footplate first surface applies a first force to a non-footplate surface and a footplate second configuration when the footplate first surface applies a second force less than the first force to the non-footplate surface. The spring can be biased to move the movable footplate from the footplate first configuration to the footplate second configuration when the first force decreases to the second force. At least a first portion of the occluder can occlude the housing conduit when the movable footplate is in the footplate second configuration. At least a second portion of the occluder can be in the housing opening when the movable footplate is in the footplate second configuration and outside the housing opening when the movable footplate is in the footplate first configuration.

Tissue access devices are disclosed. For example, a tissue access device is disclosed having a device longitudinal axis. The device can have a needle having a needle proximal end and a needle distal end. The device can have a housing having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The spring can be biased to move the movable footplate from a footplate first configuration to a footplate second configuration when a force applied by the footplate first surface against a non-footplate surface changes from a first force to a second force less than the first force. At least a first portion of the occluder can occlude the housing conduit when the movable footplate is in the footplate second configuration. The footplate distal end can have a barrier configured to prevent over insertion of the needle into a vessel. At least a portion of the barrier can be closer to the needle when the movable footplate is in the footplate first configuration than when the movable footplate is in the footplate second configuration.

Tissue access devices are disclosed. For example, a vessel access device is disclosed having a device longitudinal axis. The device can have a needle having a needle proximal end and a needle distal end. The device can have a housing having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The spring can be biased to move the movable footplate from a footplate first configuration to a footplate second configuration when a force applied by the footplate first surface against a non-footplate surface changes from a first force to a second force less than the first force. At least a first portion of the occluder can occlude the housing conduit when the movable footplate is in the footplate second configuration. The footplate distal end can have a curved surface configured to reduce friction against the non-footplate surface when the needle is inserted into a vessel. At least a portion of the curved surface can be closer to the needle when the movable footplate is in the footplate first configuration than when the movable footplate is in the footplate second configuration.

BRIEF DESCRIPTION OF THE DRAWINGS

The drawings shown and described are exemplary embodiments and non-limiting. Like reference numerals indicate identical or functionally equivalent features throughout.

FIG. 1 illustrates a perspective view of a variation of a tissue access device in an occluded configuration having a sensor.

FIG. 2A illustrates a perspective view of the sensor of FIG. 1.

FIG. 2B illustrates a side view of the sensor of FIG. 2A.

FIG. 2C illustrates a top view of the sensor of FIG. 2A.

FIG. 3A illustrates a side view of the tissue access device of FIG. 1 in a less occluded configuration.

FIG. 3B illustrates a variation of a longitudinal cross-sectional view of the tissue access device of FIG. 3A taken along line 3B-3B.

FIG. 4A illustrates a side view of the tissue access device of FIG. 1.

FIG. 4B illustrates a side view of the tissue access device of FIG. 4A taken along line 4B-4B.

FIG. 7A illustrates a perspective view of a variation of a tissue access device having a pincher system.

FIG. 7D illustrates a variation of a force classification scheme.

FIGS. 13A-13E illustrate a variation of a flow control mechanism.

FIGS. 20A-20I illustrate a variation of a tissue access device having a strap.

FIGS. 21A-21I illustrate a variation of a tissue access device manufacturing process and variations of the components thereof.

FIG. 27 illustrates a variation of a flow restrictor.

FIGS. 28A-28F illustrate a variation of a flow restrictor.

FIGS. 30A-30D illustrate a variation of a flow restrictor.

FIGS. 35A-35C illustrate a variation of a flow restrictor.

FIGS. 37A-37C illustrate a variation of an insert.

FIGS. 42A-42E illustrate a variation of a wetness detection system.

FIGS. 51A-51F illustrate a variation a flow control system.

DETAILED DESCRIPTION

Figure 4C:
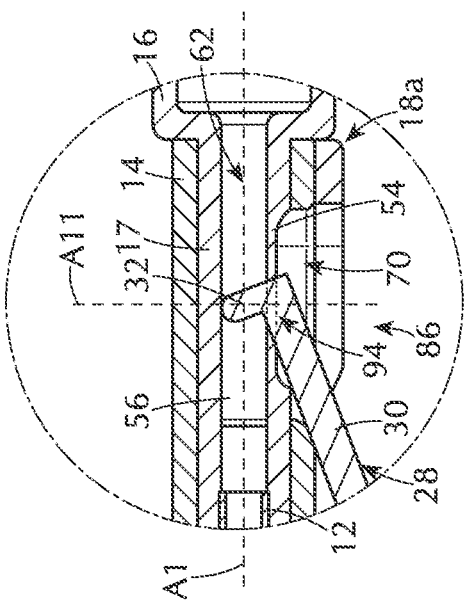
FIG. 4C is a magnified view of the tissue access device of FIG. 4B at section 4C-4C.

Tissue access devices (also referred to as fluid access devices, vessel access devices, blood access devices, and needles) are disclosed. The tissue access devices disclosed can withdraw and/or deliver fluid directly into a patient. In hemodialysis that fluid is blood. In other cases, that fluid may be saline or medications. Vascular access is routinely performed in hospitals, clinics and other medical locations as well as the home (during home hemodialysis for example). For example, vascular connections are disclosed, and more particularly, systems and methods for detecting dislodged vascular connections, and systems and methods for interrupting flow when vascular connections are dislodged are disclosed.

Needle safety systems that have a contact sensing mechanism configured to be put on a patient's skin to determine when a needle/tubing set that has been inserted into a patient and/or has become dislodged from the patient are disclosed. Dislodgement can occur, for example, when tape holding a tissue access device or a vascular access needle in place fails or the line connected to the device is pulled out.

Needle safety systems and methods of using a force-sensing mechanism within the device to determine if and when a given needle/tubing set that has been inserted into a patient has experienced a dislodgement are disclosed. This can occur during medical therapy when the tubing leading to a vascular access needle is purposely or inadvertently 'pulled' or 'tugged'. It can also occur when the medical tape used to hold an inserted needle into position on the skin becomes loose either due to excessive patient hairiness or an increase in sweatiness/humidity that reduces the tape adhesion.

Needle safety systems that have a fluid stop valve configured to automatically deploy to stop the flow of fluid through a needle/tube when the needle delivering that fluid into the body is accidentally dislodged from the patient during fluid delivery are disclosed.

Needle safety systems that have a pinch valve configured to be activated by a mechanical linkage to a mechanical 'skin-sensing' element in a needle system that has been pre-manufactured to include a compressible segment of tubing are disclosed.

Needle safety systems that have the pinch valve configured to block flow acts on an internally formed flow path that is formed within a 'butterfly' housing of a traditional needle are disclosed.

Systems and methods for automatic flow termination for fluid delivery, including a housing configured for coupling a fluid delivery tube to a needle configured for subcutaneous (into vasculature) delivery of fluid within a tissue of a patient and a spring-loaded or fluid-sensitive activation mechanism having a first orientation corresponding to a condition where the housing is disposed substantially adjacent to the tissue and the needle lodged within the tissue and a second orientation corresponding to a condition where the housing is disposed away from the tissue or the needle being dislodged from the tissue and a third orientation corresponding to a condition where the housing is substantially adjacent to the tissue but in a position pulled back from the original insertion point, causing the needle to no longer be delivering fluid into the vasculature are disclosed. A flow termination mechanism coupled to the activation mechanism and having an open configuration allowing flow from the fluid delivery tube to the needle when the activation mechanism is in the first orientation and a closed configuration substantially terminating flow from the fluid delivery tube to the needle when the activation mechanism is in either the second or third orientations is disclosed.

Specialized needles for protecting patients from fluid delivery problems during medical therapies are disclosed. For example, a specialized needle is disclosed that can have a spring-loaded integrated footplate, that, when in a dislodged position (e.g., not taped to skin and needle body off of skin) results in a footplate occlusion member moving into a device flow channel and blocking fluid flow through the needle.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism (shown as a footplate here) having a first flattened orientation (e.g., straight or less straight orientation) corresponding to a condition where the fluid delivery through the needle body is permitted while using the U-opening to protect the needle access hole and a second orientation corresponding to a condition where the fluid tube is occluded via an fluid occlusion member of the footplate during needle dislodgement via the spring force provided by a curved element molded into the footplate are disclosed. When the footplate is created with a curved end, device cannulation is improved due to the low frictional forces associated with the curvature against the skin during insertion. Additionally, the curved end of the footplate encourages mechanical contact with the skin even if the insertion angle is very high (e.g., up to 50 degrees). This enhances dislodgement detection functionality. The use of a curved central portion on the footplate creates an effective internal hinge point for the occlusion arm and removes the need for any external hinge point attachments on the needle body itself. This greatly improves the function of the device by removing any possible mechanical parts of the system from potential interference from any of the overlying medical tape typically used to hold the needle in place during therapy.

Needle safety systems that can be efficiently and cost effectively manufactured by using a 'molded-in' spring design for the footplate sensing unit are disclosed. An effective spring can be manufactured by molding the footplate unit with a curved portion. When this footplate is put into a straightened position, mechanical stress on the curved portion results in the generation of an effective spring force, the direction and magnitude of the force being dependent on the mechanical shape and size of the related appendages. By creating a central 'mechanical arm' the spring force can be harnessed to serve as an occlusion technique by allowing the end of the arm to move directly into and block or occlude the fluid flow through the center of the needle body.

Needle safety systems having a spring-loaded footplate affixed to the bottom of a needle to sense errant flow from a dislodged needle are disclosed. Further, by curving the distal end of the footplate, an effective system can be made that provides for the essential safety and ease of the cannulation process while also simultaneously protecting the patient from needle over-insertion following initial insertion. The curved end also provides a mechanism by which the needle dislodgement detection function can be made effective even for needles inserted at a steep (e.g., up to 45 degrees) insertion angles. The opposite end of this footplate can include an occlusion member which can be pushed into the flow path within the needle body and used to block fluid flow. Further, by molding a curvature into the footplate base and forming an opposable member within the central portion of the footplate, a 'spring' can be formed to aid in the 'sensing' operation and engage the end of the central member to move into the flow path within the needle body and block fluid flow upon removal of the needle from the surface of the patient.

The use of a spring-loaded footplate as the 'detector' of presence of underlying skin to determine if and when a needle body inserted for fluid delivery has been dislodged from the patient is disclosed.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism having a first orientation corresponding to a condition where the fluid delivery tube is pinched internally within the needle body in the event of an axial pull and a second orientation corresponding to a condition where the fluid tube is pinched in an external arrangement for any other non-axial pulling direction are disclosed. A flow termination mechanism can be active in each pull case but otherwise have an open-flow configuration allowing flow from the fluid delivery tube to the needle when the tubing experiences no pulling force or a pulling force below a certain threshold.

Needle safety systems and methods of use are disclosed that use force-sensing mechanisms within the device to determine if and when a given needle/tubing set that has been inserted into a patient has experienced a 'pull force' approaching that which might be reasonably expected to dislodge the tubing from the patient. This can occur during medical therapy, for example, when the tubing leading to a vascular access needle is purposely or inadvertently 'pulled' or 'tugged'. It can also occur when the medical tape used to hold an inserted needle into position on the skin becomes loose either due to excessive patient hairiness or an increase in sweatiness/humidity that reduces the tape adhesion.

Needle safety systems and tubing 'cinch' or 'pinch' methods to stop the flow of fluid through a tube leading to patient in the event that forces on that tube approach those expected to dislodge the needle are disclosed.

Needle safety systems having a device with a mechanically optimized pinch valve on the external portion of the device configured in such a way that the tubing can be pinched by compression of the tubing through optimized pinch points in the event of the tubing being pulled in any other direction beyond axial out of its usual position are disclosed.

Needle safety systems having a device with a mechanically optimized pinch valve on the internal portion of the device configured in such a way that the tubing can be pinched by compression of the tubing via 'pincher arms' within the needle body in the event of the tubing being pulled with an above threshold force in an axial direction sometime after insertion and taping of that needle are disclosed.

Needle safety systems that can override the skin sensing elements described herein are disclosed. The override systems disclosed can insure that the skin sensing elements are not activated during the process of cannulation and/or during needle insertion into the patient. During cannulation, and before the needle are taped down, it is critical that fluid flow is enabled through the needle/tube so that clinical personnel have the ability to visualize blood 'flashback' from the patient through the needle into the fluid flow tube. Any needle with a fluid flow blockage mechanism can have the blockage mechanism temporarily disabled during this cannulation and/or needle insertion period. A needle safety device feature that accomplishes this will be termed a 'cannulation lock' in this document.

Needle safety systems are disclosed that have the ability to 'lock-out' the skin sensing mechanism after it has been activated due to a sliding or other type of off-the-skin dislodgement. In such cases when fluid flow is blocked, it can be important for other aspects of therapy delivery for clinical staff to assess the situation and replace the needle. A 'lock-out' feature insures that no additional and potentially dangerous fluid flow can start again following full activation of the flow stop mechanism.

Needle safety systems for sensing skin contact using a button-like sensor that comes out of (e.g., straight out of) the bottom of a needle body and halting flow using a blockage technique that involves rotating or sliding an opening from close to open within the needle valve are disclosed.

Needle safety systems that have a contact sensing mechanism on the patient's skin to determine when a given needle/tubing set that has been inserted into a patient has potentially become disengaged from the patient in those cases that involve the needle 'sliding' out of the vasculature but not necessarily fully 'dislodging' off-the-body, away from the skin are disclosed. Such incomplete or partial dislodgement can occur when the tape holding a vascular access needle in place provides enough downward pressure to keep the needle against the skin but fails to prevent relevant motion of the access needle away from the original insertion point. One version of this type of failure whereby the needle slides out of the vasculature but not out of the skin is called 'infiltration' in the medical literature. When the needle slides completely out of the skin, this can be defined as 'slip dislodgement'. Dislodgement throughout the disclosure refers to both partial and complete dislodgement.

Needle safety systems for sensing relative motion of the taped down needle body in the direction opposite to the path the needle was originally inserted are disclosed. One way this can be achieved is by using adhesive on the bottom of the needle or a modified surface providing enhanced frictional contact between the needle body and skin and incorporating a method that detects when frictional forces on the needle body are high enough against the needle bottom in the direction opposite of insertion to suggest the needle itself has or is being moved in that undesired (for therapy) direction. In such an event, any of the blockage methods described herein for halting flow within the needle can be activated.

Needle safety systems that can sense relative motion of the needle body in a direction away from the insertion site with reference to the tape above the needle body that is holding it in place are disclosed. This can be achieved by a mechanism which relies on a combination of position, and/or velocity and/or or acceleration change on a member positioned above and in contact with the needle body as well as in contact with the tape. A threshold change in the position, velocity or acceleration of the needle body in a direction away from its intended insertion point as determined by the relative difference between the taped member and the needle body would result in triggering of one of the methods of flow blockage via a linkage between the detection system and one of the integrated flow blockage systems.

The devices disclosed can use no electrical power, and thus require no external power source, batteries, or cables, thereby improving the ability of the devices to be adopted in medical workspaces that are complex and require simplified solutions. The devices disclosed are completely sterilizable and can be completely disposable. The devices disclosed can be manufactured inexpensively using high-volume injection molding processes. The devices disclosed advantageously do not require extensive clinical training.

The needle safety systems disclosed can be added to existing needles/tubing.

Systems, Apparatuses & Methods of Use

FIG. 1 illustrates a variation of a tissue access device 10. The device 10 can withdraw fluid (e.g., blood, lymph, interstitial fluid) from tissue or a vessel lumen. The device 10 can deliver fluid (e.g., blood, lymph, saline, medications) to tissue or a vessel lumen. For example, the device 10 can be used for hemodialysis therapy to withdraw blood from a vessel for filtration and return filtered blood to the vessel. Multiple devices 10 can also be used. For example, for hemodialysis therapy, a first device 10 can be used to withdraw unfiltered blood from a vessel and a second device 10 can be used to return filtered blood to the same or a different vessel. The number of devices 10 used will depend on the number of access points required and can range, for example, from 1 to 5 or more, including every 1 device increment within this range. The device 10 can control the delivery and/or withdrawal of fluid through a channel in the device 10 (also referred to as a device channel and device flow path). For example, the device 10 can automatically decrease (e.g., partially or entirely block) the flow of fluid through the channel when the device 10 becomes dislodged during a dislodgement event.

The device 10 can have multiple device configurations. For example, the device 10 can have a non-occluded configuration and/or one or more occluded configurations. The occluded configurations can correspond to partially occluded configurations, fully occluded configurations, or any combination thereof. When the device 10 is in a non-occluded configuration, fluid can flow through the device channel unrestricted by the device 10. When the device 10 is in an occluded configuration, fluid flow through the device channel can be decreased or entirely blocked by the device 10. The device 10 can restrict or terminate fluid flow through the device channel by decreasing a channel cross-sectional area from a first cross-sectional area to a second cross-sectional area less than the first cross-sectional area. The second cross-sectional area can be about 1% to about 100% less than the first cross-sectional area, including every 1% increment within this range, where 100% can correspond to complete blockage of the channel in one or multiple channel cross-sections. The channel can have a channel longitudinal axis and a channel transverse axis. The channel cross-sectional area can be a transverse cross-sectional area perpendicular to the channel longitudinal axis.

The device 10 can allow less fluid to flow through the device 10 in an occluded configuration than in a non-occluded configuration, for example, as measured over a time interval T (e.g., about 0.25 seconds to about 60.0 seconds). The device 10 can allow less fluid to flow through the device in a first occluded configuration than in a second occluded configuration, for example, as measured over the time interval T, where the second occluded configuration obstructs more of a device flow path than the first occluded configuration. The device 10 can allow more fluid to flow through the device in a first occluded configuration than in a second occluded configuration, for example, as measured over the time interval T, where the second occluded configuration obstructs less of a device flow path than the first occluded configuration.

The device 10 can have a non-occluded configuration or a partially occluded configuration when the device 10 is inserted into or attached to tissue. The device 10 can have an occluded configuration before the device 10 is inserted into tissue, while the device 10 is being inserted into tissue, when the device 10 becomes dislodged or detached from tissue, or any combination thereof.

When the device 10 is inserted into tissue, the device 10 can progressively become less occluded by transitioning from a more occluded configuration to a less occluded configuration. For example, when the device 10 is inserted into tissue, the device 10 can transition from an occluded configuration to a non-occluded configuration. As another example, when the device 10 is inserted into tissue, the device 10 can transition from a first occluded configuration to a second occluded configuration less occluded than the first occluded configuration. The device 10 can have an inserted configuration when insertion into tissue is complete. The device 10 can be removably secured to a non-device 10 surface such as skin, for example, with tape, glue, an elastic band, or any combination thereof. The device 10 can have an attached configuration (also referred to as a non-dislodged configuration) when the device 10 is removably secured to the non-device surface. The inserted and attached configurations can be the same or different from one another. For example, the inserted and attached configurations can both be non-occluded configurations or partially occluded configurations. As another example, the inserted configuration can be an occluded (partial or full) configuration and the attached configuration can be a non-occluded configuration or an occluded configuration less occluded than the occluded inserted configuration.

When the device 10 becomes dislodged from the non-device surface, the device 10 can progressively become more occluded by transitioning from a less occluded configuration to a more occluded configuration. For example, when the device 10 becomes dislodged from the non-device surface, the device 10 can transition from a non-occluded configuration to an occluded configuration. As another example, when the device 10 becomes dislodged from the non-device surface, the device 10 can transition from a first occluded configuration to a second occluded configuration more occluded than the first occluded configuration. The device 10 can have a dislodged configuration when one or more portions of the device 10 move away from the non-device surface by an occlusion threshold distance of about 5 mm to about 25 mm, including every 1 mm increment within this range.

The device 10 can automatically move from an attached configuration to a dislodged configuration when the device 10 is dislodged or detached from the non-device surface. The device 10 can transition from the attached configuration to the dislodged configuration in less than 0.10 seconds, 0.25 seconds, 1 second, 5 seconds, 10 seconds, or 60 seconds. For example, the device 10 can automatically move from the attached configuration to the dislodged configuration in 0.01 seconds to 1.00 seconds, including every 0.01 second within this range (e.g., 0.10 seconds).

FIG. 1 illustrates a variation of an occluded configuration of the device 10, for example, a partially occluded configuration or a fully occluded configuration. FIG. 1 further illustrates that the device 10 can have the same configuration before the device 10 is inserted into tissue and attached to a non-device surface and after the device 10 is dislodged from the non-device surface. When the device 10 is detached from the non-device surface, the device 10 may remain in the tissue or become dislodged from the tissue as well. For example, when the device 10 is dislodged from the non-device surface, a portion of the device 10 that is in a vessel (e.g., a needle) may remain in the vessel, may be dislodged from the vessel but remain in tissue adjacent the vessel, or may be dislodged from the vessel and tissue altogether.

FIG. 1 further illustrates that the device 10 can have a device longitudinal axis A1. The device longitudinal axis A1 can be a center longitudinal axis of the device 10. The device longitudinal axis A1 can be a center longitudinal axis of a flow channel in the device 10. The device longitudinal axis A1 can be straight or curved. The device longitudinal axis A1 can be perpendicular to a device first transverse axis A2. The device longitudinal axis A1 can be perpendicular to a device second transverse axis A3. The device first and second transverse axes A2, A3 can be perpendicular to one another. The device first and second transverse axes A2, A3 can be straight or curved.

The device 10 can have a device proximal end 10*a* and a device distal end 10*b*. The device 10 can have a device first side 10*c* and a device second side 10*d*. The device first side 10*c* can be a bottom surface of the device 10 and the device second side 10*d* can be a top surface of the device 10.

FIG. 1 further illustrates that the device 10 can have a needle 12 and a housing 14 (also referred to as a needle body). The needle 12 can be, for example, an arteriovenous (AV) fistula butterfly needle or an AV fistula cannula needle housed in a flexible sheath (not shown). The needle 12 can have a needle proximal end 12*a* and a needle distal end 12*b*. The housing 14 can be a butterfly housing. For example, the housing 14 can have a first wing 15*a* and a second wing 15*b*. The housing can have a housing proximal end 14*a* and a housing distal end 14*b*. A needle hub 13 can connect the needle and housing 12, 14 together. The device 10 can have a connector 16 configured to connect a tube 8 to the device 10. The connector 16 can be outside and/or inside the housing 14. Additionally or alternatively, the connector 16 can be integrated with the housing 14. The tube 8 can be in fluid communication with the needle 12 via a flow channel in the housing 14 when connected to the device 10 (e.g., via the connector 16). The connector 16 can be a rigid material, a semi-rigid material, or a flexible material. The housing can be made of a rigid material, for example, plastic, metal, composite material, or any combination thereof. The tip of the needle 12 can be a distal terminal end of the device along the device longitudinal axis A1.

FIG. 1 further illustrates that the device 10 can have a sensor 18. The sensor 18 can be a non-device surface sensor, for example, a skin sensor. The sensor 18 can be a mechanical sensor. The sensor 18 can be a valve, for example, a pinch valve. One or more portions of the sensor 18 can be resiliently movable. For example, one or more portions of the sensor 18 can be biased to resiliently strain away from a sensor neutral position (e.g., via compression and/or tension) and de-strain back to the sensor neutral position. The sensor 18 can change shape when a force is applied to the sensor 18 from a non-device surface (e.g., when the device 10 is inserted and attached to skin). The sensor 18 can change shape when a force is removed from the sensor 18 (e.g., when the device 10 becomes dislodged from skin).

The sensor 18 can comprise, for example, one or more arms, plates, protrusions, extensions, occluders, openings, channels, springs, spring regions, or any combination thereof. The sensor 18 can be positioned on a device first side (e.g., a first transverse side, a bottom side), a device second side (e.g., a second transverse side, a top side), a device third side (e.g., first lateral side, a left side), a device fourth side (e.g., a second lateral side, a right side), a device fifth side (e.g., first longitudinal side, a front side), a device sixth side (e.g., second longitudinal side, a back side), or any combination thereof. For example, the sensor 18 can be a bottom plate (also referred to as a footplate), a top plate, a side plate, a front plate, a back plate, or any combination thereof, such that at least a portion of the sensor 18 can detect contact and loss of contact with a non-device surface and/or can detect a contact force and a reduction of the contact force from a non-device surface. For example, FIG. 1 illustrates that the sensor 18 can be a skin-sensing footplate (also referred to as a movable footplate).

The sensor 18 can have a sensor proximal end 18*a* and a sensor distal end 18*b*. The sensor proximal and/or distal ends 18*a*, 18*b* can be configured to slide across a non-device surface when the needle 12 is inserted into tissue. The sensor distal end 18*b* can have a sensor distal terminal end 24. The sensor distal terminal end 24 can be an edge or a surface.

The sensor 18 can be attached to the device 10 (e.g., the housing 14) with or without a hinge. For example, FIG. 1 illustrates that the sensor proximal end 18*a* can be directly or indirectly attached to the housing 14 on the device first side 10*c* without a hinge. The portion of the sensor 18 attached to the housing 14 (e.g., the sensor proximal end 18*a*) can be attached using glue, welding (e.g., sonic welding), a snap fit, a friction fit, or any combination thereof.

The sensor distal end 18*b* can move relative to the sensor proximal end 18*a*. For example, the sensor distal end 18*b* can rotate about a sensor hinge (not shown). The sensor hinge can be attached to or integrated with the sensor 18. The sensor hinge can be a spring. The sensor 18 can have multiple sensor hinges/springs.

A sensor spring (not shown, also referred to as a spring region) can result in the distal end 18*b* being located a distance away from the needle 12 during dislodgement (and before attachment). The sensor spring can cause the sensor distal end 18*b* to be biased in a neutral position a distance away from the needle 12 during dislodgement (and before attachment).

The sensor distal end 18*b* can have one or more distal end sections, for example, 1 to 10 or more sections, including every 1 section increment in this range (e.g., 2 sections, 3 sections). One or more of the distal end sections can be straight. One or more of the distal end sections can be curved. The sensor distal end sections can be angled relative to one another, for example, by about 0 degrees to about 120 degrees, including every 1 degree increment within this range (e.g., 90 degrees).

For example, FIG. 1 illustrates that the sensor distal end 18*b* can have a distal end first section 20*a*, a distal end second section 20*b*, and a distal end third section 20*c* between the distal end first and second sections 20*a*, 20*b*. FIG. 1 illustrates that the first and second sections 20*a*, 20*b* can be straight and that the third section 20*c* can have a curve 21. The first and second sections 20*a*, 20*b* can be angled relative to one another by about 90 degrees. Different distal end sections can be integrated with or attached to one another. For example, the sensor distal end 18*b* can be a monolithic structure. The sensor 18 can be a monolithic structure.

A curved sensor distal end (e.g., distal end 18*b* with curve 21) can improve caregiver usability of the device 10 by making the needle insertion process and/or the cannulation process easier by reducing friction between the device 10 and a non-device contact surface during insertion. For example, the curve/curved surface 21 can result in a sensor leading edge (e.g., the sensor terminal end 24) facing or extending away from the non-device surface (e.g., away from a patient's skin surface) during insertion. Having the sensor leading edge 24 face or extend away from the insertion surface during needle insertion can ensure easier cannulation by reducing or removing the possibility of the sensor leading edge catching on the insertion surface when the needle 12 is inserted.

A curved distal end 18*b* can also protect patients by preventing needle over-insertion. For example, the distal end second section 20*b* can be configured to prevent over insertion of the needle 12 into a vessel by acting as a barrier that prevents the needle 12 from being inserted past the second section 20*b*. The curved end offers protection to the patient in this position by 'blocking' the needle body from any forward motion into the existing needle access hole (not shown). The sensor distal end 18*b* can have a section (e.g., section 20*b*) that extends toward the needle 12 with or without a curve 21 in the sensor distal end 18*b* such that the sensor distal end 18*b* can define a needle over insertion barrier (e.g., section 20*b*) in any variation of the sensor 18. Such barriers can inhibit or prevent over insertion of the needle 12 longitudinally and/or transversely into the skin, for example, relative to a longitudinal axis of the needle 12 and/or relative to the needle insertion hole in the skin.

A curved distal end 18*b* can also desirably enable needle dislodgement detection even for needles (e.g., needle 12) inserted at steep insertion angles, for example, up to 45 degrees, up to 50 degrees, up to 60 or more degrees. The curved end allows for maximal contact between the skin and a closed sensor 18 (not shown, this can be the configuration of the sensor 18 when the device 10 is in an attached configuration) under these steep insertion angle conditions, offering increased device functionality by ensuring the sensor 18 is held in check against the needle 12 regardless of the insertion angle.

The sensor distal end 18*b* can have a sensor opening 22 (also referred to as a sensor slot). The sensor opening 22 can accept a portion of the needle 12. For example, FIG. 1 illustrates that the sensor distal end second section 20*b* can have the sensor opening 22. The sensor opening 22 can be configured to receive at least a portion of the needle 12 when the sensor distal end 18*b* is pressed by a non-device surface toward the needle 12, for example, when the device 10 is in an inserted or attached configuration. The sensor opening 22 can advantageously allow for closure (e.g., full closure) of the sensor 18 against the needle 12 when the sensor distal end 18*b* is pressed toward the housing 14 (e.g., against the housing 14). The sensor opening 22 can be, for example, a U-shape, a V-shape, or an irregular shape. At least a portion of the distal terminal end 24 can define the sensor opening 22.

A sensor opening 22 integrated with the sensor distal end 18*b* can allow the over insertion barrier (e.g., barrier 20*b*) to close around at least a portion of the needle 12 when the device is in an attached configuration. The sensor opening 22 can allow the barrier 20*b* to better prevent over insertion be increasing the surface area of the barrier near the needle 12 that can resist further insertion of the needle 12. The barrier 20*b* can positioned between the needle tip and the needle hub 13. The sensor opening 22 can be positioned between the needle tip and the needle hub 13. Such placement can ensure that the needle 12 cannot be inadvertently pushed deeper into the patient through the existing needle access hole.

FIG. 2A illustrates that the sensor 18 can have one or more sensor springs 26 (also referred to as spring regions), for example, 1 to 10 or more springs 26, including every 1 spring increment within this range (e.g., 1 spring, 2 springs). For example, FIG. 2A illustrates that the sensor 18 can have a first spring 26*a* and a second spring 26*b*. When multiple springs 26 are used, the multiple springs 26 (e.g., first and second springs 26*a*, 26*b*) can function together as a single spring.

The spring 26 (e.g., first and second springs 26*a*, 26*b*) can function like a leaf spring, a compression spring, a tension spring, a torsion spring, or any combination thereof. Each spring 26 can be, for example, a leaf spring, a compression spring, a tension spring, or a torsion spring. The first and second springs 26*a*, 26*b* can be the same or a different type of spring. For example, the first spring 26*a* can be a leaf spring and the second spring can be a compression spring. As another example, the first and second springs 26*a*, 26*b* can both be, or function like, a leaf spring.

The spring 26 can be integrated with, attached to, or embedded in the sensor 18. For example, the spring 26 can be a molded spring made of the same or different material as the rest of the sensor 18. A molded spring 26 can be manufactured by molding the sensor 18 with one or more non-straight resilient portions (e.g., first and second spring regions 26*a*, 26*b*) that can function as a spring when the shape of the resilient portions are changed (e.g., straightened). The non-straight resilient portions can be, for example, curved, polyarc, and/or polyline structures, members, bars, rods, shafts, sheets, laminates, or any combination thereof. A molded spring design can advantageously reduce manufacturing costs associated with the sensor 18, for example, as compared to attaching or embedding a separate spring 26 to or in the sensor 18.

The spring 26 can have the form of a curved or angled polyline structure when the spring 26 is in a neutral configuration (e.g., undeflected configuration, non-strained configuration, non-stressed configuration). The spring 26 can have a neutral configuration when the device 10 is in a dislodged configuration (e.g., the dislodged configuration of FIG. 2A) and/or before the device 10 is attached to tissue. The spring 26 can be less curved or angled when the device 10 is in an attached configuration, for example, when the spring 26 is in a compressed and/or tensioned configuration (e.g., non-neutral configuration). For example, when the sensor 18 in FIG. 2A is put into a straightened or less curved configuration, mechanical stress on the curved portion (the spring regions 26a and 26b) can result in the generation of an effective spring force. This spring force can bias the sensor 18 to return to the initial configuration. The direction and magnitude of the spring force can be dependent on the mechanical shape and size of the related appendages of the sensor 18 (e.g., a flow restrictor, the features of the sensor distal end 18b).

The spring 26 can be a sensor hinge configured to allow the sensor distal end 18b to move (e.g., rotate) relative to the sensor proximal end 18a.

The spring 26 (e.g., springs 26a and 26b) can connect the sensor proximal end 18a to the sensor distal end 18b. The spring 26 can be in a middle region of the sensor 18, and/or on the sensor distal end 18b or on the sensor proximal end 18a. As another example, the spring 26 can extend across all or a portion of both the device proximal and distal ends 18a, 18b. For example, FIG. 2A illustrates that the spring 26 can be on a sensor proximal end 18a, where the sensor proximal and distal ends 18a, 18b is shown separated by a sensor center transverse axis A4. The sensor transverse axis A4 can be curved or straight.

FIG. 2A further illustrates that the sensor 18 can have a flow restrictor 28. The flow restrictor 28 can have an occluder arm 30 and an occluder 32. The occluder 32 can be a protrusion that extends away from the occluder arm 30, for example, toward the device longitudinal axis A1. The flow restrictor 28 can be integrated with or attached to the sensor 18. The occluder 32 can be configured to occlude the device flow path when the device 10 is in a dislodged configuration. The occluder 32 can be rigid. The occluder 32 can be non-deformable. The occluder 32 can be flexible. The occluder 32 can have a blunt tip. The occluder 32 can have a sharp tip. The occluder 32 can be straight and/or curved. The occluder 32 can have an irregular shape. A spring region 26 can be on one or both lateral sides of the flow restrictor 28. The spring 26 can resiliently bias the flow restrictor 28 into a default occluding position. For example, the spring force of the spring 26 can move the occluder 32 directly into and block or occlude fluid flow through the device flow path when the device 10 becomes dislodged. The curved regions 26a and 26b create an internal or integrated hinge point for the flow restrictor 28. The sensor 18 can have a sensor hole 36 that can receive the flow restrictor 28 when the sensor is straightened. Alternatively or additionally, all or part of the sensor hole 26 can be a recess in the sensor 18. The flow restrictor 28 can be in a center of the hole/recess 36 or offset in the hole/recess 36.

By using a curved portion of the sensor 18 as the mechanical spring, a typical hinge that might otherwise be required for tilting a member from a flat position to an angled position is not required. Further, by tightly affixing one portion of the footplate 18 to the needle body 14 using glue, sonic welding or any other technique (e.g., friction fit, snap fit), the footplate 18 can be made to serve in a spring-like way to sense underlying skin and serve as the mechanism for occluding blood flow. A hinge point A5 becomes integrated into the footplate's central occlusion member 28 at the base of the occluder arm 30 as that point where the central curvature 26 creates a natural bending motion. This design can desirably remove the need for a traditional hinged attachment on the needle body 14, allowing the mechanics of the device 10 to become much less susceptible to interference, for example, from the standard medical tape that is typically placed over the needles devices 10 to hold them in place.

The sensor 18 can have one more attachment zones 34. The attachment zones 34 can allow for hingeless attachment of the sensor 18 to the housing 14. The attachment zones 34 can be attached to the housing 14. For example, the attachment zones can be glued or welded (e.g., sonic welded) to the housing 14. As another example, the attachment zones 34 can fit into corresponding recesses in the housing 14 with a snap fit, a friction fit, an adhesive fit, or any combination thereof.

FIG. 2B illustrates that the sensor 18 can have a sensor first longitudinal axis A6 and a sensor second longitudinal axis A7. The sensor first longitudinal axis A6 can be an occluder arm longitudinal axis. The sensor first longitudinal axis A6 can be a center longitudinal axis of the occluder arm 30. The sensor first longitudinal axis A6 can be curved or straight. The sensor second longitudinal axis A7 can be a longitudinal axis of the portion of the sensor proximal end 18a that is proximal to the spring portions 26. The sensor second longitudinal axis A6 can be a center longitudinal axis of the sensor proximal end 18a. The sensor second longitudinal axis A7 can be curved or straight. There can be an angle 38 between the sensor first and second longitudinal axes A6, A7. When the device 10 is in a dislodged configuration, the sensor 18 can be in an occluded configuration (also referred to as a sensor closed configuration) such that the angle 38 is about 10 degrees to about 75 degrees, including every 1 degree increment within this range (e.g., 25 degrees, 30 degrees). When the device 10 is in an attached configuration, the sensor 18 can be in a less occluded configuration than when the device 10 is in a dislodged configuration (also referred to as a sensor open configuration) such that the angle 38 is about 0 degrees to about 30 degrees, including every 1 degree increment within this range (e.g., 0 degrees, 2 degrees, 5 degrees). The angle 38 between the sensor first and second longitudinal axes A6, A7 can be less when the sensor 18 is in the open configuration than when the sensor 18 is in the closed configuration, for example, about 10 degrees to about 75 degrees less, including every 1 degree increment within this range.

FIG. 2B further illustrates that the sensor 18 can have a sensor first transverse axis A8 and a sensor second transverse axis A9. The sensor first transverse axis A8 can be an axis of the sensor distal terminal end (e.g., of sensor distal end second section 20b). The sensor first transverse axis A8 can be a center axis of the sensor distal end second section 20b. The sensor first transverse axis A8 can be curved or straight. The sensor second transverse axis A9 can be an axis of the occluder 32. The sensor second transverse axis A9 can be a center axis of the occluder 32. The sensor second transverse axis A9 can be perpendicular to an axis of the occluder arm 30 (e.g., perpendicular to axis A7). The sensor second transverse axis A9 can be curved or straight. The sensor first and second transverse axes A8 and A9 can be parallel or non-parallel to each other. As another example, one or both of the sensor first and second transverse axes A8 and A9 can extend at least partially in a longitudinal direction, for example, along axes A6 and/or A7. As yet another example, one or both of the sensor first and second longitudinal axes A6 and A7 can extend at least partially in a transverse direction, for example, along axes A8 and/or A9.

FIG. 2B further illustrates that the sensor distal end 18b can have a transverse dimension 40 as measured along axis A8 of about 5 mm to about 20 mm, including every 1 mm increment within this range (e.g., 8 mm). A sensor opening transverse dimension 42 can be about 2 mm to about 20 mm, including every 1 mm increment within this range (e.g., 5 mm). As another example, the sensor opening transverse dimension 42 can be the same as the transverse dimension 40. The sensor opening transverse dimension 42 can be selected so that the needle 12 is configured to contact or sit above a bottom surface of the sensor opening 22 when the device 10 is in an attached configuration. Selecting the opening transverse dimension 42 so that the needle 12 does not contact the bottom surface of the sensor opening 22 when the device 10 is in an attached configuration can advantageously allow the needle 12 to float within the sensor opening 22 so that the sensor distal end 18b does not push the needle 12 upward out of the skin during insertion. Allowing the needle 12 to float in the sensor opening 22 can be useful where the user must "fish" for a vessel during insertion such that the user is changing the angle of the device 10 with respect to a patient's skin while a portion of the needle is inserted in tissue. It can also be useful where the angle of the device 10 relative to skin is atypically low (e.g., less than 30 degrees, less than 20 degrees, less than 10 degrees). The angle of the device 10 relative to the skin can be measured between the skin surface and the device longitudinal axis A1.

FIG. 2B further illustrates that the occluder 32 can have a transverse dimension 44 as measured along axis A9 of about 1 mm to about 15 mm, including every 1 mm increment within this range (e.g., 4 mm, 5 mm).

FIG. 2B further illustrates that the sensor 18 can have a sensor first contact surface 48 and a sensor second contact surface 50. The sensor first contact surface 48 can be configured to removably contact a non-device surface such as skin, and is therefore also referred to as a skin contact surface 48. The sensor second contact surface 50 can be configured to removably contact a device surface such as a surface of the housing 14, and is therefore also referred to as a housing contact surface 50.

FIG. 2C illustrates that the occluder opening 22 can extend through the sensor distal end second and third sections 20b, 20c. A sensor opening longitudinal dimension 46 can be about 0 mm to about 50 mm, including every 1 mm increment within this range (e.g., 5 mm). Having a sensor opening longitudinal dimension 46 greater than zero can allow the needle 12 to float in the sensor opening 22 during low angle insertions. A sensor opening longitudinal dimension 46 greater than zero can also desirably decrease the material needed to make the sensor 18, thereby reducing the manufacturing costs.

FIG. 2C further illustrates that the sensor 18 can have a dimension 47 measured between the sensor proximal terminal end and the sensor distal terminal end. The dimension can be, for example, from about 10 mm to about 50 mm or more, including every 1 mm increment within this range. The dimension 47 can be the longitudinal length of the sensor 18 as measured along a straight axis or along a curved axis that follows the contour of the sensor 18 when in the neutral position of FIG. 2A.

FIGS. 1-2C illustrate that the device 10 can have a spring 26, a flow restrictor 28, an over insertion protector (e.g., sensor distal end second section 20b), or any combination thereof. Any combination of the spring 26, the flow restrictor 28, and the over insertion protector can be integrated with one another. For example, the spring 26 and the flow restrictor 28 can be integrated with each other. The spring 26, the flow restrictor 28, and the over insertion protector (e.g., sensor distal end 18b) can be integrated with one another. As another example, the spring 26 can have an integrated flow restrictor (e.g., flow restrictor 28). The spring 26 can have an integrated over insertion protector (e.g., distal end of the sensor distal end 18b). The spring 26 can have an integrated flow restrictor (e.g., flow restrictor 28) and an over insertion protector (e.g., distal end of the sensor distal end 18b).

Additionally or alternatively, the device 10 can have an over insertion protector attached to or integrated with the housing 14 and/or needle hub 13 different from the over insertion protector that can be part of the sensor 18. In such variations, the over insertion protector can be an elongate element (e.g., a bar, a plate) that extends at least partially in a longitudinal direction away from the needle hub 13 and at least partially in a transverse direction toward the needle 12. For example, the over insertion protector can have the same shape as the sensor distal end 18b, with it just being flipped upside down and attached to or integrated with the housing 14 (where the "same shape" can be without the sensor proximal end 18a, without the spring 26, and without the flow restrictor 28). The over insertion protector can have an opening similar to or the same as opening 22. The over insertion protector can be on the device second side 10d and/or one of the device lateral sides. Where the device 10 has an over insertion protector not attached to or integrated with the sensor 18b, but instead has one attached to the housing 14 and/or to the needle hub 13, the sensor distal end second section 20b can be shortened relative to what is shown in FIGS. 1-2C so that it does not extend as far toward the needle 12 (e.g., 5 mm to 15 mm shorter), for example, so that the sensor distal end second section 20b does not interfere with the over insertion protector. As another example, the device 10 can have both a first insertion protector attached to or integrated with the sensor 18 and a second insertion protector attached to or integrated with the housing 14 and/or the needle hub 13.

Another variation of the flow restrictor 28 can be a flow restrictor having the occluder arm 30 but no occluder 32. In such variations, the occluding portion of the sensor 18 can be the end of the straight bar 30 (e.g. where the occluder is positioned on flow restrictor 28). The occluder arm 30 can be a tapered bar. As another example, the occluder arm 30 can be one or more curved, polyline, and/or polyarc bar sections (e.g., different from the occluder projection 32) such that the bar 30 can still function as an occluder without having the occluder 32 illustrated in FIGS. 2A-2C.

The sensor 18 can have one spring 26. For example, another variation of the sensor 18 can be half of the sensor 18 shown in FIGS. 2A-2C. Such a sensor can still function as described herein, albeit with one spring 26 (e.g., spring 26a or spring 26b) instead of two. Axis A10 in FIG. 2C illustrates a variation of where the sensor 18 can be sliced to create a smaller sensor 18. One or both halves of the sensor can be manufactured. As another example, the sensor proximal end 18a can remain unchanged in a one-spring sensor, but the sensor distal end 18b attached to the sensor proximal end 18a can be half of the structure as split by axis A10 in FIG. 2C (e.g., the left or right side of the sensor 18). Such one-spring sensors 18 may or may not have sensor openings 22. If there is no opening 22, the sensor distal end 18b can still function as a barrier to prevent over insertion.

FIGS. 3A and 3B illustrate the device 10 in a variation of an attached configuration. To maintain this attached configuration, the device 10 can be taped against a non-device surface such as skin. Neither the tape nor the skin is illustrated in FIGS. 3A and 3B for purposes of clarity.

FIGS. 3A and 3B further illustrate that the device 10 can have an attached configuration when an external force 80 is applied by a non-device surface (e.g., skin) to the device first side 10c. Although not illustrated in FIGS. 3A and 3B, the device 10 can be attached to the skin, for example, with tape or glue to secure the device 10 in the attached configuration.

FIG. 3A illustrates that the housing contact surface 50 can abut the housing 14 when the device 10 is in an attached configuration. All or a portion of the skin contact surface 48 can contact skin when the device 10 is in an attached configuration, including, for example, the sensor proximal end 18a, the sensor distal end 18b, the spring region 26, the occluder arm 30, or any combination thereof. For example, for the sensor distal end 18b, the skin contact surface 48 of the sensor distal end third section 20c, the sensor distal end second section 20b, the sensor distal end first section 20a, the sensor distal end portion between the sensor distal end first section 20a and the sensor proximal end 18a, or any combination thereof, can contact skin when the device 10 is in an attached configuration. The sensor distal end first section 20a can extend from the sensor distal end third section 20c to the distal proximal end 18a and/or a distal end of the springs 26. The portion of the skin contact surface 48 that contacts tissue when the device 10 is in an attached configuration will depend on factors such as the insertion angle, the depth of needle insertion, and the location of the tape across the top of the device 10.

FIG. 3A further illustrates that the sensor second longitudinal axis A7 can be parallel to the device longitudinal axis A1 when the device 10 is in an attached configuration. In such variations, FIG. 3A illustrates that a portion of the sensor distal end 18b (e.g., the sensor distal end first section 20a) can extend at least partially in a longitudinal direction (e.g., in solely a longitudinal direction) toward device distal end 10b when the device 10 is in an attached configuration. As another example, the axis A7 can be angled from about 0 degrees to about 15 degrees relative to the device longitudinal axis A1 when the device 10 is an attached configuration, including every 1 degree increment within this range (e.g., 3 degrees). Non-parallel configurations (e.g., angles above 0 degrees) can occur where the skin surface is rough. A non-parallel configuration of the sensor axis A7 can also be transitory, for example, temporarily moving above 0 degrees when the patient moves and the needle 12 and/or the housing 14 slightly lifts off the skin or slightly moves further away from the skin (e.g., where the needle and the housing are not in contact with the skin other than at the needle insertion hole when the device 10 is in an attached configuration). The spring 26 can be biased to keep the sensor 18 in contact with the skin during patient movement such that the sensor distal terminal end 24 moves toward or past (e.g., via rotating) the device longitudinal axis A1 in the device configuration of FIG. 3A. The sensor axis A7 can return to a parallel orientation with the axis A1 once the patient has stopped moving (e.g., if the tape remains in place). Allowing the sensor 18 to move during patient movement gives the device 10 flexibility and can make movement for the patient more comfortable.

FIG. 3A further illustrates that the sensor first transverse axis A8 can be perpendicular to both the device longitudinal axis A1 and the sensor second longitudinal axis A7 when the device 10 is in an attached configuration. In such variations, FIG. 3A illustrates that a portion of the sensor distal end 18b (e.g., the sensor distal end second section 20b) can extend at least partially in a transverse direction (e.g., in solely a transverse direction). The sensor distal end second section 20b can also extend at least partially in a longitudinal direction toward the device distal end 10 and/or toward the device proximal end 10a when the device 10 is in an attached configuration. For example, the axis A8 can be angled about 0 degrees to about 150 degrees relative to axes A1 and/or A7 when the device 10 is an attached configuration, including every 1 degree increment within this range (e.g., 60 degrees, 90 degrees, 120 degrees). Angles less than 90 degrees can correspond to where the sensor distal end 18b extends at least partially in a longitudinal direction away from the needle tip and toward the device proximal end 10a when the device is in an attached configuration. Angles greater than 90 degrees can correspond to where the sensor distal end 18b extends at least partially in a longitudinal direction toward the needle tip and away from the device proximal end 10a when the device 10 is in an attached configuration. The angle between axes A7 and A8 can be the angle between the sensor distal end first and second sections 20a, 20b, respectively. The angle between axes A7 and A8 can be fixed such that the angle between the sensor distal end first and second sections 20a, 20b remains constant when the device 10 changes configurations. The portion of the sensor distal end 18b that extends transversely toward the needle 12 can comprise the over insertion barrier of the device 10.

FIG. 3A further illustrates that the sensor distal end 18b can extend beyond the needle hub 13 when the device 10 is in an attached configuration. For example, the sensor distal end 18b can extend a longitudinal distance 58 beyond a distal end of the needle hub, as measured to a proximal edge or surface of the sensor distal end 18b. The distance 58 can be, for example, about 1 mm to about 15 mm, including every 1 mm increment within this range (e.g., 1 mm, 2 mm, 3 mm).

FIG. 3A further illustrates that the sensor distal terminal end 24 can extend beyond the device longitudinal axis A1 when the device 10 is in an attached configuration. For example, the sensor distal terminal end 24 can extend a transverse distance 60 beyond the axis A1. The distance 60 can be, for example, 1.0 mm to about 7.5 mm, including every 0.1 mm increment within this range (e.g., 1.0 mm, 2.0 mm, 3.0 mm, 4.0 mm). The sensor distal terminal end 24 can be the sensor transverse terminal end. The sensor 18 can have a sensor longitudinal terminal end as well, which can be, for example, the distal edge or surface of the sensor distal end second section 20b. The sensor distal end 18b can be transversely below, partially adjacent to, and/or transversely beyond the shaft of the needle 12 (e.g., relative to an attachment orientation). For example, FIG. 3A illustrates that the that the sensor distal terminal end 24 can be above the shaft of the needle 12 when the device 10 is in an attached configuration.

The distances 58 and 60 can be the same or different from one another. For example, FIG. 3A illustrates that the distance 58 can be less than the distance 60, for example, by about 1 mm or about 2 mm. As another example, the distance 58 can be greater than the distance 60 (e.g., by about 1 mm to about 15 mm).

FIG. 3B illustrates that the device 10 can have an insert 17 (also referred to as a membrane insert). The insert 17 can be positioned in a housing space 51. The housing space 51 can define a housing channel. Part of the insert 17 can be inside the housing 14 and part of the insert 17 can be outside the housing 14. For example, the portion of the insert 17 outside of the housing 14 can define the connector 16. As another example, the insert 17 can be entirely within the housing 14. In such variations, the connector 16 can be attached to the housing 14, integrated with the housing 14, attached to the insert 17, or any combination thereof. The insert 17 can have ribs 49 that can grip the needle 12 to hold it in place. Glue can be in the space between the ribs. The ribs 49 can be on a proximal and/or distal end of the insert 17.

The insert 17 can be rigid, semi-rigid, flexible, resilient, and/or deformable. The insert 17 can be made of the same or a different material as the housing 14. The insert 17 can be softer, more flexible, more resilient, or more deformable than the housing 14. The insert 17 can be made of multiple materials. An insert first material can be softer, more flexible, more resilient, more deformable, or any combination thereof, than an insert second material. The insert 17 can have one or multiple thicknesses. For example, the insert 17 can have an insert first thickness 17a and an insert second thickness 17b less than the insert first thickness 17a. The insert first and second thicknesses 17a, 17b can be transverse thicknesses. The insert first thickness 17a can range from about 0.5 mm to about 3.0 mm, including every 0.1 mm increment within this range (e.g., about 1.5 mm). The insert second thickness 17b can range from about 0.1 mm to about 2.0 mm, including every 0.1 mm increment within this range (e.g., about 0.2 mm).

FIG. 3B further illustrates that the device 10 can have a resilient membrane 54 (also referred to as a deformable membrane and a deflectable membrane). The membrane 54 can be positioned adjacent the flow restrictor 28. The membrane 54 can be made of the same or different material as the insert 17. The membrane 54 can be attached to or integrated with the insert 17. A portion of the insert 17 can be the membrane 54. For example, the membrane 54 can be the portion of the insert made of the insert first material, the membrane 54 can be the portion of the insert 17 having the insert second thickness 17b, the membrane 54 can be the portion of the insert 17 adjacent the flow restrictor 28, or any combination thereof. As another example, the membrane 54 can be separate from the insert 17.

The insert 17 can have an outer surface and an inner surface. The insert outer surface can be attached to or in contact with an inner surface of the housing 14. The insert inner surface and/or an inner surface of the membrane 54 can define an insert channel 56 (also referred to as an insert flow channel and a housing conduit). The housing conduit 56 can extend from the housing proximal end 14a to the housing distal end 14b. The housing conduit 56 can be straight or curved. A proximal portion of the needle 12 can be in the insert channel 56. The insert inner surface can have a circular, elliptical, or polygonal transverse cross section (e.g., in a plane defined by axes A2 and A3). The insert outer surface can have a circular, elliptical, or polygonal transverse cross-section (e.g., in a plane defined by axes A2 and A3). The membrane 54 can be in the housing 14. The membrane 54 can be outside of the housing 14. The membrane 54 can be integrated with or attached to the housing. For example, the non-fluid contact side of the membrane 54 can form an exterior and/or interior surface of the housing 14.

Prior to the device 10 being inserted into tissue, the resilient membrane 54 can have a deformed shape from the spring 26 forcing the occluder 32 to press up against the membrane and force it into the housing conduit 56. When the device 10 is inserted into tissue, the resilient membrane 54 can undeform from the membrane first shape (e.g., occluded shape) to a membrane second shape (e.g., a non-occluded or less occluded shape). When the device 10 becomes dislodged, the occluder 32 can again deform the membrane 54 into the housing flow path 56 by the action of the spring 26, thereby decreasing the cross-sectional area of the housing flow path 56 in the occlusion area to restrict or terminate flow.

FIG. 3B further illustrates that the device 10 can have a device flow channel 62. The device flow channel 62 can include a needle flow channel 64 and one or both of the insert flow channel 56 and the housing channel 51. The device flow channel 62 can be in fluid communication with a tube flow channel 66 when the tube 8 is connected to the device 10. The housing conduit 56 (e.g., insert flow channel 56) can be parallel with the device longitudinal axis A1. The housing conduit 56 can be concentric with or offset from the device longitudinal axis A1. The needle flow channel 64 can be parallel with the device longitudinal axis A1. The needle flow channel 64 can be concentric with or offset from the device longitudinal axis A1. The needle 12 can be at an angle of about 0 degrees to about 45 degrees relative to the housing conduit 56 such that the needle flow channel 64 can be at an angle of about 0 degrees to about 45 degrees relative to the flow path of the housing conduit 56.

The device flow channel 62 can have a channel occlusion region 68 (also referred to as a conduit occlusion region). The channel occlusion region 68 of the device flow channel 62 can be at least partly defined by the membrane 54. For example, the membrane 54 can define at least part of the perimeter (e.g., circumference) of the transverse cross-sections of the device flow channel 62 in the occlusion region 68. The membrane 54 can define, for example, about 10% to about 75% of the perimeter, including every 1% increment within this range (e.g., 25% or less, 50% or less, 75% or less). FIG. 3B illustrates that the membrane 54 can define about 25% to about 50% (e.g., 50%) of the perimeter where the 25% to 50% forms or is part of the bottom half of the occlusion region 68 from a proximal to a distal end of the occlusion region 68. As another example, the channel occlusion region 68 can be entirely or at least partly defined by the insert 17 such that the insert 17 can partly or entirely define the perimeter (e.g., circumference) of the transverse cross-sections of the device flow channel 62 in the occlusion region 68. As yet another example, the perimeter (e.g., circumference) of the channel occlusion region 68 can be partly defined by the membrane 54, at least partly defined by the insert 17, at least partly defined by the housing 14, or any combination thereof, for example, about 0% to about 100% of the perimeter, depending on the combination, where all percentage permutations of these various perimeter combinations are hereby disclosed.

The membrane 54 can be opposite a housing surface, opposite an insert surface, opposite a housing protrusion (not shown), opposite an insert protrusion (not shown), or any combination thereof. One or more housing and/or insert protrusions can extend at least partially toward a longitudinal center of the device flow channel 62 in the housing 14, for example, toward a longitudinal center of the flow path defined by the housing conduit 56. The occluder 32 can be configured to engage the one or more protrusions when the movable sensor 18 is in a closed configuration.

FIG. 3B further illustrates that the device 10 can have a housing opening 70 (also referred to as a housing window). The housing opening 70 can be on a device first, second, third, fourth, fifth, or sixth side, or any combination thereof. The orientation of these various sides is discussed above with reference to the sensor 18. For example, FIG. 3B illustrates that the housing opening 70 can be on the device first side 10c. The device first side 10c can be a bottom side of the device, for example, relative to when the device is in the attached configuration, where the bottom of the device 10 is the skin contact side of the device 10.

The housing opening 70 can have, for example, a circular, a polygonal (triangular, rectangular), a stadium, or an irregular shape. The housing opening 70 can be a hole (also referred to as a passageway) in a wall of the housing 14.

The housing opening 70 can have a housing opening longitudinal dimension 72 (also referred to as a housing opening first dimension). The housing opening longitudinal dimension 72 can range from about 2 mm to about 40 mm, including every 1 mm increment within this range (e.g., 10 mm). The housing opening longitudinal dimension 72 can be the maximum longitudinal dimension of the housing opening 70, for example, along an axis parallel to or at an angle with the device longitudinal axis A1.

Although not shown in FIG. 3B, the housing opening 70 can also have a housing opening first transverse dimension (also referred to as a housing opening second dimension). The housing opening first transverse dimension can range from about 2 mm to about 40 mm, including every 1 mm increment within this range (e.g., 10 mm). The housing opening first transverse dimension can be the maximum transverse dimension of the housing opening 70, for example, along an axis parallel to or at an angle with the device second transverse axis A3.

Although not shown in FIG. 3B, the housing opening 70 can also have a housing opening second transverse dimension (also referred to as a housing opening third dimension). The housing opening second transverse dimension can range from about 0.5 mm to about 10 mm, including every 0.1 mm increment within this range (e.g., 1.0 mm, 2.0 mm). The housing opening second transverse dimension can be the maximum transverse dimension of the housing opening 70, for example, along an axis parallel to or at an angle with the device first transverse axis A2. The housing opening second transverse dimension can correspond to the depth of the hole 70.

The housing opening first, second, and third dimensions can correspond to length, width, and height dimensions of a housing hole (e.g., hole 70), respectively. As another example, the housing opening first and second dimensions can be a housing opening radius dimension, and the housing opening third dimension can be the depth of the hole 70 (e.g., where the hole 70 is cylindrical).

The housing opening 70 can have a housing opening surface area. The housing opening surface area can be the area of the void defined by the housing opening 70. For example, the area of the void can be defined by a plane parallel to the plane defined by axes A1 and A3, or any other combination of axes A1, A2, and A3. The housing opening surface area can be, for example, 4 $mm^2$ to about 1,600 $mm^2$ or more, including every 1 $mm^2$ increment within this range (e.g., less than 25 $mm^2$, less than 50 $mm^2$, less than 100 $mm^2$, less than 200 $mm^2$, less than 500 $mm^2$).

The housing opening surface area can be less than a surface area of a housing surface. For example, the housing opening surface area can be a percentage of a surface area of a housing surface. The percentage can range, for example, from about 1% to about 90%, including every 1% increment within this range (e.g., less than 50%, less than 25%, less than 10%, less than 5%, 20%, 15%, 10%, 5%). The housing surface having the area that the area of the housing opening 70 is compared against can be on the same or a different side of the device 10 as the housing opening 70. For example, the housing surface can be on the device first side 10c (e.g., a bottom surface of the housing), the device second side 10d (e.g., a top surface of the housing), or another device side. When the two areas being calculated are on the same surface (e.g., bottom housing surface), the surface area of the hole 70 can be ignored or observed when calculating the surface area of the housing surface. For example, for a square bottom surface having a surface area of 900 $mm^2$ and a hole 70 having an opening surface area of 100 $mm^2$, the surface area of the bottom surface can be considered to be 1,000 $mm^2$ (hole 70 ignored) or 900 $mm^2$ (hole 70 observed) such that the housing opening surface area is about 10.0% (hole 70 ignored) or about 11.1% (hole 70 observed) of the surface area of the bottom surface. Another way of quantifying this is by stating that the housing opening surface area can be smaller than a housing surface through which the housing opening 70 extends. For example, the housing opening 70 that extends through a housing surface of the device 10 can have a housing opening surface area that is about 100 or more times smaller than the surface area of the housing surface through which the housing opening 70 extends, or more narrowly, about 50 or more times smaller, or more narrowly, about 25 or more times smaller, or more narrowly, about 10 or more times smaller (e.g., 14 times smaller, 10 times smaller, 5 times smaller).

Having a housing opening 70 with a size smaller than that of the size of the housing surface through which the housing opening 70 extends (e.g., a bottom surface or a skin contact surface of the device 10) can desirably allow the housing 14 to have a larger surface area to contact tissue which can be more comfortable for patients when the device is taped to their skin since the larger device surface area can more equally distribute the force of the device 10 against the skin, thereby being less likely to "dig" into tissue or leave an sensitive skin impression or indent after removal. This can be especially beneficial for patients undergoing hemodialysis treatment since the device 10 can be attached to their skin for hours at a time, for example, about 3 hours to about 6 hours. A small housing opening 70 can also allow the housing 14 to maintain a more secure seal around the device flow path 62 in the housing 14, for example, around the housing conduit 56, than if the housing space 51 were exposed by a large hole.

However, in some variations, the hole 70 can be larger than the than that of the size of the housing surface through which the housing opening 70 extends (e.g., opposite from the "less than" and "smaller" ratios/relationships above). In such variations, for a housing surface configured to contact skin, for example, a housing bottom surface, the hole 70 can be so large that the housing bottom surface can be an annular flange extending around the perimeter of the housing 14. For larger openings 70, the opening 70 can be a housing recess such that only a portion of the opening extends through a housing wall and exposes the housing space 51. Having such "larger" opening hole 70 sizes can be useful to lift the housing conduit 56 further away from the skin when attached to the patient. Where the opening hole 70 forms a large recess, a skin warming or cooling pack can be inserted in the recess and be in contact with the patient's skin during treatment to increase patient comfort. Such warm and cold packs can also help control vasodilation and vasoconstriction should such control be needed or helpful for the particular patient at hand.

The housing opening 70 can advantageously give the flow restrictor 28 access to the housing conduit 56 while maintaining a fluid tight seal between the tube 8 and the tip of the needle 12. The flow restrictor 28 can move within or through the housing opening 70, for example, to deform the membrane 54 to occlude flow through the housing conduit 56.

For example, the housing opening 70 can expose the membrane 54 by creating a passageway through a housing wall (e.g., a housing wall having an outer surface configured to contact skin). The housing opening 70 can open toward (e.g., face toward) the non-device surface (also referred to as the non-sensor surface and skin) when the sensor 18 is in the open configuration and the device 10 is attached to the non-device surface. The membrane 54 can be closer to the device longitudinal axis A1 than the housing opening 70. The membrane 54 can be closer to the longitudinal axis of the device flow path 62 than the housing opening 70. Some or all the membrane 54 can be in the housing opening 70. At least a portion of the membrane 54 can be attached to or integrated with an edge or surface defining the housing opening 70.

Some or all of the flow restrictor 28 can be in the housing opening 70 when the device 10 is in an attached configuration (also referred to as when the sensor 18 is in an open configuration). For example, at least a portion of the flow restrictor 28 can be in an opening plane defined between edges or surfaces of the housing opening 70. The opening plane can be, for example, a plane parallel to the plane defined by axes A1 and A3, or any other combination of axes A1, A2, and A3. For example, FIG. 3B illustrates that the occluder 32 can be in the housing opening 70 when the device 10 is in the attached configuration. Although not shown, a portion of the occluder arm 30 can also extend into the housing opening 70 when the device 10 is in an attached configuration.

FIG. 3B further illustrates that a portion of the occluder 32 (e.g., the tip of the occluder 32) can be in the housing 14 (e.g., in housing space 51) when the device 10 is in an attached configuration, for example, by extending past the housing opening 70 (e.g., past an inner opening plane of the opening window 70, where the inner opening plane can be defined between edges or surfaces that comprise interior edges, surfaces, or boundaries of the housing 14). Although not shown, a portion of the occluder arm 30 can also extend into the housing 14 (e.g., in housing space 51) when the device 10 is in an attached configuration.

FIG. 3B further illustrates that the tip of the occluder 32 can be in contact with the membrane 54 when the device 10 is in an attached configuration. Contact from the occluder 32 (e.g., the occluder tip) may or may not deform the membrane 54 when the sensor 18 is in an open configuration. For example, the occluder 32 in FIG. 3B is shown contacting but not deforming the membrane 54 when the sensor 18 is in an open configuration. However, in other variations, the occluder tip can deform the membrane 54 or can be spaced apart from the membrane 54 with a gap when the when the sensor 18 is in an open configuration. Such a deformation or gap can have a deformation/gap dimension of about 0.5 mm to about 2.5 mm, including every 0.1 mm increment within this range. The deformation/gap dimension can be measured along an axis parallel to or at an angle with a device axis such as axis A1, A2, or A3. For example, FIG. 3B illustrates that the deformation/gap dimension can be measured along an axis parallel to the device first transverse axis A2.

In variations where the occluder tip deforms the membrane 54 when the sensor 18 is in an open configuration, the inner surface of the membrane 54 that defines the housing conduit 56 can be deformed by the deformation dimension (e.g., by about 0.5 mm to about 2.5 mm or more) toward a housing surface opposite the occluder 32, toward a surface of the housing conduit 56 opposite the occluder 32, toward the device longitudinal axis A1, toward a longitudinal axis of the fluid conduit 56, or any combination thereof.

In variations where there is a gap between the occluder tip and the membrane 54 when the sensor 18 is in an open configuration, the gap dimension (e.g., about 0.5 mm to about 2.5 mm or more) can be measured between an outer surface of the membrane 54 (e.g., facing away from the housing space 51) and the occluder tip.

The occluder 32 can be attached to or integrated with the membrane 54. The occluder 32 can float relative to the membrane 54 such that the occluder 32 is not permanently attached to the membrane 54.

The occluder arm 30 can be in or outside of the housing space 51 when the device 10 is in an attached configuration. The occluder arm 30 can be in or outside of the housing window 70 when the device 10 is in an attached configuration. For example, FIG. 3B illustrates that the occluder arm 30 can be outside of (e.g., below) the housing opening 70 (e.g., below an outer opening plane of the housing window 70, where the outer opening plane can be defined between edges or surfaces that comprise outer edges, surfaces, or boundaries of the housing 14, for example, those edges surfaces or boundaries that are farther from the device longitudinal axis A1 than the edges, surfaces or boundaries associated with the inner opening plane of the housing window 70).

FIG. 3B further illustrates that the occluder arm 30 can extend over some or all of the housing opening 70 when the device 10 is in an attached configuration. The occluder arm 30 can extend along, for example, about 10% to about 90% of the housing opening longitudinal dimension 72. For example, where the housing opening longitudinal dimension 72 is 10 mm and the occluder arm 30 extends over 75% of the housing opening longitudinal dimension, the occluder arm 30 can extend 7.5 mm over the housing opening 70 along the housing opening longitudinal dimension 72 when the device 10 is in an attached configuration.

FIG. 3B further illustrates that when the sensor 18 is in an open configuration, the occluder axis A9 can be at an occluder angle of about 30 degrees to about 150 degrees relative to the device longitudinal axis A1. For example, FIG. 3B illustrates that the occluder angle can be 90 degrees, or perpendicular to the device longitudinal axis A1. Occluder angles less than 90 degrees can correspond to where the occluder 32 extends at least partially in a longitudinal direction toward the device distal end 10b or the sensor distal end 18b when the sensor 18 is in an open configuration. Occluder angles greater than 90 degrees can correspond to where the occluder 32 extends at least partially in a longitudinal direction toward the device proximal end 10a or the sensor proximal end 18a when the sensor 18 is in an open configuration.

Although not illustrated in FIG. 3B, the flow path defined by the housing conduit 56 can have one or more tapers. For example, the flow path defined by the channel occlusion region 68 can be tapered from a first transverse cross-sectional area to a second transverse cross-sectional area less than the first cross-sectional area, for example, such that the tapered region of the channel occlusion region 68 forms a frusto-conical shaped flow path. The outer surface of the conduit defining the tapered flow path (e.g., housing conduit 56) may or may not have a corresponding taper as well. The first transverse cross-sectional area can be closer to the proximal end of the device flow channel 62 than the second transverse cross-sectional area. The flow path can be tapered so that it can be easier or take less force to occlude the flow path with spring action of the flow restrictor 28. For example, the occluder 32 can be configured to deform the membrane 54 at the location of the second transverse cross-sectional of the channel occlusion region. As another example, the occluder 32 can be configured to deform the membrane 54 about 1 mm to about 20 mm longitudinally away from the location of the second transverse cross-sectional in a direction toward the distal end of the device flow path 62, including every 1 mm increment within this range (e.g., 5 mm, 10 mm). The membrane 54 can define some or all of the taper. The first cross-sectional area can be within or outside of the channel occlusion region 68.

As another example, the foregoing taper can be a first taper, and the flow path defined by the housing conduit 56 can have a second taper. For example, the flow path defined by the channel occlusion region 68 can be tapered from the second transverse cross-sectional area to a third transverse cross-sectional area greater than the second cross-sectional area, for example, such that the tapered region of the channel occlusion region 68 forms a second frusto-conical shaped flow path. The first and third transverse cross-sectional areas can have the same or different cross-sectional areas as each other. The outer surface of the conduit defining the second tapered flow path (e.g., housing conduit 56) may or may not have a corresponding taper as well. The second transverse cross-sectional area can be closer to the proximal end of the device flow channel 62 than the third transverse cross-sectional area. The second frusto-conical shaped flow path can be a mirror image the frusto-conical shaped flow path between the first and second transverse cross-sectional areas (also referred to as the first frusto-conical shaped flow path), for example, as reflected across the second transverse cross-sectional area. The first cross-sectional area can be within or outside of the channel occlusion region 68. As yet another example, the second transverse cross-sectional area between the first and third transverse cross-sectional areas can be elongated such that a channel having a constant, a less tapered, or more tapered cross flow path can extend between the first and second tapered flow paths (e.g., between the first and second frusto-conical shaped flow paths). This elongated channel can desirably give the occluder 32 a smaller cross-sectional area to partially or fully occlude.

FIGS. 4A and 4B illustrate the device 10 in a variation of an occluded configuration as described above with reference to FIG. 1.

FIGS. 4A and 4B further illustrate that the device 10 can change from an attached configuration with the sensor 18 in an open position to an occluded configuration with the sensor 18 in a closed position when the external force 80 is reduced or entirely removed from the sensor first contact surface 48, for example, as shown by arrow 82. FIGS. 4A and 4B also illustrate the external force 80 to show a variation of an external force that can be applied to the sensor first contact surface 48 of the device 10 to change the shape of the device 10 from an occluded configuration with the sensor 18 in a closed position to an attached configuration with the sensor 18 in an open position. The external force 80 illustrated in FIGS. 4A and 4B is not being applied to the device 10. In other variations, the force 80 is being applied to the device 10 in FIGS. 4A and 4B but with a magnitude that is less than that of the magnitude shown in FIGS. 3A and 3B, for example as shown coupled with the reduction or elimination of force arrow 82.

FIGS. 4A and 4B further illustrate that the pre-attached and dislodged configurations of the device 10 can be the same. However, the pre-attached and dislodged configurations can also be different from each other.

FIGS. 4A and 4B further illustrate that the sensor distal end 18b can move (e.g., arrow 84) away from the device longitudinal axis A1 when the external force 80 is reduced (e.g., arrow 82) or eliminated (e.g., arrow 82). The sensor distal end 18b can rotate and/or translate relative to the device longitudinal axis A1. For example, the sensor distal end 18b can rotate (e.g., arrow 84) away from the device longitudinal axis A1 when the external force 80 is reduced (e.g., arrow 82) or eliminated (e.g., arrow 82).

FIG. 4B further illustrates that the flow restrictor 28 can move (e.g., arrow 86) toward a housing surface opposite the occluder 32, toward a surface of the housing conduit 56 opposite the occluder 32, toward the device longitudinal axis A1, toward a longitudinal axis of the fluid conduit 56, or any combination thereof. The flow restrictor 28 can rotate and/or translate relative to any of these features. For example, FIG. 4B illustrates that the occluder 32 can rotate (e.g., arrow 86) toward a housing surface opposite the occluder 32, toward a surface of the housing conduit 56 opposite the occluder 32, toward the device longitudinal axis A1, toward a longitudinal axis of the fluid conduit 56, or any combination thereof.

The occluder 32 can move (e.g., arrow 86) into the device flow path 62, for example, in the channel occlusion region 68. Some of the occluder 32 (e.g., the tip of the occluder 32) can rotate past the device longitudinal axis A1. FIG. 4B illustrates that the occluder 32 can pierce the membrane 54 and rotate directly into the flow path to partially or fully occlude flow through the device flow channel 62 when the device 10 is in a dislodged configuration. The membrane 54 can self-seal around the base of the occluder (e.g., the occluder portion in contact with the membrane) such that fluid does not flow through the opening in the membrane 54. The membrane 54 can reseal against itself if the occluder 32 is removed from the flow path 62 and membrane 54, for example, if the device 10 is reattached to the skin.

FIG. 4B further illustrates that the sensor second longitudinal axis A7 can be at an angle relative to the device longitudinal axis A1 of about 10 degrees to about 75 degrees when the device 10 is in a non-attached configuration, including every 1 degree increment within this range (e.g., 30 degrees, 40 degrees, 50 degrees). In such variations, FIG. 4B illustrates that a portion of the sensor distal end 18b (e.g., the sensor distal end first section 20a) can extend at least partially in a longitudinal direction toward device distal end 10b and at least partially in a transverse direction away from the device longitudinal axis A1 when the device 10 is in a non-attached configuration. The sensor axis A7 can return to a parallel or less angled orientation relative to axis A1 when an external force (e.g., arrow 80) is applied to the sensor 18.

FIG. 4B further illustrates that the sensor first transverse axis A8 can be at an angle relative to the device longitudinal axis A1 of about 10 degrees to about 75 degrees when the device 10 is in a non-attached configuration, including every 1 degree increment within this range (e.g., 30 degrees, 40 degrees, 50 degrees). In such variations, FIG. 4B illustrates that a portion of the sensor distal end 18b (e.g., the sensor distal end second section 20b) can extend at least partially in a longitudinal direction toward device distal end 10b and at least partially in a transverse direction toward the device longitudinal axis A1 when the device 10 is in a non-attached configuration. The sensor distal end second section 20b can also extend at least partially in a longitudinal direction toward the device distal end 10 and/or toward the device proximal end 10a when the device 10 is in a non-attached configuration. The sensor axis A8 can return to a perpendicular or less angled orientation relative to axis A1 when an external force (e.g., arrow 80) is applied to the sensor 18.

FIG. 4B further illustrates that when the sensor 18 is in a closed configuration, the occluder axis A9 can be at an occluder angle of about 30 degrees to about 150 degrees relative to the device longitudinal axis A1. For example, FIG. 4B illustrates that the occluder angle can be about 50 degrees, about 60 degrees, or about 70 degrees relative to the device longitudinal axis A1. In such variations, FIG. 4B illustrates that the occluder 32 can extend at least partially in a longitudinal direction toward device distal end 10b and at least partially in a transverse direction away from the device longitudinal axis A1 when the device 10 is in a non-attached configuration. The sensor axis A9 can return to a perpendicular or less angled orientation relative to axis A1 when an external force (e.g., arrow 80) is applied to the sensor 18.

FIG. 4B further illustrates that the sensor distal terminal end 24 can be a dimension 90 away from the device longitudinal axis A1 when the sensor 18 is in a closed position. The dimension 90 can be measured along an axis perpendicular to the device longitudinal axis A1 and can range from about 1 mm to about 30 mm, including every 1 mm increment within this range (e.g., 5 mm, 10 mm, 15 mm). The dimension 90 can be the maximum dimension that the distal terminal end 24 can be from the device longitudinal axis A1 when the sensor 18 is in a closed configuration.

FIG. 4C illustrates that the device 10 can be partially occluded when the sensor 18 is in a closed position. For example, FIG. 4C illustrates that there can be a gap 92 between the occluder 32 a surface of the housing conduit 56 (e.g., a surface of the insert 17, a surface of the housing 14). The gap 92 can have a dimension of about 0.1 mm to about 2.0 mm or more, including every 0.1 mm increment within this range (e.g., 0.8 mm, 1.0 mm), for example, as measured along axis A11 between the occluder 32 and a surface defining the housing conduit 56. Axis A11 can be perpendicular to the device longitudinal axis A1.

FIG. 4C further illustrates that the device 10 can restrict fluid flow through the device channel 62 by decreasing a channel cross-sectional area from a first cross-sectional area (e.g., FIG. 3B) to a second cross-sectional area (e.g., FIG. 4B) less than the first cross-sectional area. The second cross-sectional area can be about 1% to about 100% less than the first cross-sectional area, including every 1% increment within this range, where 100% can correspond to complete blockage of the channel in one or multiple channel cross-sections. For example, FIG. 3B illustrates that the first cross-sectional area can be completely non-occluded, and FIG. 4C illustrates that the second cross-sectional area can be between about 80% to about 95% smaller relative to the first cross-sectional area, including every 1% increment within this range (e.g., 90%, 95%). The first cross-sectional area can correspond to the cross-section of the flow path when the device 10 is in an attached configuration and the second cross sectional area can correspond to when the device 10 is in a non-attached configuration (e.g., a dislodged configuration).

The flow restrictor configuration in FIG. 4C can be a default configuration of the flow restrictor 28. For example, the spring 26 can be biased to move the occluder 32 and the occluder arm 30 into the positions shown in FIG. 4C when no external force (e.g., force 80) is applied to the sensor 18 (e.g., to the sensor distal end 18b). In other variations, the flow restrictor configuration in FIG. 4C can correspond to when an external force (e.g., force 80) has been reduced (e.g., arrow 82) but not completely removed from the sensor first contact surface 48. The device 10 can still occlude about 80% to about 95% of the flow path 56 and effectively help the patient by reducing fluid loss or delivery in such partial dislodgement scenarios.

Figure 4D:
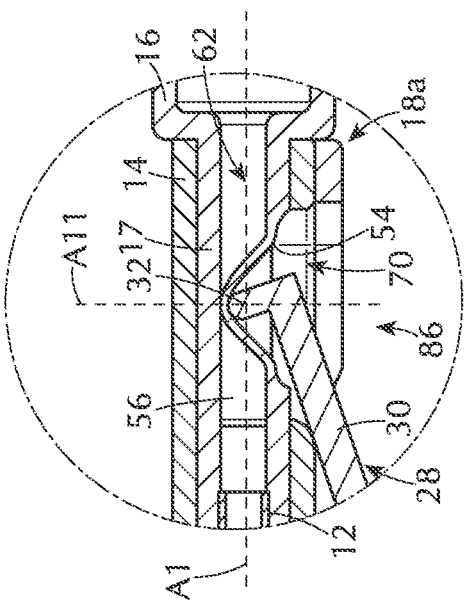
FIG. 4D illustrates another variation of the occluded configuration of the tissue access device of FIG. 4B at section 4C-4C.

FIG. 4D illustrates that the flow restrictor 28 can fully occlude the housing conduit 56, for example, by moving (via the spring 26) the occluder 32 further into the flow path 56 during occlusion of the device 10. In such variations, the second cross-sectional area can be about 100% relative to a first cross sectional area.

The flow restrictor configuration in FIG. 4D can be a default configuration of the flow restrictor 28. For example, the spring 26 can be biased to move the occluder 32 and the occluder arm 30 into the positions shown in FIG. 4D when no external force (e.g., force 80) is applied to the sensor 18 (e.g., to the sensor distal end 18b).

FIGS. 4C and 4D illustrate that the occluder 32 can pierce and reseal around the membrane 54 when the sensor is in the closed position. The pierce point is shown as element 94.

Figure 4E:
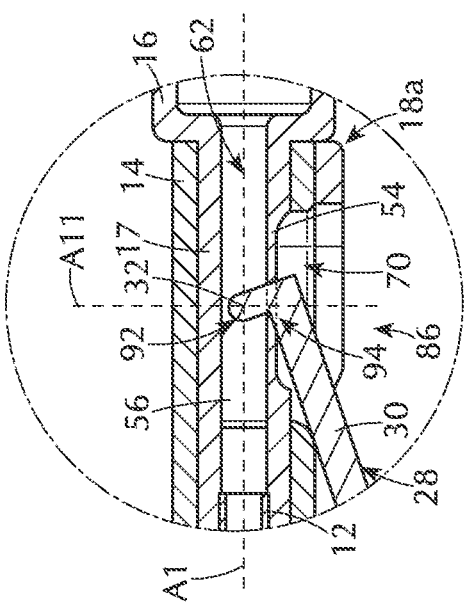
FIG. 4E illustrates another variation of the occluded configuration of the tissue access device of FIG. 3B at section 4C-4C.

FIG. 4E illustrates that the flow restrictor 28 (e.g., the occluder 32 and/or the occluder arm 30) can deflect the membrane 54 into the housing conduit 56 to occlude flow through the device 10, for example, in a direction away from the window 70. The occluder 32 can deflect the membrane 54 into the housing conduit 56 during occlusion of the device 10. The gap 92 can have a dimension of about 0.1 mm to about 2.0 mm or more, including every 0.1 mm increment within this range (e.g., 0.8 mm, 1.0 mm), for example, as measured along axis A11 between the occluder 32 and a surface defining the housing conduit 56 (e.g., a surface of the insert 17 and/or a surface of the housing 14). Axis A11 can be perpendicular to the device longitudinal axis A1. With the gap 92, FIG. 4E illustrates that the second cross-sectional area can be between about 80% to about 95% smaller relative to the first cross-sectional area (e.g., FIG. 3B), including every 1% increment within this range (e.g., 90%, 95%).

The flow restrictor configuration in FIG. 4E can be a default configuration of the flow restrictor 28. For example, the spring 26 can be biased to move the occluder 32 and the occluder arm 30 into the positions shown in FIG. 4E and deform the membrane 54 into the housing conduit 56 when no external force (e.g., force 80) is applied to the sensor 18 (e.g., to the sensor distal end 18b). In other variations, the flow restrictor configuration in FIG. 4E can correspond to when an external force (e.g., force 80) has been reduced (e.g., arrow 82) but not completely removed from the sensor first contact surface 48. The device 10 can still occlude about 80% to about 95% of the flow path 56 and effectively help the patient by reducing fluid loss or delivery in partial dislodgement scenarios.

Figure 4F:
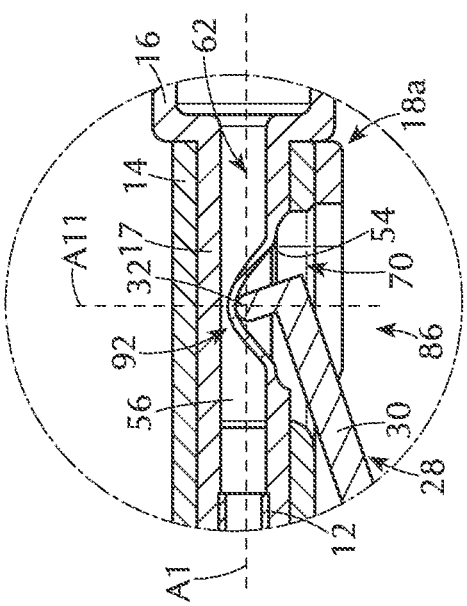
FIG. 4F illustrates another variation of the occluded configuration of the tissue access device of FIG. 3B at section 4C-4C.

FIG. 4F illustrates that the flow restrictor 28 (e.g., the occluder 32 and/or the occluder arm 30) can fully occlude the housing conduit 56, for example, by moving (via the spring 26) the occluder and membrane 32, 54 further into the flow path 56. The membrane 54 and the occluder 32 (e.g., on the proximal side of the sensor 18) is shown fully pressed into the flow path 56, for example, via the spring 26. For example, the force to push this member upward can come from the curved spring region portion of the central part of the sensor 18. A portion (e.g., an apex) of the membrane 54 in the deformed configuration can contact a surface that defines at least a portion of the housing conduit (e.g., a surface of the insert 17 and/or a surface of the housing 14) when the sensor 18 is in a closed position. When the occluder 32 pushes the membrane 54 into contact with another surface, the second cross-sectional area can be about 100% less than the first cross sectional area such that the housing conduit 56 is fully occluded.

The flow restrictor configuration in FIG. 4F can be a default configuration of the flow restrictor 28. For example, the spring 26 can be biased to move the occluder 32 and the occluder arm 30 into the positions shown in FIG. 4F when no external force (e.g., force 80) is applied to the sensor 18 (e.g., to the sensor distal end 18b).

The spring 26 can have a spring constant k such that the weight of the device 10 is configured to be insufficient to move the sensor 18 from a closed position to a partially open or a fully open position. This feature can prevent further fluid loss should the device 10 become dislodged and fall onto a surface (e.g., a floor or a patient's lap) and land such that the device is resting on the flow restrictor 28 (e.g., resting on the sensor distal end 18b).

FIGS. 3A and 4A illustrate that the spring 26 can be outside of the housing 14 when the sensor is in an open configuration and in a closed configuration, respectively. For example, when the device 10 is in an attached configuration, the spring 26 can be between the housing 14 and the skin, and when the device 10 is in a pre-attached or dislodged configuration, the spring 26 can be between the housing and the environment. In other variations, some or all of the spring can be inside the housing 14 when the device 10 is in the attached configuration and/or when the device 10 is in the pre-attached or dislodged configuration. FIGS. 3A and 3B further illustrate that that a first end of the spring 26 (e.g., the end of the spring closer to the device proximal end 10a) can be closer to the device longitudinal axis A1 when the device 10 is in an attached configuration (e.g., FIG. 3A) than when the device 10 is in a pre-attached or dislodged configuration (e.g., FIG. 4A).

FIGS. 3A-4B illustrate that the sensor distal end first section 20a can extend parallel to the device longitudinal axis A1 when the device is in an attached configuration (e.g., FIGS. 3A and 3B) and away from the device longitudinal axis A1 when the device 10 is in a pre-attached or dislodged configuration (e.g., FIGS. 4A and 4B). As another example, the sensor distal end first section 20a can extend more away from the device longitudinal axis A1 when the device 10 is in a pre-attached or dislodged configuration than when the device 10 is in an attached configuration (e.g., by about 5 degrees to about 60 degrees more, including every 1 degree increment within this range).

FIGS. 3A-4B illustrate that the sensor distal end second section 20b can extend parallel to the device first transverse axis A2 when the device is in an attached configuration (e.g., FIGS. 3A and 3B) and away from the device first transverse axis A2 when the device 10 is in a pre-attached or dislodged configuration (e.g., FIGS. 4A and 4B). As another example, the sensor distal end second section 20b can extend more away from the device first transverse axis A1 when the device 10 is in a pre-attached or dislodged configuration than when the device 10 is in an attached configuration (e.g., by about 5 degrees to about 60 degrees more, including every 1 degree increment within this range).

FIGS. 3A-4B illustrate that the sensor distal end 18b (e.g., the needle over insertion barrier 20b) can be closer to a longitudinal access of the needle 12 when the device 10 is in an attached configuration (e.g., FIGS. 3A and 3B) than when the device 10 is in a pre-attached or dislodged configuration (e.g., FIGS. 4A and 4B). FIGS. 3A-4B further illustrate that the sensor distal end 18b (e.g., the needle over insertion barrier 20b) can be closer to the tip of the needle 12 or to a device distal end 10b when the device 10 is in an attached configuration (e.g., FIG. 3A) than when the device 10 is in a pre-attached or dislodged configuration (e.g., FIG. 4A).

FIGS. 3A-4B illustrate that a needle over insertion barrier (e.g., section 20b) can be closer to a longitudinal access of the needle 12 when the device 10 is in an attached configuration (e.g., FIGS. 3A and 3B) than when the device 10 is in a pre-attached or dislodged configuration (e.g., FIGS. 4A and 4B). FIGS. 3A-4B further illustrate that a needle over insertion barrier (e.g., section 20b) can be closer to the tip of the needle 12 or to a device distal end 10b when the device 10 is in an attached configuration (e.g., FIG. 3A) than when the device 10 is in a pre-attached or dislodged configuration (e.g., FIG. 4A). Additionally or alternatively, the device 10 can have an over insertion barrier that remains in a fixed position when the sensor 18 moves between open and closed configurations. For example, the device 10 can have an over insertion barrier attached to or integrated with the housing 14 and/or the needle hub 13 as described above.

FIGS. 3A-4B illustrate that the sensor 18 (e.g., movable footplate) has a sensor first configuration when the sensor first contact surface 48 applies a first force to a non-sensor surface (e.g., skin) and a sensor second configuration when the sensor first contact surface 48 applies a second force less than the first force to the non-sensor surface. The spring 26 can be biased to move the movable sensor 18 from the sensor first configuration to the sensor second configuration when the force applied by the sensor first contact surface 48 against the non-sensor surface changes from the first force to the second force. As another example, the spring 26 can be biased to move the sensor 18 from the sensor first configuration to the sensor second configuration when the first force decreases to the second force. The second force can be 0 Newtons.

At least a first portion of the occluder 32 can occlude the housing conduit 56 when the movable sensor 18 is in the sensor second configuration. At least a second portion of the occluder 32 can be in the housing opening 70 when the movable sensor 18 is in the sensor second configuration and outside the housing opening 70 when the movable sensor 18 is in the sensor first configuration.

The sensor distal end 18b can have a barrier configured to prevent over insertion of the needle 12 into tissue (e.g., into a vessel). At least a portion of the barrier can be closer to the needle 12 when the movable sensor 18 is in the sensor first configuration than when the movable sensor 18 is in the sensor second configuration. At least a portion of the barrier can abut or be next to a side of the needle 12 when the movable sensor 18 is in the sensor first configuration. At least a portion of the barrier can be closer to the needle 12 when the movable sensor 18 is in the sensor first configuration than when the movable sensor 18 is in the sensor second configuration The sensor distal end 18b can have a curved surface (e.g., curved surface 21) configured to reduce friction against the non-sensor surface when the needle 12 is inserted into tissue (e.g., into a vessel). At least a portion of the curved surface can be closer to the needle 12 when the movable sensor 18 is in the sensor first configuration than when the movable sensor 18 is in the sensor second configuration.

The occluder 32 can be configured to at least partly occlude the housing conduit 56 when the movable sensor 18 is in the sensor second configuration.

Flow through the housing conduit 56 can be about 1% to about 100% less when the movable sensor 18 is in the sensor second configuration than when the movable sensor 18 is in the sensor first configuration, including every 1% increment within this range (e.g., 80%, 90%, 95%, 97%, 100%).

A housing conduit cross-sectional area can be decreased by about 1% to about 100% when the movable sensor moves from the sensor first configuration to the sensor second configuration, including every 1% increment within this range (e.g., 80%, 90%, 95%, 97%, 100%).

The occluder 32 can be closer to a surface of the housing conduit 56 opposite the deformable membrane 54 when the movable sensor 18 is in the sensor second configuration than when the movable sensor is in the sensor first configuration. The spring 26 can be biased to move the occluder 32 closer to the surface of the housing conduit 56 when the movable sensor 18 moves from the sensor first configuration to the sensor second configuration The deformable membrane 54 can be deformed by the occluder 32 when the movable sensor 18 is in the sensor second configuration. A surface of the deformable membrane can be closer to a housing conduit surface when the movable sensor 18 is in the sensor second configuration than when the movable sensor 18 is in the sensor first configuration The deformable membrane 54 can be less deformed or deflected by the occluder 32 when the movable sensor 18 is in the sensor first configuration than when the movable sensor 18 is in the sensor second configuration.

The deformable membrane 54 may not deformed by the occluder 32 when the movable sensor 18 is in the sensor first configuration.

The sensor distal end 18*b* can be closer to the needle 12 and the housing conduit 56 when the movable sensor 18 is in the sensor first configuration than when the sensor 18 is in the sensor second configuration. The spring 26 can be biased to move the sensor distal end 18*b* away from the needle 12 and the housing conduit 56 when the movable sensor 18 moves from the sensor first configuration to the sensor second configuration.

The sensor distal end 18*b* (e.g., the sensor distal end second section 20*b*) can have a sensor opening 22. A portion of the needle 12 can be in the sensor opening 22 when the movable sensor 18 is in the sensor first configuration and outside the sensor opening 22 when the movable sensor 18 is in the sensor second configuration.

The sensor distal end 18*b* can have a barrier configured to prevent over insertion of the needle into a vessel.

At least a portion of the sensor proximal end 18*a* can extend along a direction parallel to the device longitudinal axis A1 when the movable sensor is in the sensor first and second configurations. At least a portion of the sensor distal end 18*b* can extend along a direction parallel to the device longitudinal axis A1 when the movable sensor 18 is in the sensor first configuration and a direction angled relative to the device longitudinal axis A1 when the movable sensor 18 is in the sensor second configuration The housing 14 can have a housing first side and a housing second side opposite the housing first side. The housing first side can be closer to the sensor first contact surface than the housing second side. The housing window 70 can be on the housing first side such that the housing window 70 faces toward the non-sensor surface (e.g., skin) when the movable sensor 18 is in the sensor first configuration.

The sensor 18 can have a sensor second contact surface 50. The sensor second contact surface 50 can be closer to the housing 14 when the movable sensor 18 is in the sensor first configuration than when the movable sensor 18 is in the sensor second configuration.

The device distal end 10*b* can be movable relative to the device proximal end 10*a*. For example, the device distal end 10*b* can be longitudinally and/or transversely movable along the device longitudinal axis A1 relative to the device proximal end 10.

The needle 12 can be longitudinally and/or transversely movable along the device longitudinal axis A1.

The needle 12 can be retractable into the housing 14 or into a needle channel adjacent the housing 14 such that the needle 12 has a non-retracted position and a retracted position. The needle distal end (e.g., the tissue cutting tip) can be closer to the housing proximal end 14*a* when the needle 12 is in the retracted position than when the needle 12 is in the non-retracted position.

At least a portion of the needle 12 can be outside the housing 14 or the needle channel adjacent the housing 14 in the non-retracted position and inside the housing 14 or the needle channel adjacent the housing 14 in the retracted position.

The needle distal end (e.g., the tissue cutting tip) can be the distal terminal end of the device 10 when the needle 12 is in at least one of the non-retracted position and the retracted position.

The needle 12 can be retracted by a user after the device becomes dislodged from an attached configuration.

The needle 12 can automatically retract when the device becomes dislodged from an attached configuration. For example, the sensor can be connected to the needle 12 (e.g., the base of the needle 12). The spring 26 can be biased to retract the needle 12 when the sensor changes from an open position to a closed position following initial insertion of the needle 12. The spring 26 can be connected to the needle with a link (not shown).

Figure 5:
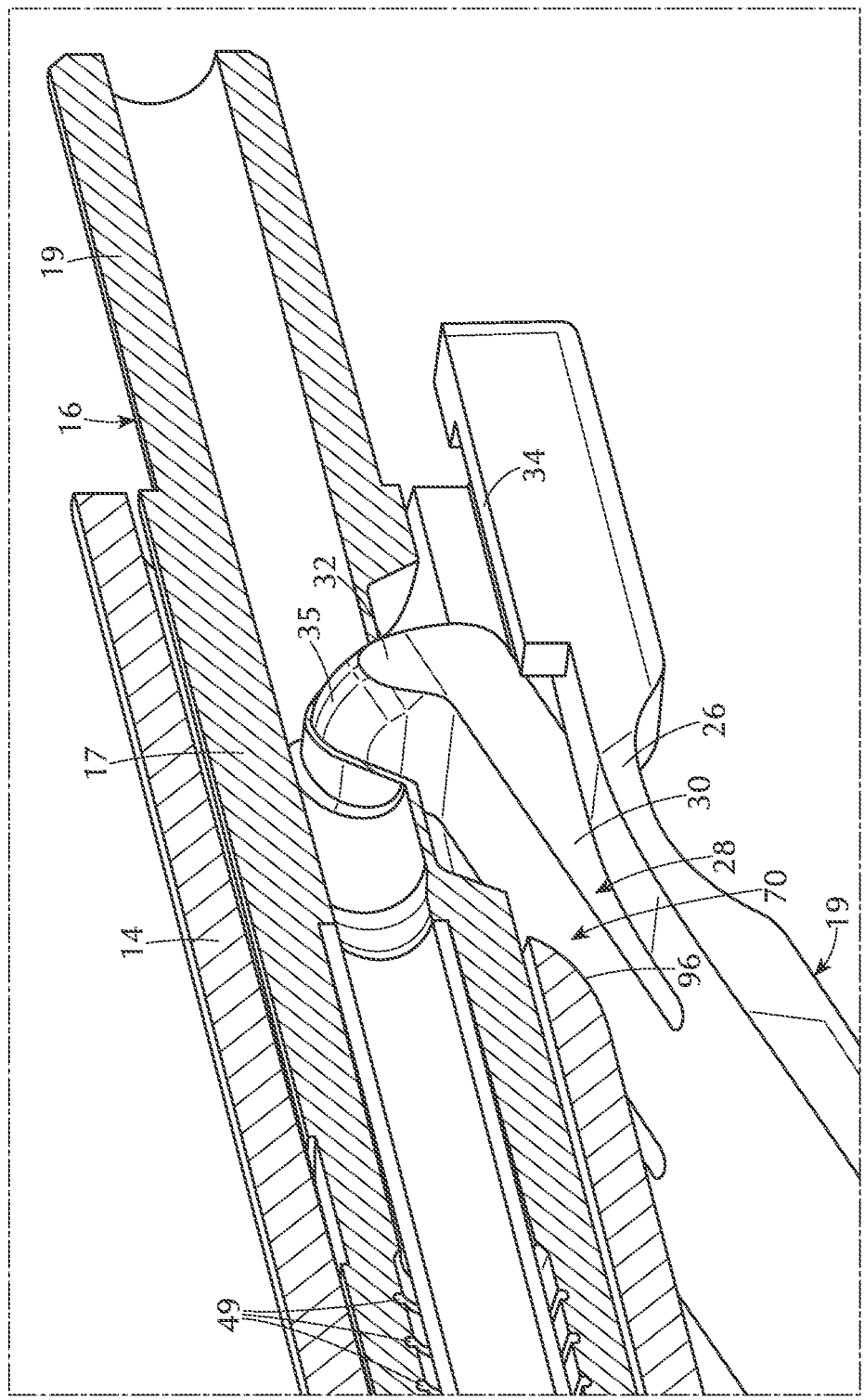
FIG. 5 is a magnified perspective view of the occluded configuration of the tissue access device of FIG. 4E.

FIG. 5 illustrates that a housing surface 96 defining the housing window 70 can be tapered to allow the occluding arm 30 to move the occluder 32 into to deflect the membrane 54 into the housing conduit 56 to occlude the device 10.

FIG. 5 further illustrates that the occluder 32 can have an occluder terminal end 35 having a curved surface configured not to puncture the membrane 54 when the sensor 18 is in a closed configuration.

FIG. 5 further illustrates that the connector 16 can comprise a nipple 19. The nipple 19 can be integrated with or attached to the insert 17. The tube 8 can be connected to the nipple 19.

Figure 6A:
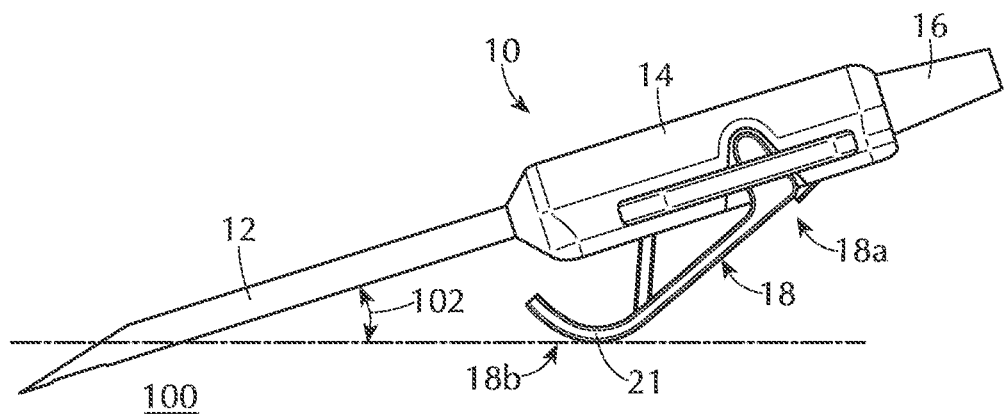
FIG. 6A illustrates a side view of a variation of a tissue access device being inserted into tissue and being dislodged tissue.
Figure 6B:
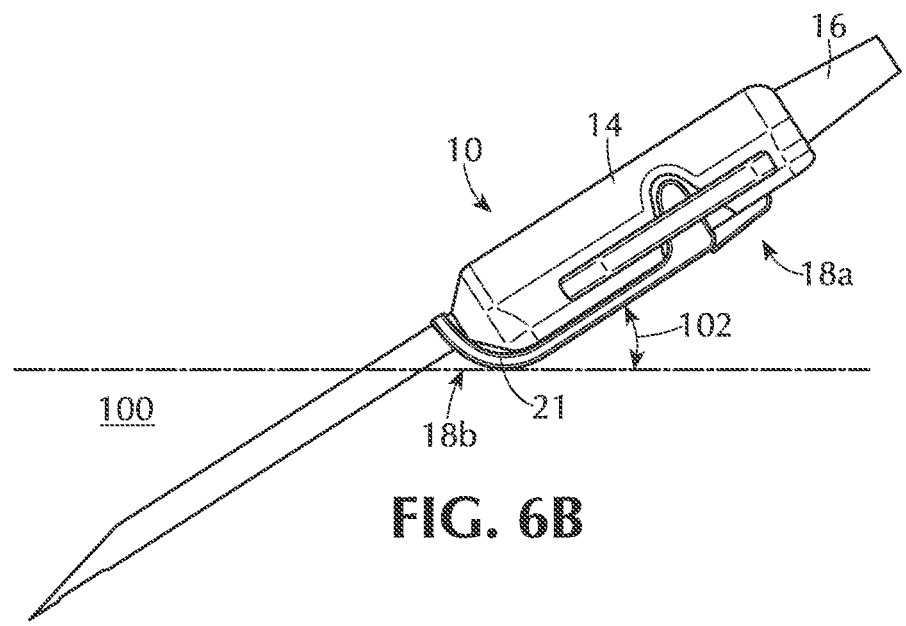
FIG. 6B illustrates the tissue access device of FIG. 6A inserted into tissue.

FIGS. 6A and 6B illustrate a variation of the device 10 being inserted into tissue 100 and being dislodged from the tissue 100. From FIG. 6A to FIG. 6B, the device 10 is shown being inserted into the tissue 100, with the sensor changing from a closed position (also referred to as an occluding position) to an open position (also referred to as a less occluding position). From FIG. 6B to FIG. 6A, the device 10 is shown becoming dislodged from the tissue 100, with the sensor 18 changing from an open position to a closed position.

FIG. 6A illustrates that the curved portion 21 (also referred to as a curved distal end) of the sensor 18 can reduce frictional forces against the skin 100 during insertion, thereby enabling the needle 12 to be inserted with less force and less possible injury to the patient. The curved end of the sensor 18 (e.g., sensor distal end 18*b*) can encourage a low friction insertion process. The device 10 is shown being inserted at an insertion angle 102 with respect to a patient skin surface 100. The insertion angle 102 can be, for example, from about 10 degrees to about 60 degrees, including every 1 degree increment within this range. For example, the insertion angle 102 can be a typical insertion angle of about 25 degrees, or between about 18 degrees and about 32 degrees.

FIG. 6A further illustrates that the curved distal end 18*b* (e.g., with curve 21) can also reduce frictional forces against the skin 100 during dislodgement.

FIG. 6B illustrates that the curved distal end 18*b* can enable the device 10 to maintain a mechanical interface with the skin 10 that can continue to hold the sensor 18 in check against the housing 14 and/or the needle 12 regardless of the insertion angle 102, thereby enhancing functionality of the dislodgement detection system. For example, FIG. 6B illustrates that the curved distal end 18*b* (e.g., with curve 21) can maintain the sensor 18 in an open position (also referred to as maintain the device in an attached configuration) after the needle 12 has been fully inserted and thus preserve dislodgement detection functionality of the sensor 18 even if the insertion angle 102 is as high as 50 degrees. FIG. 6B illustrates that the insertion angle can be 25 degrees for a "typical angle" insertion and can be up to about 50 degrees for a "high angle" insertion.

FIG. 6B further illustrates that the curved end of the sensor 18 can rest against the needle 12 and/or the needle hub 13 upon insertion, with the needle 12 protruding through the sensor opening 20 (e.g., a U-shaped opening) on the sensor distal end 18b.

FIG. 7 illustrates that the needle 12 can be retracted into the housing 14, for example, into the housing conduit channel 56.

FIG. 7A illustrates that the device 10 can have a pincher system 101. The pincher system 101 can have two or more external pinchers 104, for example, 2 to 8 external pinchers 104, including every 1 pincher increment within this range (e.g., 2 pinchers, 3 pinchers, 4 pinchers). For example, FIG. 7A illustrates that the device 10 can have an external first pincher 104a, an external second pincher 104b, an external third pincher 104c, or any combination thereof. The external pinchers 104 can be at the device proximal end 10a and/or define the device proximal end 10a. The external pinchers 104 can be integrated with or attached to the connector 16 or can be separate from the connector 16. The external pinchers 104 can be attached or integrated with the housing 14.

The pincher system 101 can be fixed. The pincher system 101 can be movable. For example, a movable pincher system 101 can swivel about the device longitudinal axis A1 and/or the longitudinal axis of the housing conduit 56. The pincher system 101 can swivel back and forth 360 degrees, or any less amount. For example, the pincher system 101 can swivel about 15 degrees to about 45 degrees clockwise and counterclockwise about the device longitudinal axis A1 and/or the longitudinal axis of the housing conduit 56 relative to the position shown in FIG. 7A, including every 1 degree increment within this range (e.g., 15 degrees, 30 degrees). The pincher system 101 can be mounted on a swivel joint. Additionally or alternatively, a movable pincher system 101 can be connected to the housing 14 with a flexible neck that can be configured to deflect under non-axial loads (e.g., relative to the device longitudinal axis A1). The flexible neck can be attached to or integrated with the housing 14 and/or with a base of the pincher system 101. As yet another example, a movable pincher system 101 can have external pinchers 104 that are flexibly attached at their base to the housing 14 such that in addition to or instead of a single flexible neck and/or a swivel joint, each external pincher 104 can be flexibly attached or integrated with the housing 14 at its respective base.

Figure 7B:
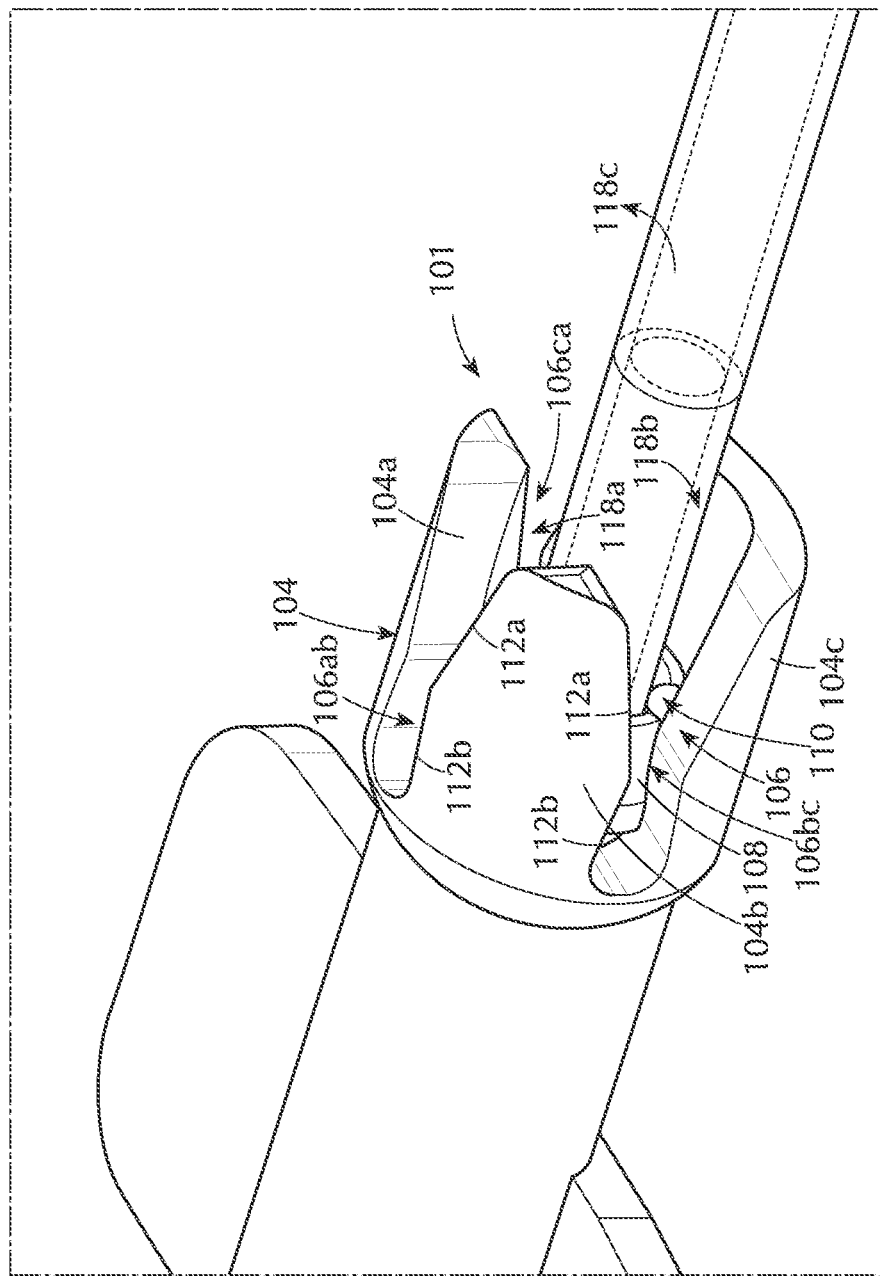
FIG. 7B is a magnified rear perspective view of the tissue access device of FIG. 7A.

The external pinchers 104 can be spaced apart along a perimeter a radial distance away from the tube 8 and/or along a perimeter of the pincher system 101. The perimeters can extend around the device longitudinal axis (e.g., axis A1). For example, the external pinchers 104 can be circumferentially spaced apart around the device longitudinal axis A1. The external pinchers 104 can be non-uniformly spaced apart around the perimeter of the tube 8 or the pincher system 101. For example, FIG. 7B illustrates that the first and second pinchers 104a, 104b can be spaced apart by about 90 degrees, as measured between the longitudinal centers of the pinchers 104a and 104b. The first and third pinchers 104a, 104c can be spaced apart by about 135 degrees, as measured between the longitudinal centers of the pinchers 104a and 104c. The second and third pinchers 104b, 104c can be spaced apart by about 135 degrees, as measured between the longitudinal centers of the pinchers 104b and 104c.

As another example, the external pinchers 104 can be uniformly spaced apart around the perimeter of the tube 8 or the pincher system 101. For example, the external first, second, and third pinchers 104a, 104b, 104c can be spaced about every 120 degrees around a circumference of the device longitudinal axis A1. When the spacing is equal and the perimeter is a circumference, the spacing angles can be determined by dividing 360 degrees by the number of external pinchers 104.

The external pinchers 104 can be configured to restrict or stop fluid flow through the tube 8 in the event of needle dislodgement after insertion. Dislodgement can occur before or after the device 10 has been taped to a patient's skin (e.g., skin 100).

FIG. 7A further illustrates that an external pinch space 106 (also referred to as external pinch gaps) can be defined between adjacent external pinchers 104 (e.g., between every pair of adjacent external pinchers 104). For example, the external first, second, and third pinchers 104a, 104b, 104c can define external first, second, and third pinch spaces 106ab, 106bc, and 106ca (not shown), respectively.

The external pinch gaps 106 can be spaced around the perimeter of the pincher system 101 by the same or different angles than the external pinchers. For example, FIG. 7B illustrates that the first and second external pinch gaps 106ab, 106bc can be spaced apart by about 90 degrees (or about a quarter of the perimeter of the system 101). The first and third external pinch gaps 106ab, 106ca can be spaced apart by about 90 degrees (or about a quarter of the perimeter of the system 101). The second and third external pinch gaps 106bc, 106ca can be spaced apart by about 180 degrees (or about half of the perimeter of the system 101).

The external pinchers 104 can be configured to restrict or stop fluid flow through the device 10 when the tube 8 is pushed or pulled (individually and collectively referred to as moved) in a non-axial direction, for example, in any direction away from the device longitudinal axis A1. When the tube 8 is moved in a non-axial direction, the tube 8 can be forced into an external pinch gap 106 such that the tube 8 is pinched partially or fully closed by a pair of external pinchers 104. The tube 8 can be pinched by compression pinch points optimized to pinch the tube 8 in the event the tubing 8 is pulled in a non-axial direction.

FIG. 7A further illustrates that the external pinchers 104 can have one or more tapered portions 112, for example, to help guide the tube 8 into the external pinch gaps 106 and/or to help retain the tube 8 within the external pinch gaps 106. For example, FIG. 7A illustrates that the external pinchers 104 can each have a tapered first portion 112a configured to guide the tube 8 into an external pinch gap 106, a tapered second portion 112b configured to retain the tube 8 in the external pinch gap 106, or any combination thereof. A taper inflection point 112c can be located between the tapered first and second portions 112a, 112b. The taper inflection 112c can be where the direction of the first taper of the tapered first portion 112a changes direction to the second taper of the tapered second portion 112b, or vice versa. At least part of the tapered first portion 112a can be on a proximal end of each external pincher 104 and at least part of the tapered second portion 112b can be on a distal end of each external pincher 104.

When the pincher system 101 can swivel, the external pinchers 104 can collectively swivel and help guide the tube 8 into the external pinch gaps 106. The swivel functionality can also help retain the tube 8 within the external pinch gaps 106. For example, the swivelable (capable of being swiveled) external pinchers 104 can make it harder to pull the tube 8 out of the external pinch gaps 106 since the external pinchers 104 can move in response to post-pinch movement of the tube 8. In this way, a swivelable pinch system 101 can help retain tubes 8 in pinched configurations when subsequent forces arise that may have otherwise dislodged a tube 8 from an external pinch gap 106 in a non-swivel system 101. As another example, the swivelable external pinchers 104 can make it easier to pull a tube 8 out of the external pinch gaps 106 since the external pinchers 104 can move in response to post-pinch tube movement and rotate to "align" the tube 8 such that more of the post-pinch tube force is directed perpendicularly out of the external pinch gap 106. As yet another example, the swivelable external pinchers 104 may neither make it harder nor easier to retain a tube 8 in an external pinch gap 106.

A swivelable pinch system 101 may increase (e.g., relative to a fixed or non-swivel pinch system 101) the overall threshold force required to pinch the tube 8 in an external pinch gap 106 since the external pinchers 104 can move (e.g., rotate) in response to contact from the tube 8 and become "misaligned" with the tube force direction, thereby requiring more overall force to push the tube 8 into the gap 106 since the force applied is less concentrated in the direction of the gap 106. In some variations, the swivel arrangement can have stop points such that the tube 8 is configured to be compressed when the pincher system 101 is at the stop points. The stop points can correspond to the two swivel limits of the pincher system 101, for example, the clockwise and counterclockwise angular rotational limits about the device longitudinal axis (e.g., 15 degrees). As another example, a swivelable pinch system 101 may decrease (e.g., relative to a fixed or non-swivel pinch system 101) the overall threshold force required to pinch the tube 8 in an external pinch gap 106 since the external pinchers 104 can rotate to "align" the tube 8 such that more of the tube force is directed perpendicularly into the external pinch gap 106, thereby requiring less overall force to push the tube 8 into the gap 106 since the force applied is more concentrated in the direction of the gap 106. As yet another example, the swivelable external pinchers 104 may neither increase nor decrease the overall threshold force required to pinch the tube 8 into an external pinch gap 106.

The flexible neck and flexible external pincher base variations may also make it harder or easier to retain the tube 8 within the external pinch gaps 106 since the external pinchers 104 can move when the pincher system 101 has a flexible neck and/or flexible external pincher bases, thereby misaligning or aligning the component of the overall force directed toward or away from the external pinch gap 106. The flexible neck and flexible external pincher base variations may also increase or decrease the overall threshold force required to pinch the tube 8 in an external pinch gap 106 for the same reasons. As yet another example, the flexible neck and/or flexible external pincher base variations may neither increase nor decrease the overall threshold force required to pinch the tube 8 into an external pinch gap 106.

From proximal to distal, the external pinchers 104 can get wider and then narrower. The proximal tips of the external pinchers 104 can be narrower than the distal bases of the external pinchers 104. From proximal to distal, the tapered first portions 112a can get wider, for example, such that from the proximal tip of the external pinchers 104 to the inflection point 112c, the pincher 104 gets wider. From proximal to distal, the tapered second portions 112b can narrower, for example, such that from the inflection point 112c to the distal base of the external pinchers 104, the pincher 104 gets narrower. FIG. 7A illustrates that the external pinchers 104 can define external pinch gaps 106 that, from proximal to distal, become narrower until the inflection point 112c, after which the external pinch gaps 106 become wider. For example, the tapered pinch gaps 106 can have a cross-sectional shape of two opposing chemistry flasks (e.g., two opposing Erlenmeyer flasks), with the smaller of the two flask-shaped portions of the pinch gaps 106 being closer to the device distal end 10b than the other portion. The wider portion of the external gaps 106 near the base of the external pinchers 104 can help seat the tube 8 into a pinched configuration by enabling the inflection point 112c to function as the highest magnitude pinch point between two adjacent external pinchers 104. As another example, the tapered second portion 112b of the external pinchers can be non-tapered.

The external pinchers 104 can be varied in location, size, shape, and/or profile to enable optimized pinching performance for a range of tubing pull events. Lateral pulls or upward pulls, for example, can require different threshold pinching forces to restrict or stop flow through the tube 8. Variations of the physical features and relative positions of the external pinchers 104 can enable a device 10 with variable closing force features for variable pulls of the tubing 8. The threshold pinching forces can be controlled by the location, size, shape, and/or profile of the external pinchers 104, for example, the location of the inflection points 112c that exert maximum compression against the tube 8.

FIG. 7B illustrates that the external pinchers 104 can have multiple shapes and sizes. For example, the external first and second pinchers 104a, 104b can have the same size and shape. The external third pincher 104c can be larger and have a different shape than the external first and second pinchers 104a, 104b. The external third pincher 104c can be the largest of the pinchers 104, as shown in FIG. 7B, when the external third pincher 104 is configured to form part of the device first side 10c (e.g., the bottom of the device 10) and contact a patient's skin when the device 10 is in an attached configuration.

FIG. 7B further illustrates that taper of the tapered first and second portions 112a, 112b can taper at least partially in the radial direction (e.g., narrower and/or wider toward the device longitudinal axis A1), at least partially in a circumferential direction, at least partially in a longitudinal direction, or any combination thereof.

FIG. 7B further illustrates that the tube 8 can be connected to a movable shuttle 108. The movable shuttle 108 can be a slidable shuttle. The movable shuttle 108 can be configured to slide longitudinally (e.g., along the device longitudinal axis A1) relative to the external pinchers 104.

FIG. 7B further illustrates that the tube 8 can be forced into the external first pinch space 106ab when the tube 8 is non-axially pulled according to arrow 118a (e.g., in the plane defined by the device longitudinal and first transverse axes A1, A2). The tube 8 can be forced into the external second pinch space 106bc when the tube 8 is non-axially pulled according to arrow 118b (e.g., in the plane defined by the device longitudinal and second transverse axes A1, A3). The tube 8 can be forced into the external third pinch space 106ca when the tube 8 is non-axially pulled according to arrow 118*c* (e.g., in the plane defined by the device longitudinal and second transverse axes A1, A3).

FIG. 7B further illustrates that the tube 8 can have one or more internal pinchers 110, for example, 1 to 8 internal pinchers 104, including every 1 pincher increment within this range (e.g., 2 pinchers, 3 pinchers, 4 pinchers). The shuttle 108 can be configured to slide longitudinally (e.g., along the device longitudinal axis A1) relative to the internal pinchers 110.

Figure 7C:
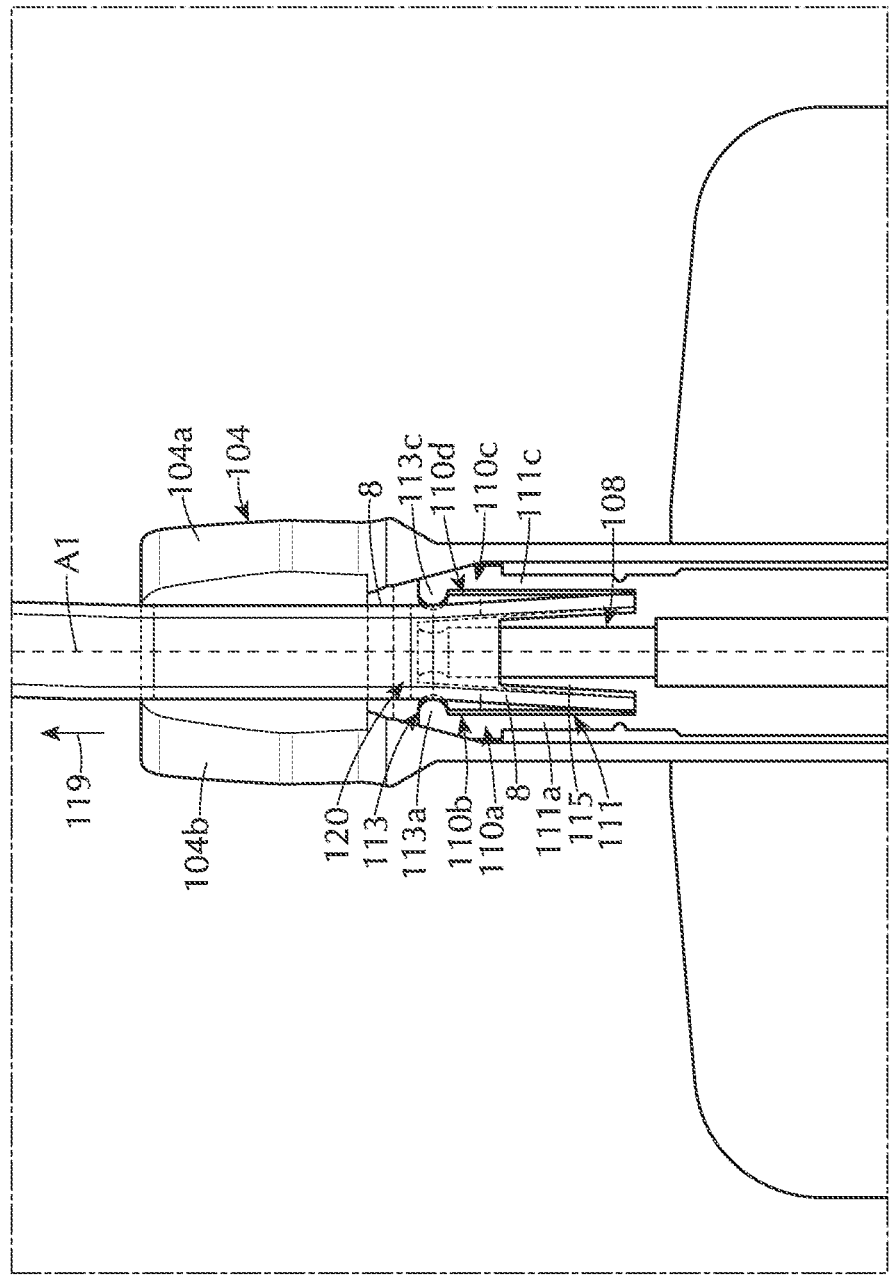
FIG. 7C illustrates a variation of a transverse cross-sectional view of the tissue access device of FIG. 7A taken along line 7C-7C.

FIG. 7C illustrates that the tube 8 can be connected to the shuttle 108.

FIG. 7C further illustrates that the pincher system 101 can have an internal first pincher 110*a*, an internal second pincher 110*b*, an internal third pincher 110*c*, an internal fourth pincher 110*d*, or any combination thereof. In FIG. 7C the internal second pincher 110*b* is shown almost entirely obstructed from view by the internal first pincher 110*a* and the internal fourth pincher 110*d* is shown almost entirely obstructed from view by the internal third pincher 110*c*.

Each internal pincher 110 can have a pincher arm 111. The pincher arm 111 can have a pincher protrusion 113. For example, FIG. 7C illustrates that the internal first pincher 110*a* can have an internal first pincher arm 111*a* and an internal first pincher protrusion 113*a*. The internal third pincher 110*c* can have an internal third pincher arm 111*c* and an internal third pincher protrusion 113*c*. The arms and protrusions of the second and fourth internal pinchers 110*b*, 110*d* are omitted for purposes of illustrative clarity. In other variations, the internal pinchers 110 can comprise arms 111 without protrusions 113.

FIG. 7C further illustrates that the shuttle 108 have a tapered surface 115. The tapered surface 115 can have, for example, the shape of a frusto-conical cone.

The internal pinchers 110 can be configured to restrict or stop fluid flow through the tube 8 in the event of needle dislodgement after insertion. Dislodgement can occur before or after the device 10 has been taped to a patient's skin (e.g., skin 100).

For example, the internal pinchers 110 (e.g., via the arms 111 and/or protrusions 113) can be configured to restrict or stop fluid flow through the device 10 when the tube 8 is pulled in an axial direction, for example, along the device longitudinal axis A1. When the tube 8 is moved in an axial direction away from the device distal end 10*b*, the shuttle 108 can move axially away from the device distal end 10*b* along the device longitudinal axis A1. When the shuttle 108 is moved, the tube 8 can be forced between the internal pinchers 110 and the shuttle surface 115. For example, the tube 8 can be forced into the internal pinchers 110 such that the tube 8 is pinched partially or fully closed by internal pinchers 110 compressing (e.g., progressively compressing) the tube 8 against the tapered shuttle surface 115. In other variations, the shuttle surface 115 can be straight without a taper. The tube 8 can be pinched by compression pinch points optimized to pinch the tube 8 in the event the tubing 8 is pulled in an axial direction. The compression pinch points can be defined by the internal pinchers 110.

FIG. 7C further illustrates that the tube 8 can be forced against the shuttle surface 115 when the tube 8 is axially pulled according to arrow 119 (e.g., along the device longitudinal axis A1). For example, FIG. 7C illustrates that the tube 8, the shuttle 108, and the shuttle surface 115 can have a non-pinched configuration as illustrated by the solid lines in FIG. 7C and a pinched configuration as shown by the dashed lines 120 in FIG. 7C. The dashed lines 120 show the pinched configuration of the tube 8 against the shuttle surface 115 when the shuttle 108 is axially pulled according to arrow 119 via the tube 8.

FIG. 7C further illustrates that axial forces on the needle 12 and/or the housing 14 away from the needle insertion site due to external forces on the tube 8 can be translated into shuttle motion in the axial direction away from the needle insertion site. Such motion can lead to the internal pinchers 110 (e.g., via the arms 111 and/or protrusions 113) being forced into a pinched position against the tube 8 via an incline within the needle body (e.g., the inclined shuttle surface 115). This incline and surrounding features can be modified to result in any specific threshold closing force required. Together, the internal mechanism for axial pinching (e.g., pinchers 110 and shuttle 108) coupled with the external pinch points (e.g., via external pinchers 104) allows the system 101 to effectively pinch off and stop or limit fluid flows as a result of tubing axial and non-axial pull forces of any set threshold in any position on the device 10.

FIG. 7D illustrates a variation of a general classification scheme 130 for possible forces that may be experienced on an inserted fluid delivery needle 12 in a patient (e.g., in a forearm) via movement of the tube 8. The tube 8 can be purposely or inadvertently tugged in any number of directions away from the insertion site. For example, FIG. 7D illustrates first, second, third, and fourth force classifications 130*a*, 130*b*, 130*c*, and 130*d* for the tube 8. The first force classification 130*a* can be axial movement of the tube 8 away from the needle insertion point. The second, third, and fourth force classifications 130*b*, 130*c*, 130*d* can correspond to the classifications shown. The combination of external pinch points (e.g., between pairs of external pinchers 104) and the internal shuttle mechanism 108 can be used to protect patients from tube pulls in any one of these classification areas. For example, the first force classification 130*a* can correspond to force 119 in FIG. 7C, the second force classification 130*b* can correspond to force 118*a* in FIG. 7B, the third force classification 130*c* can correspond to force 118*b* in FIG. 7B, and the fourth force classification 130*d* can correspond to force 118*c* in FIG. 7B.

Figure 8A:
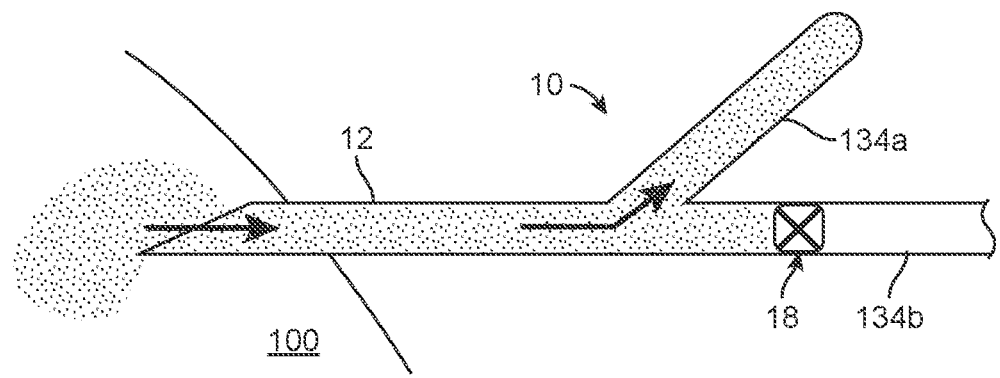
FIGS. 8A and 8B illustrate a variation of a schematic of a tissue access device having multiple flow paths.
Figure 8B:
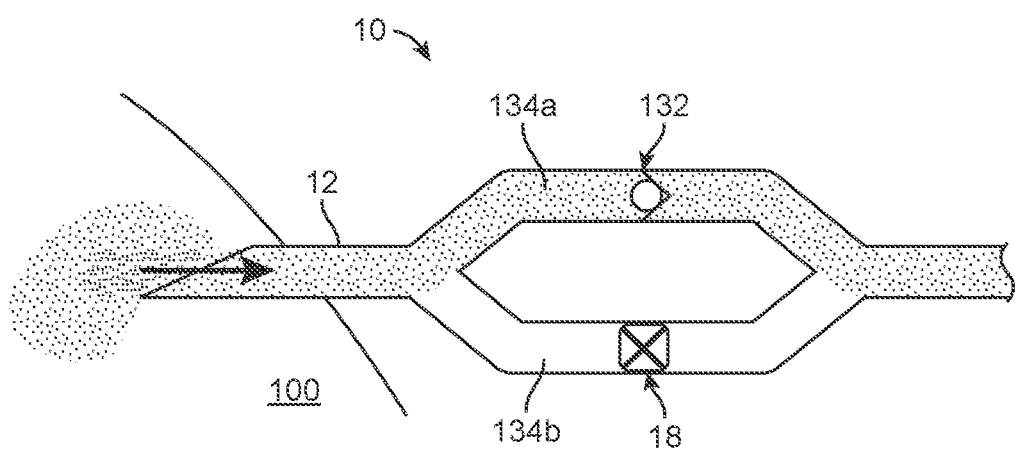

FIGS. 8A and 8B illustrate a variation of a method for allowing visual observation of blood flashback during cannulation, for example, with devices 10 having sensors 18. FIGS. 8A and 8B illustrate a variation of a valve 132 (e.g., a one-way check valve) for cannulation lock. FIGS. 8A and 8B illustrate that two fluid paths (e.g., a first flow path 134*a* and a second flow path 134*b*) can be within the needle body (e.g., within the housing 14). FIGS. 8A and 8B further illustrate that the first flow path 134*a* can be used to visualize flashback and that the second flow path 134*b* can be used for therapy (e.g., hemodialysis therapy). The traditional fluid path for pumping blood into or out of the body to the hemodialysis machine can be the second flow path 134*b*.

FIG. 8A illustrates that the second flow path 134*b* can have a sensor 18. The sensor 18 can be configured to allow blood flow through the second flow path 134 after cannulation. For example, the second flow path 134*b* can include the pinch valve 18 to control flow stoppage during inadvertent needle dislodgement.

FIG. 8B illustrates that the first flow path 134*a* can include the one-way check valve 132. The one-way check valve 132 can be configured to allow blood to flow from the patient through the needle body (e.g., through the housing 14) under the natural pumping pressure of the patient during cannulation. For example, the one-way check valve 132 can be configured to allow blood to flow from the patient through the needle body (e.g., through the housing 14) only under the natural pumping pressure of the patient during cannulation. The first flow path 134a can allow blood to appear in the flow tube behind the needle body (e.g., toward the device proximal end 10a) during cannulation.

During cannulation, fluid can flow through the first flow path 134a but not through the second flow path 134b. The sensor 18 can occlude the second flow path 134b during cannulation. During therapy (e.g., after cannulation), fluid can flow through the second flow path 134b but not through the first flow path 134a. The one-way check valve 132 can occlude the first flow path 134a after cannulation.

FIGS. 8A and 8B illustrate blood flowing through the first flow path 134a during cannulation and being blocked by the sensor 18 in the second flow path 134b. After cannulation (e.g., when the device 10 is taped against a patient's skin and the sensor changes from the closed configuration to the open configuration), blood being pumped into the body would not be able to move through the one way valve 132 of the first flow path 134a and would instead flow through the second flow path 134b past the sensor 18. For example, the one-way check valve 132 can allow fluid to flow through the first flow path 134a in a first direction but not in a second direction opposite the first direction. The first direction can be away from the tissue 100 and the second direction can be toward the tissue 100. During cannulation, the sensor 18 can block the second flow path 134b. After cannulation, the sensor 18 can move from a closed position to an open position to allow blood to flow through the second flow path 134b.

Figure 9A:
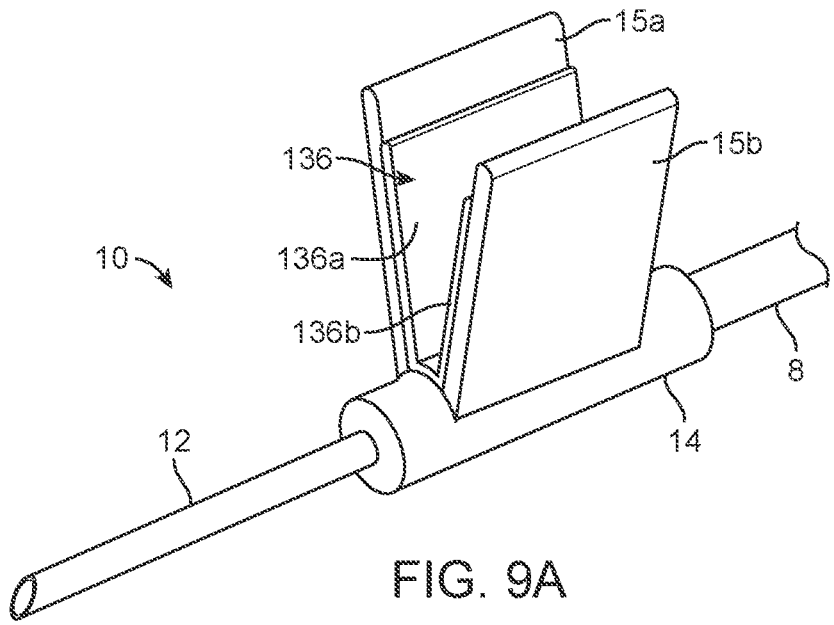
FIG. 9A illustrates a perspective view of a variation of a tissue access device having a variation of a flow control system.

FIG. 9A illustrates a variation of a device 10 having a flow control system 136. The flow control system 136 can be a cannulation control system that can open the flow path through the device 10 during the cannulation process. The flow control system 136 can be a cannulation lock system (also referred to as a cannulation configuration system). For example, the flow control system 136 can include spring-loaded wings 136a and 136b that work to provide a cannulation lock suitable for allowing blood to flow through the housing 14 during insertion of the needle into the patient while the needle 12 is not yet fully secured to the body. A cannulation lock can be the configuration of the device 10 during cannulation. The device 10 may or may not be "locked" into this position, and may be biased to return to a non-cannulation configuration when user input that places the device 10 into the cannulation configuration ends. The flow control system 136 can be positioned in a cannulation configuration by pinching the needle wings 15a and 15b into an upright position (e.g., by pinching the needle wings 15a and 15b toward the device first transverse axis A2). The wings 15a and 15b can be pinched, for example, by bending, and/or rotating the wings. The wings can rotate about their base. Such pinching is standard for needle manipulation during insertion into the body. Pinching the wings 15a and 15b into an upright position can correspondingly move the spring-loaded 136a and 136b close together as shown in FIG. 9A. This movement of the spring-loaded wings 136a and 136b toward the device first transverse axis A2 can trigger the flow path through the device 10 to open which can allow for blood to flashback into the proximal portion of the needle tubing. When the wings 15a and 15b are taped down after cannulation, the flow path can also be open. The flow path can stay open, for example, until such time as the needle 12 is either accidentally or purposely removed from the patient and the flow path is automatically blocked by the sensor 18.

FIG. 9A illustrates that the cannulation lock system 136 can be a wing insert. The wing insert 136 can have a first wing extension 136a and a second wing extension 136b attached to or integrated with the first and second wings 15a, 15b, respectively.

FIG. 9A further illustrates the wings 136a and 136b held partially open by a spring (e.g., an internal spring). This can be the default position of the device 10 having the cannulation lock 136. Flow through the device 10 can be blocked when the cannulation lock system 136 is in the default position.

Figure 9B:
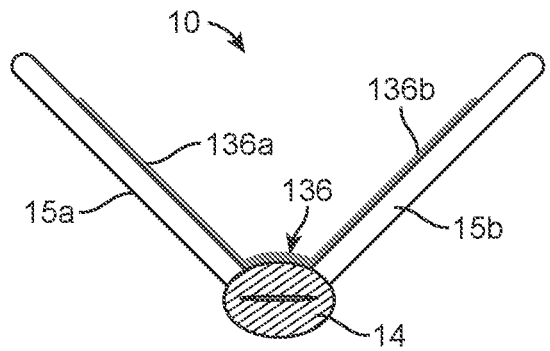
FIG. 9B illustrates a front view of the tissue access device of FIG. 9A.

FIG. 9B further illustrates that the wings can be about 65 degrees to about 90 degrees apart when the cannulation lock system 136 in the default position. FIG. 9B further illustrates that the spring connected to the spring-loaded wings 136a and 136b can be configured to bias the spring-loaded wings 136a and 136b in the configuration shown in FIG. 9B such that the flow path through the device is closed.

Figure 9C:
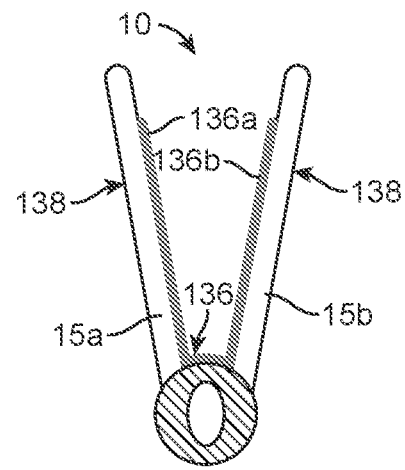
FIG. 9C illustrates a front view of the tissue access device of FIG. 9A in an open configuration.

FIG. 9C illustrates that the wings 15a and 15b (and the spring-loaded wings 136a and 136b) can be pinched during cannulation to open the flow path through the device 10 as indicated by arrows 138. The wings 15a and 15b (and the spring-loaded wings 136a and 136b) can rotate when pinched (e.g., arrows 138).

Figure 9D:
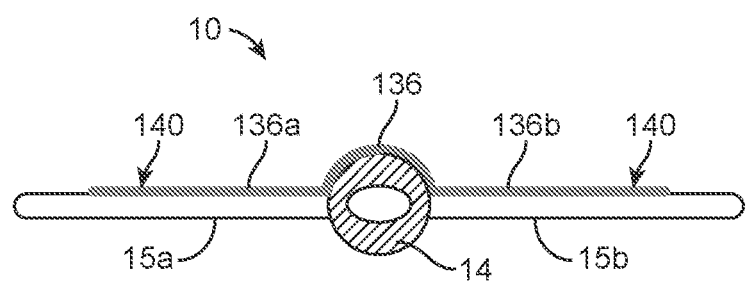
FIG. 9D illustrates a front view of the tissue access device of FIG. 9A in a closed configuration.

FIG. 9D illustrates that the wings 15a and 15b can be pressed against skin after cannulation as indicated by arrows 140. The flow path through the device 10 can be open when the wings 15a and 15b are in the configuration shown in FIG. 9D, which can be the configuration of the device 10 when taped against tissue.

Figure 10A:
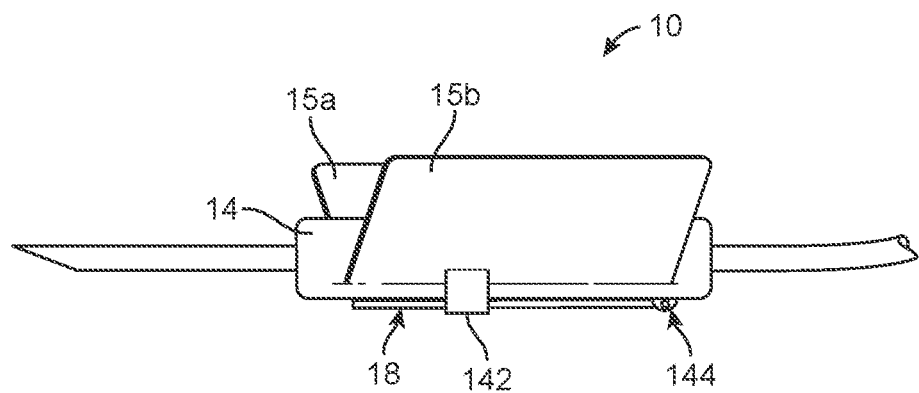
FIG. 10A illustrates a variation of a tissue access device in an open configuration having a variation of a flow control system.
Figure 10B:
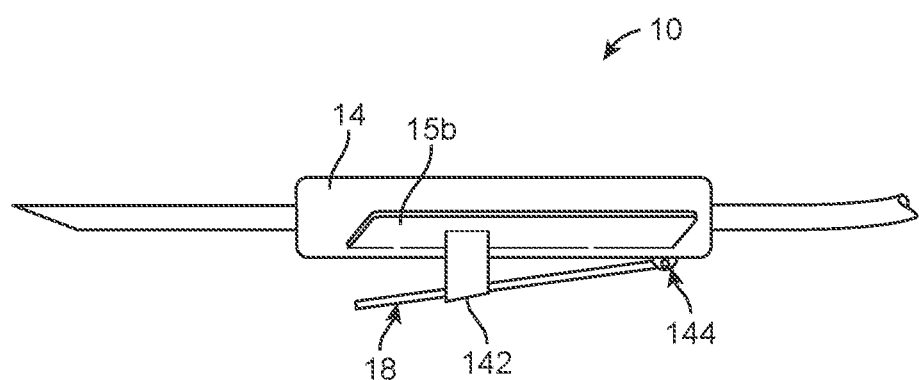
FIG. 10B illustrates the tissue access device of FIG. 10A in a closed configuration.

FIGS. 10A and 10B illustrate a variation of a device having a flow control system comprising a latch 142. The latch 142 can open the flow path of the device 10 during cannulation, for example, by moving the device 10 into a cannulation lock position. The latch can be directly or indirectly connected to the first wing 15a and/or the second wing 15b. The latch 142 can be configured to pull upward (e.g., along the device first transverse axis A2) on the skin-sensing mechanism 18 (e.g., shown as a blade in this variation of the device 10) when the wings 15a and 15b are bent, rotated, and/or flexed together, for example, in the traditional way used to hold the needle 12 for insertion. This bending/rotating/flexing can activate the latch 142 to pull the skin-sensing element 18 closer to the housing 14 to insure an open blood flow path through the device 10, for example, during cannulation. This flow path allows for blood flashback during cannulation. For example, FIG. 10B illustrates the wings 15a and 15b in a non-pinched configuration and FIG. 10A illustrates the wings 15a and 15b in a pinched configuration with the latch 142 having pulled the sensor 18 closer to the housing 14 in FIG. 10A relative to the latch position in FIG. 10B. FIG. 10A illustrates that the latch 142 can pull the sensor 18 into an open position. When the device 10 is taped down on the patient, the latch 142 can have a mechanical release that can move it away from or detach from the sensor 18. FIGS. 10A and 10B further illustrate that the sensor 18 can be attached to the housing 14 via a hinge (also referred to as a hinge connection).

Figure 11A:
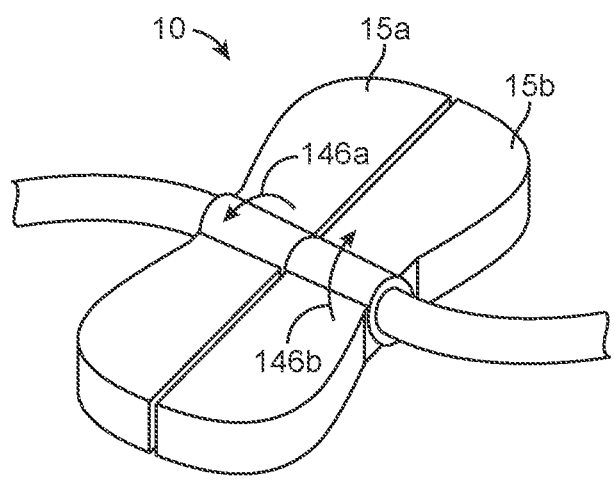
FIG. 11A illustrates a perspective view of a variation of a flow control system.
Figure 11B:
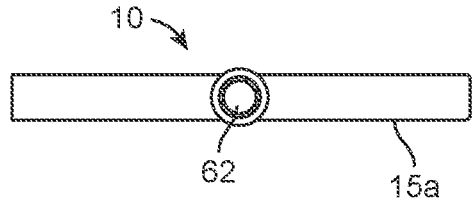
FIG. 11B illustrates a front view of the flow control system of FIG. 11A in an open configuration.
Figure 11C:
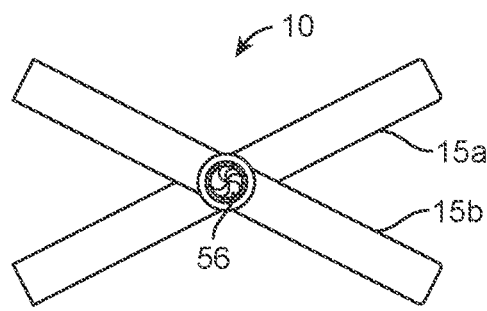
FIG. 11C illustrates a front view of the flow control system of FIG. 11A in a closed configuration.
Figure 11D:
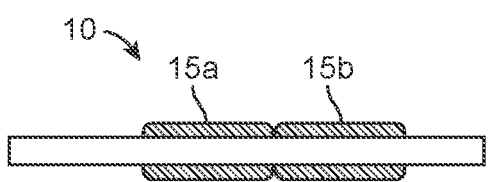
FIG. 11D illustrates a side cross-sectional view of the flow control system of FIG. 11B.
Figure 11E:
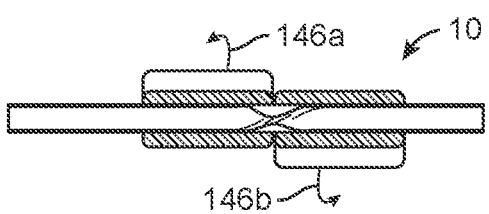
FIG. 11E illustrates a side cross-sectional view of the flow control system of FIG. 11C.

FIGS. 11A-11E illustrate a variation of a flow control system having rotatable wings 15a and 15b. The flow control system can be a cannulation control system that can be configured to open the flow path through the device 10 during cannulation. The wings 15a and 15b can rotate about their respective bases, for example, where they each connect to the housing 14. For example, FIGS. 11A-11E illustrate that the wings 15a and 15b can be rotated rotate into an X-shape during cannulation. The wings 15a and 15b can allow for and/or can impart torsional action on an internal flow path (e.g., on device flow channel 62) when rotated, for example, relative to the device longitudinal axis A1. The wings 15a and 15b can function as a cannulation lock to block flow through the needle 12 when the butterfly wings (e.g., wings 15a and 15b) are bent, rotated, and/or flexed into an upright position (e.g., toward the device first transverse axis A2) as is traditionally done for needle manipulation during cannulation. The wings 15a and 15b can create opposing forces that can act on the flow path when rotated in opposite directions. The opposing forces can twist the flow path shut. For example, FIG. 11A illustrates that the device 10 can have rotatable wings 15a and 15b that can rotate in directions 146a and 146b, respectively, or vice versa. As another example, one or both of the wings 15a and 15b can rotate in direction 146a and/or in direction 146b. When both wings 15a and 15b can rotate in both directions, the device 10 can form two different "X's." FIG. 11B illustrates that the flow path 62 can be open when the wings 15a and 15b are flat (e.g., against the skin). FIG. 11C illustrates that the flow path 62 can be closed when the wings 15a and 15b are rotated to form an X-shape. A torsional force can twist the flow path shut when the wings are rotated in opposite directions. For example, FIG. 11C further illustrates that the flow path 62 can close by twisting a tube defining the housing conduit 56 by applying torsion to the tube when the wings 15a and 15b are rotated in opposite directions. FIG. 11D illustrates that the flow path 62 can be open when the wings 15a and 15b are parallel to each other, or otherwise not in an X configuration. FIG. 11E illustrates that the flow path 62 can be closed by twisting the tube defining the housing conduit 56 with the wings 15a and 15b.

Figure 12A:
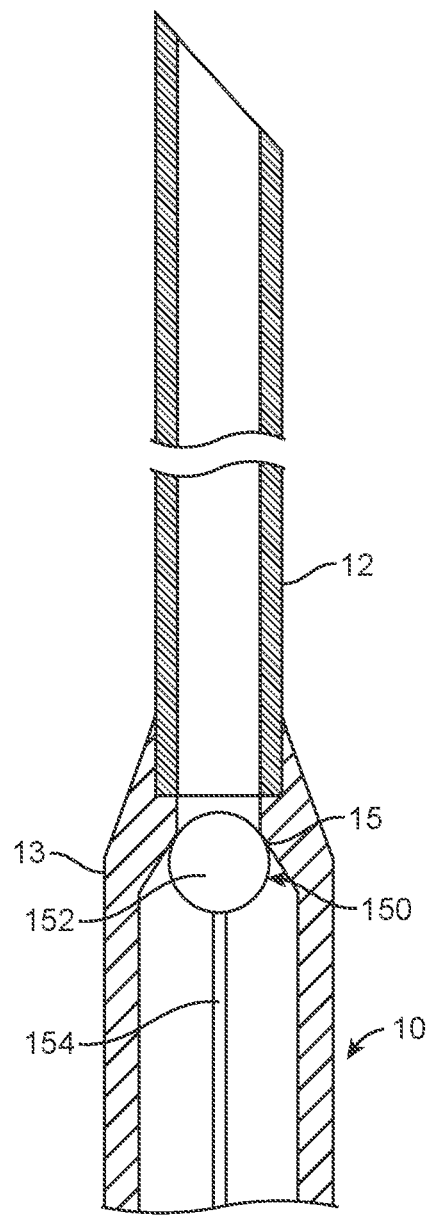
FIG. 12A illustrates a cross-sectional view of a flow control system in a closed configuration.
Figure 12B:
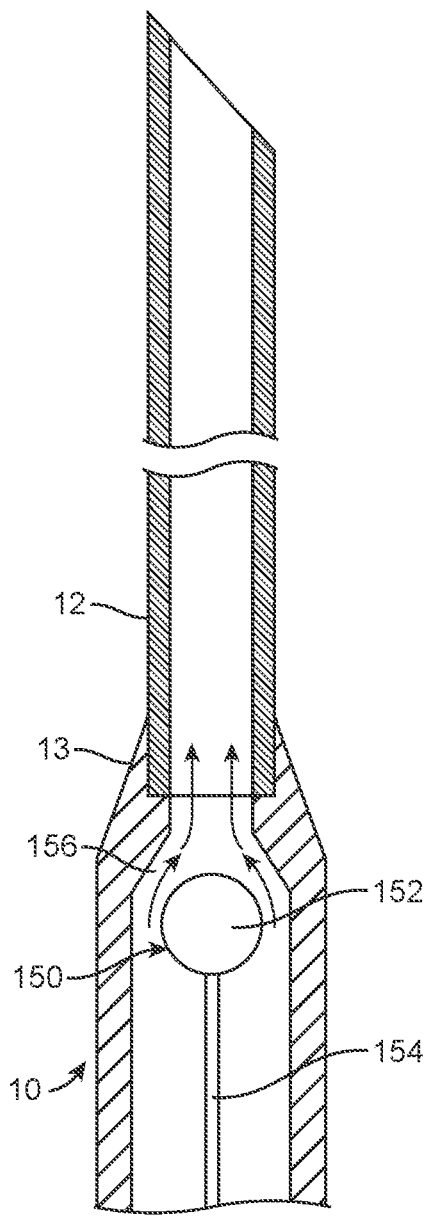
FIG. 12B illustrates the flow control system of FIG. 12A in an open configuration.

FIGS. 12A and 12B illustrate a variation of a flow control system 150. The flow control system 150 can be a cannulation control system. For example, the flow control system 150 can be a ball valve system that can be integrated into the devices 10 as a method to control flow through the needle 12 during cannulation. The ball valve system 150 can be inside the device 10. The ball valve 150 can be actuated via needle wing bending, rotating and/or flexing the wings 15a and 15b toward the device first transverse axis A2 as is typically performed when inserting the needle 12 into the patient so as to insure the flow is open during cannulation. The ball valve 150 can also be controlled to block flow during needle dislodgement. FIGS. 12A and 12B illustrate that the ball valve 150 can include a ball 152 and a mechanical link 154 attached to the ball 152. The mechanical link 154 can be directly or indirectly attached to the device wings and/or to the sensor 18. The flow path (e.g., in the needle hub 13) can have a taper 156 that can guide the ball 152 into the needle port to block the flow path through the device 10. FIG. 12A illustrates the ball valve system 150 in a closed configuration (blocking flow through the needle 12) and FIG. 12B illustrates the ball valve system 150 in an open configuration (allowing flow through the needle 12).

FIGS. 13A-13E illustrate a variation of a flow controller 158. The flow controller 158 can be a cannulation flow controller. The flow control system 158 can be a cannulation controller that can be configured to open the flow path through the device 10 during cannulation. For example, the flow controller 158 can be a cocked blade mechanism that can enable cannulation lock during cannulation. In this variation, the device 10 is not activated for skin sensing detection until the needle 12 has been inserted into the patient and the needle inserter (e.g., the person inserting the needle) activates the skin sensing mechanism 18 via a physical action to unlock the skin-sensing ability of the device 10, for example, using the cocked blade mechanism 158. FIG. 13A illustrates that the cocked blade mechanism 158 can be attached to the sensor 18. FIG. 13A further illustrates the device 10 in an open configuration during cannulation. FIG. 13B illustrates the device 10 in an open configuration with the cocked blade mechanism 158 in a cocked position when the needle 12 is inserted into tissue. FIG. 13C illustrates the device 10 in a closed configuration with the cocked blade mechanism 158 in an un-cocked activated position. FIG. 13C further illustrates that the cocked blade mechanism and deform the flow path by pushing against the housing 14. FIGS. 13D and 13E illustrate the cocked blade mechanism in two configurations relative to the housing 14 and housing conduit 56.

Figure 14A:
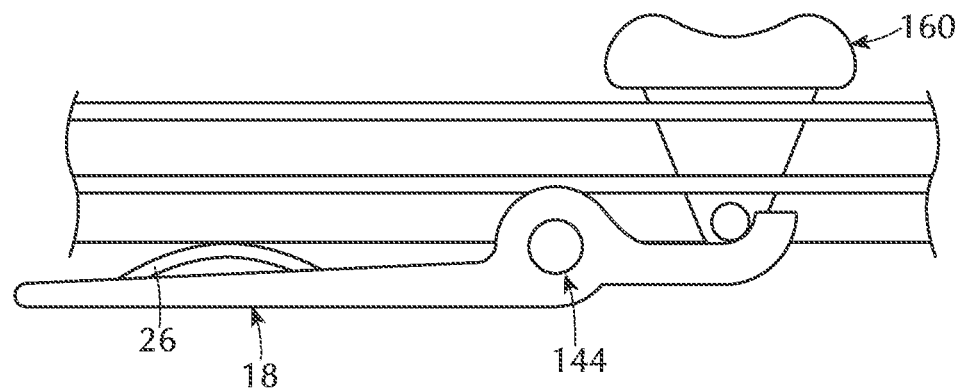
FIGS. 14A and 14B illustrate a variation of a flow control mechanism.
Figure 14B:
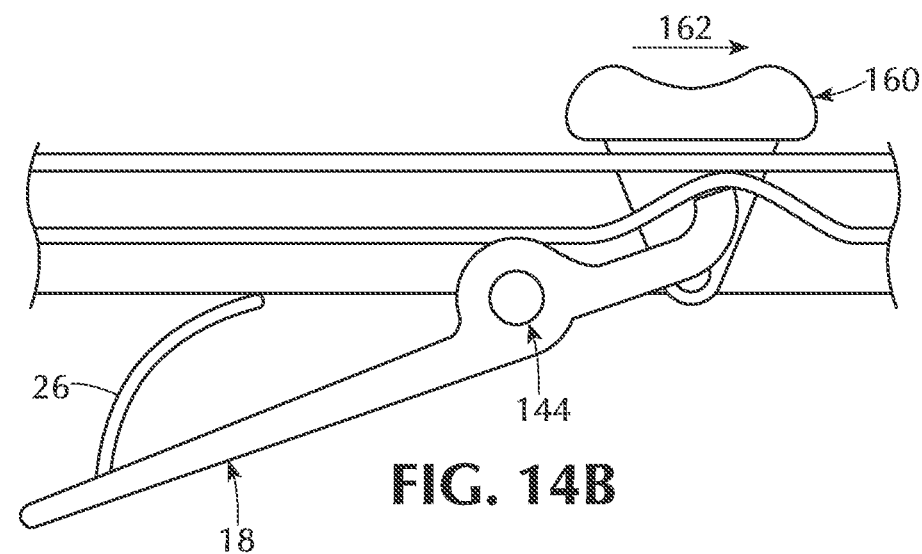

FIGS. 14A and 14B illustrate a variation of a flow control mechanism that can allow a user to control, via a digitally operated slider 160, the ability of the device 10 to be put into an actuated state. During cannulation, the flow control mechanism can be deactivated via the slider 160 and allow flow. The flow control mechanism can be the sensor 18. For example, FIG. 14A illustrates the system in an open, cannulated position. After physically activating the flow control mechanism via the slider 160, the device 10 can assume its ability to use the skin-sensing member 18 to determine the status of fluid flow control through the needle 12. For example, FIG. 14B illustrates that the slider 160 can be slid back (e.g., arrow 162), allowing the sensor 18 to be cocked.

Figure 15A:
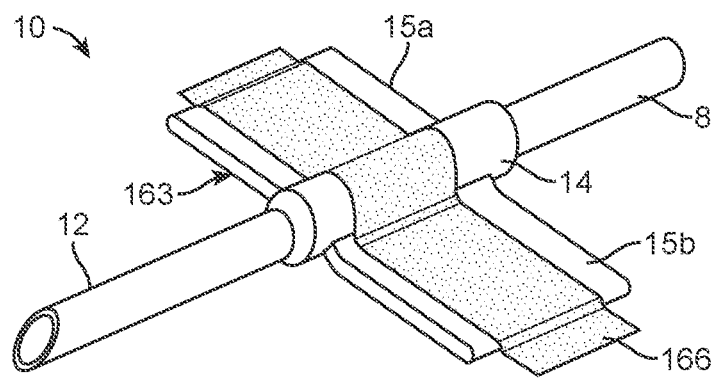
FIGS. 15A-15D illustrate a variation of a flow control mechanism.
Figure 15B:
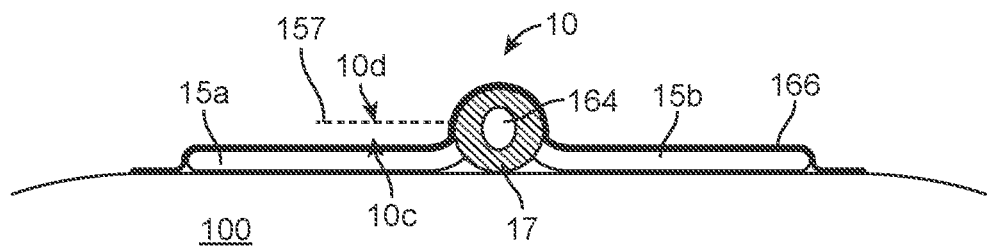
Figure 15C:
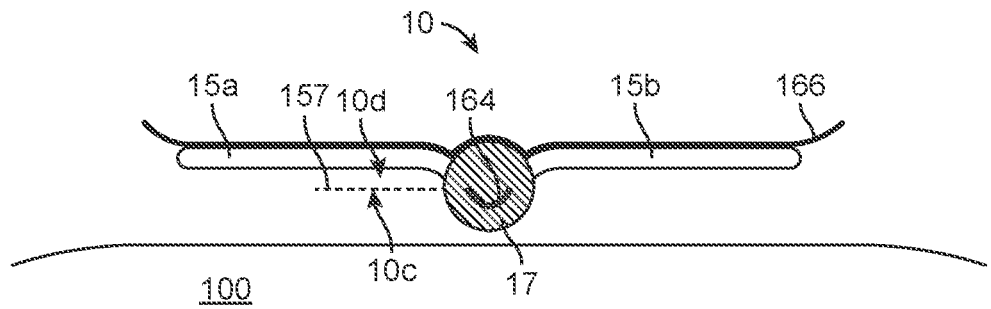
Figure 15D:
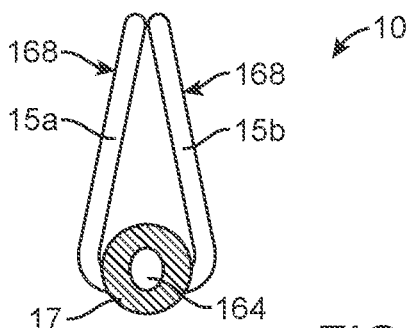

FIGS. 15A-15D illustrate a variation of a flow control mechanism 163. The flow control mechanism can be a flow orifice shaper 163. The flow control mechanism 163 can include device wings 15a and 15b and an internal orifice 164 (e.g., a flow path orifice of device channel 62). The shape of the internal orifice 164 can be mechanically controllable (e.g., opened and closed) via the wings 15a and 15b. The flow path shape control system 163 can be used during insertion of the needle 12 into the patient. The mechanically controllable orifice 164 can be configured to allow blood flow through the device 10 when the needle wings 15a and 15b are bent, rotated, and/or flexed into an upright position toward the device first transverse axis A2 as is typical during needle insertion and when the needle wings 15a and 15b are taped securely in place flat onto the patient's skin. As another example, the mechanically controllable orifice 164 can be configured to allow blood flow through the device 10 only when the needle wings 15a and 15b are bent, rotated, and/or flexed into an upright position as it typical during needle insertion and only when the needle wings 15a and 15b are taped securely in place flat onto the patient's skin. Other conditions (e.g., inadvertent removal of the needle during therapy for example) can cause the skin-sensing mechanism 18 to act on the orifice 164, insuring the orifice is put into a closed flow state. FIG. 15A illustrates that the device 10 can be secured to tissue with tape 166. FIG. 15B illustrates that the orifice 164 can have an open shape when the wings 15a and 15b are substantially parallel to each other and are above the plane 157 defined by the device longitudinal and second transverse axes A1, A3 (e.g., see FIG. 1 for axes) such that the wings 15a and 15b are on the device first side 10c. FIG. 15B further illustrates that the device 10 can be taped to tissue 100 to maintain the open shape of the orifice 164 after cannulation. FIG. 15C illustrates that the orifice 164 can have a closed shape when the wings 15a and 15b are substantially parallel to each other and are above the plane 157 defined by the device longitudinal and second transverse axes A1, A3 (e.g., see FIG. 1 for axes) such that the wings 15a and 15b are on the device second side 10d. FIG. 15D illustrates that the orifice 164 can have an open shape when the wings 15a and 15b are bent, rotated, and/or flexed toward each other as indicated by arrows 168. FIGS.

15B and 15D illustrate that the orifice can have an open shape when the wings 15a and 15b are taped to skin 100 and when they are pinched toward each other.

Figure 16A:
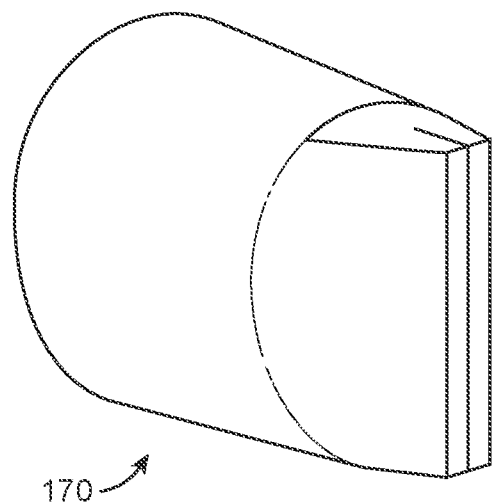
FIGS. 16A and 16B illustrate a variation of a flow control mechanism.
Figure 16B:
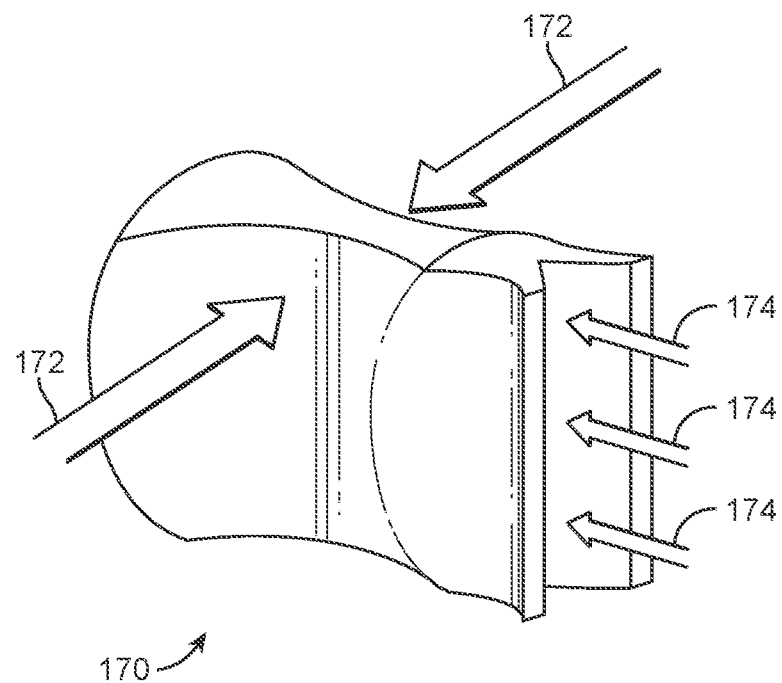

FIGS. 16A and 16B illustrate a variation of a flow control mechanism 170. The flow control mechanism 170 can be a one-way valve mechanism that can be integrated into the device 10 to provide an efficient mechanism for enabling one-way fluid flow as part of a technique to insure effective cannulation lock of the safety mechanism during needle insertion. For example, the one-way valve mechanism 170 can open the flow path of the device 10 during cannulation. The one-way valve 170 can be directly or indirectly connected to the first wing 15a and/or the second wing 15b such that articulation of the wings 15a and 15b (e.g., toward the device first transverse axis A2) can compress a first portion the one-way valve 170. The compression of the first portion of the one-way valve 170 can cause a second portion of the one-way valve 170 to expand, open, or define a flow channel. For example, FIG. 16B illustrates that when the component 170 is compressed (e.g., arrows 172) during cannulation, the front of the component 170 can open to allow fluid to flow (e.g., arrows 174) though the device 10. For example, the component 170 can be compressed when the wings 15a and 15b of the device 10 are rotated to insure open flow path during needle insertion.

Figure 17A:
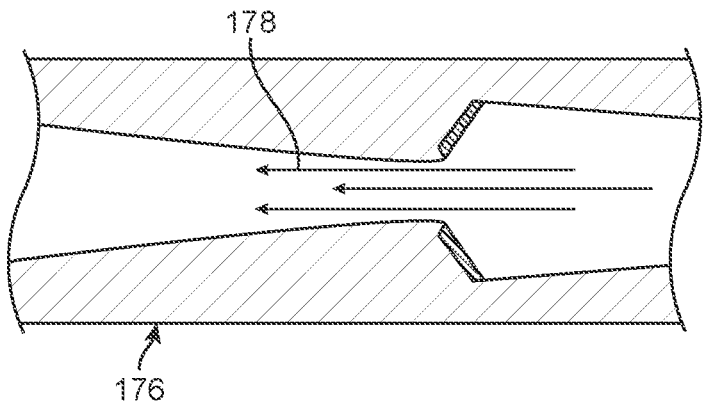
FIGS. 17A and 17B illustrate a variation of a flow control mechanism.
Figure 17B:
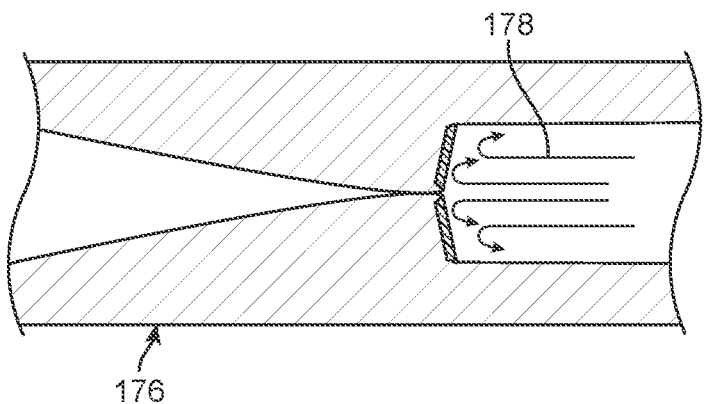

FIGS. 17A and 17B illustrate a variation of a flow control mechanism 176. The flow control mechanism 176 can be a pressure valve mechanism that can be integrated with the device 10 to provide an efficient mechanism for enabling one-way fluid flow as part of a technique to insure effective cannulation lock during needle insertion. For example, the pressure valve 176 can open the flow path of the device 10 during cannulation. FIG. 17A illustrates that blood can flow (e.g., arrows 178) through the pressure valve 176 when the blood velocity is low, for example, when there is back pressure. Back pressure can be in the line during cannulation. The back pressure can be on the side of the arrows 178 having the arrow heads. FIG. 17B illustrates that the component 176 can have a closed configuration when the blood velocity is high, for example, when there is no back pressure. FIG. 17B illustrates the flow 178 being blocked.

Figure 18A:
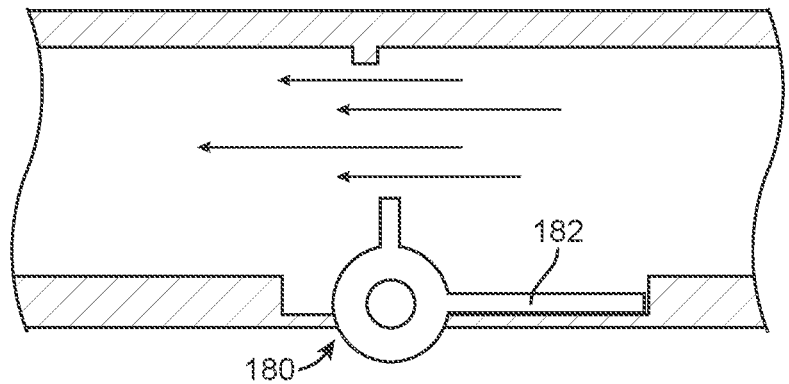
FIGS. 18A and 18B illustrate a variation of flow control mechanism.
Figure 18B:
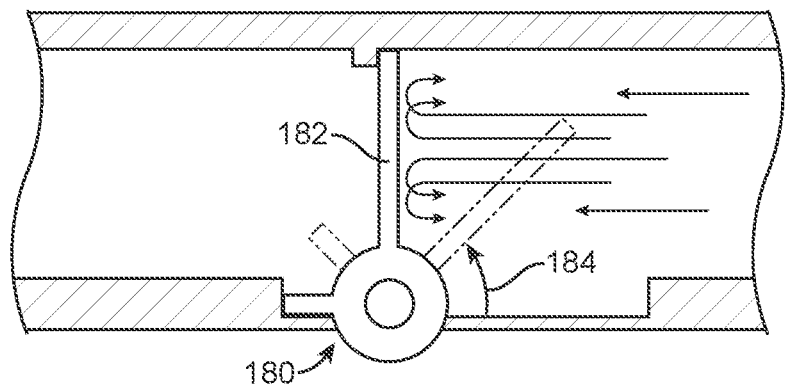

FIGS. 18A and 18B illustrate a variation of a flow control mechanism 180. The flow control mechanism 180 can be a turnstile valve 180 that can be integrated with the device 10 to provide an efficient mechanism for enabling one-way fluid flow as part of a technique to insure effective cannulation lock during needle insertion. For example, the turnstile valve 180 can open the flow path of the device 10 during cannulation. The turnstile valve 180 can be activated via bending, rotating, and/or flexing the wings 15a and 15b (e.g., toward the device transverse first axis A2) to insure open flow path during needle insertion. FIG. 18A illustrates that the turnstile valve 180 can have an open configuration when the wings 15a and 15b are pinched together and/or when the wings 15a and 15b are substantially parallel to each other. FIG. 18B illustrates that the turnstile occluder arm 182 can rotate (e.g., arrow 184) into the flow path 62 to block flow when the wings 15a and 15b are in their default position.

Figures 19A, 19B:
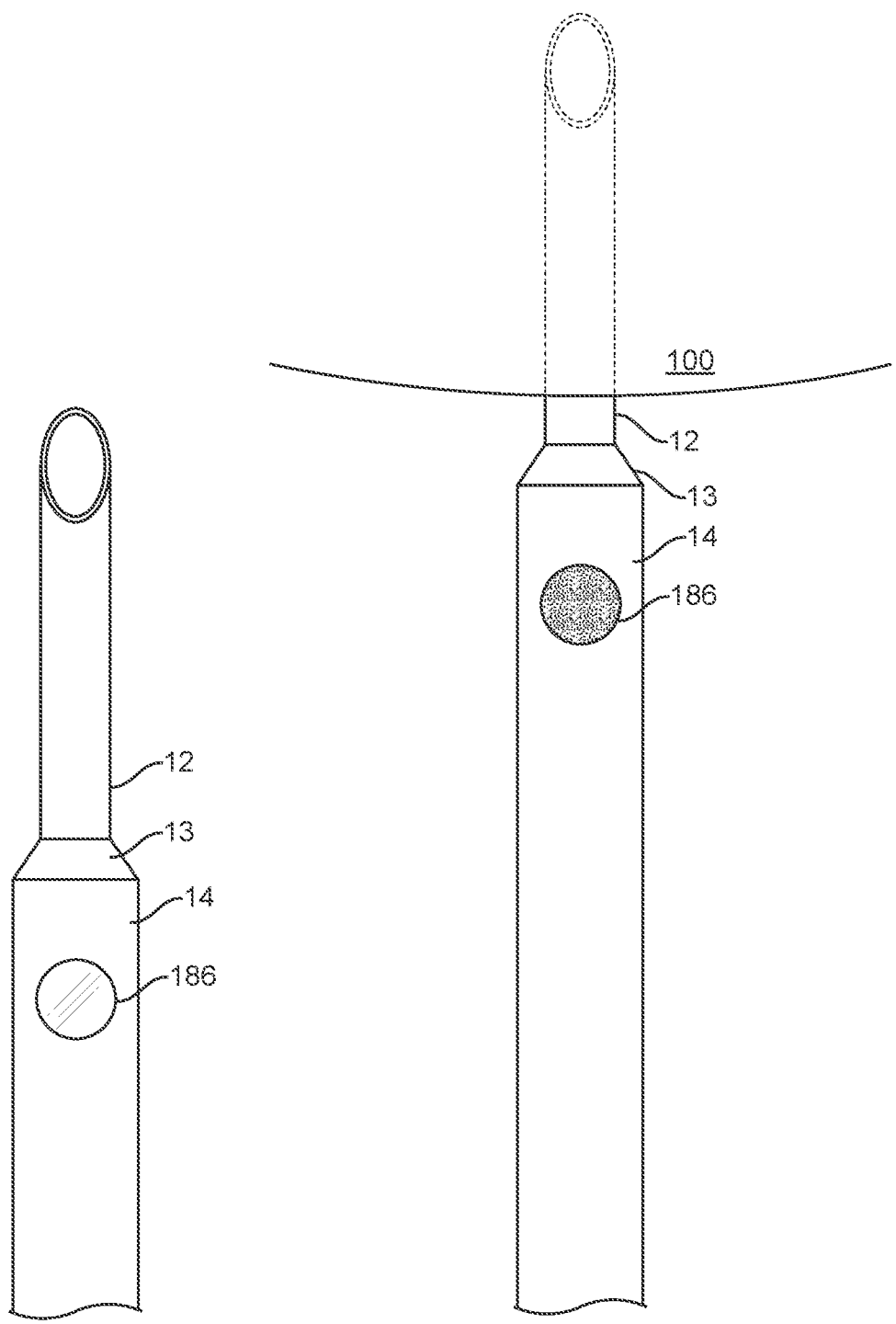
FIGS. 19A and 19B illustrate a variation of a visual indicator.

FIGS. 19A and 19B illustrate a variation of a visual indicator 186 that can be integrated into the device 10. The indicator 186 can be used to indicate blood flashback within the needle body itself and not require a flow path that delivers blood back into the distal tubing during insertion as is traditionally done. The indicator 186 in FIG. 19A indicates no blood or no flash back and the darker indicator 186 in FIG. 19B indicates blood or the presence of flashback. FIG. 19A illustrates the indicator 186 before cannulation and FIG. 19B illustrates the indicator 186 after cannulation with flashback visible in the indicator 186. The indicator 186 can be a transparent window in the housing 14 that visually exposes the device flow path 62, for example, near the needle hub 13.

FIGS. 20A-20G illustrate a variation of a strap 188 that can be integrated with the device 10. The strap 188 can provide a cannulation lock. For example, the strap 188 can be configured to force the sensor 18 into an open configuration during cannulation. FIGS. 20A-20G illustrate that when the needle wings 15a and 15b are bent, rotated, and/or flexed toward each other during cannulation (e.g., toward the device first transverse axis A2), the strap 188 can pull the sensor 18 into a position that enables fluid flow through the needle body. For example, the strap 188 can pull the sensor 18 into an open position. In this open position, blood flashback during insertion can be seen and naturally viewed by the person inserting the needle, for example, where the device 10 has a visual indicator 186. When this needle is taped into position, fluid can flow (e.g., freely flow) through the device 10 until the needle 12 is purposely or inadvertently removed from the body and the flow stop mechanism (e.g., sensor 18) is activated. The strap 188 can be integrated with or attached to the housing 14 and/or to the wings 15a and 15b. The strap 188 can be an elastic material. The strap 188 can be an in-elastic material. The strap 188 can be a strip of material having a flexible shape. The strap can bend with the wings 15a and 15b are rotated and de-rotated.

Figure 20A:
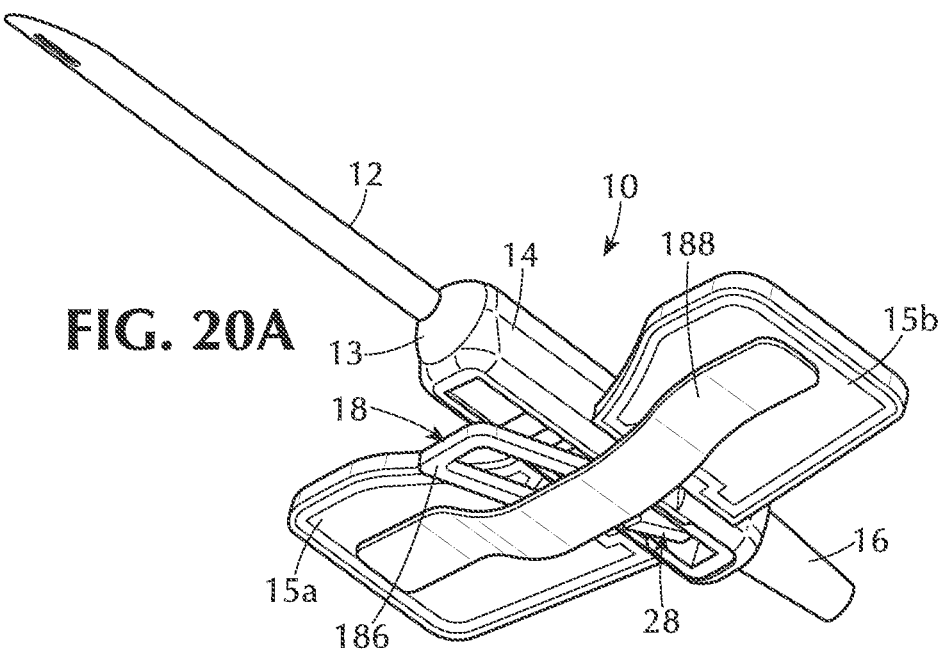
Figure 20B:
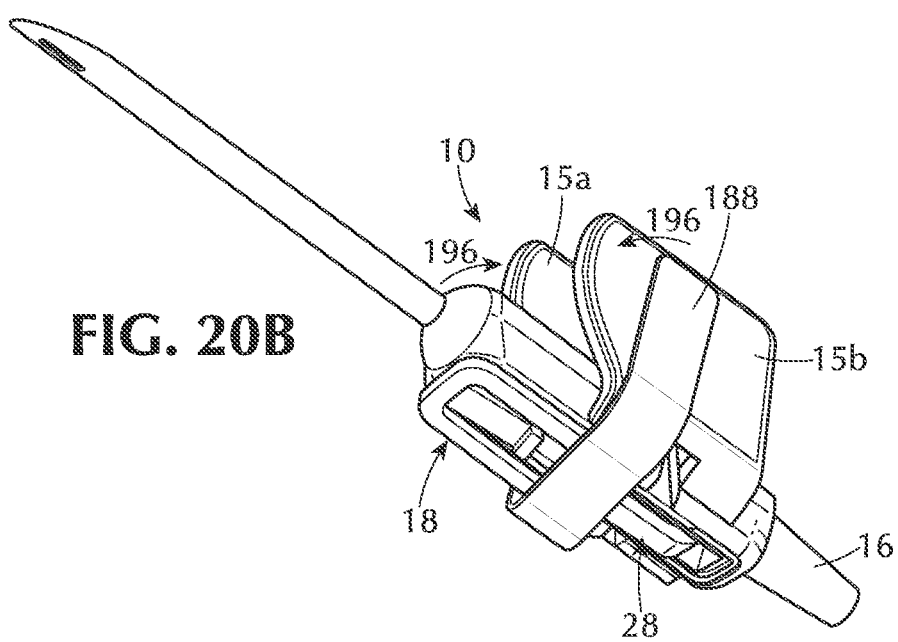

FIG. 20A illustrates that the sensor 18 can be in a closed position when the wings 15a and 15b are in a non-rotated position. For example, the sensor 18 can be in a closed position when the wings 15a and 15b extend substantially along the device second transverse axis A3. When the wings 15a and 15b are in a non-rotated position, the spring 26 can force the sensor 18 into a closed position. The strap 188 may or may not bias the wings into the configuration shown in FIG. 20A.

FIGS. 20B-20E illustrates that the wings 15a and 15b can be rotated (e.g., arrows 196) to extend substantially along the device first transverse axis A2, for example, during cannulation. When the wings 15a and 15b are in a rotated position, the strap 188 can overcome the tension of the spring 26 and force the sensor 18 into an open position, thereby keeping the flow path open during cannulation.

FIG. 20E further illustrates that the device can have the housing 14 and insert 17 structures as shown. FIG. 20E further illustrates that the membrane 54 can be opposite a housing protrusion 198. The housing protrusion 198 can extend at least partially toward a longitudinal center of the device flow channel 62 in the housing 14, for example, toward a longitudinal center of the flow path defined by the housing conduit 56. The occluder 32 can be configured to engage the housing protrusion 198 when the movable sensor 18 is in a closed configuration (e.g., when the device 10 becomes dislodged after cannulation).

FIG. 20F illustrates that the strap 188 can allow the sensor 18 to transition to a closed position when the device becomes dislodged from tissue. FIG. 20F further illustrates that the sensor 18 can be attached to the housing 14 via a hinge connection 144.

FIG. 20G illustrates that the membrane 54 can be forced against the housing protrusion 198 when the device 10 is in a dislodged configuration. FIG. 20G further illustrates the device 10 in a fully occluded configuration. FIG. 20G further illustrates that the spring distal end 26b can be integrated with or attached to the sensor distal end 18b. FIG.

20G further illustrates that the spring proximal end 26*a* can be curved to reduce the friction as the spring proximal end 26*a* slides along a surface of the spring guide recess 200.

Figure 20H:
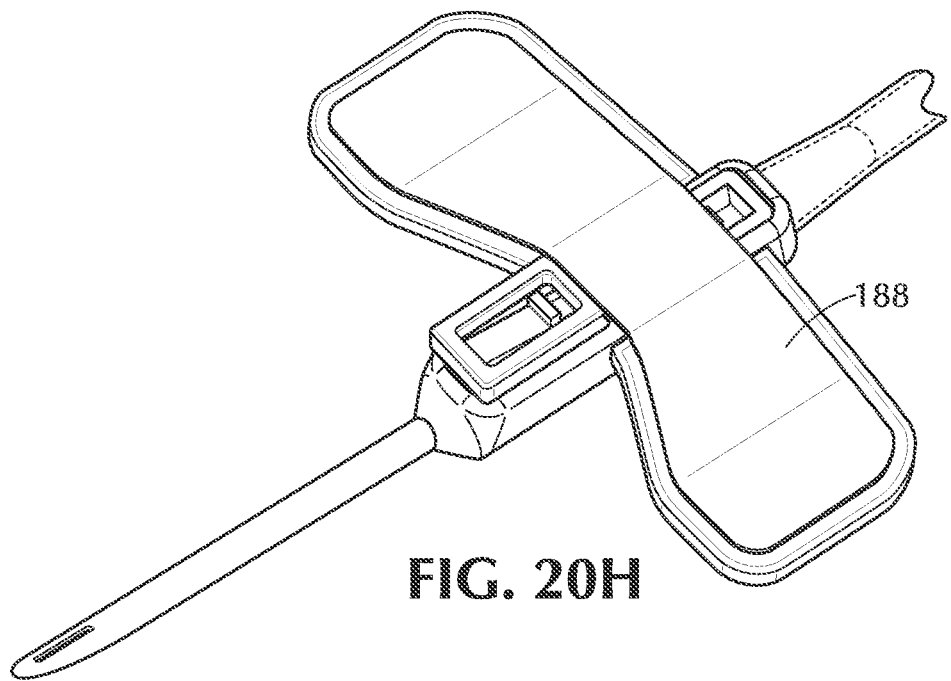

FIG. 20H illustrates another variation of the strap 188.

Figure 20I:
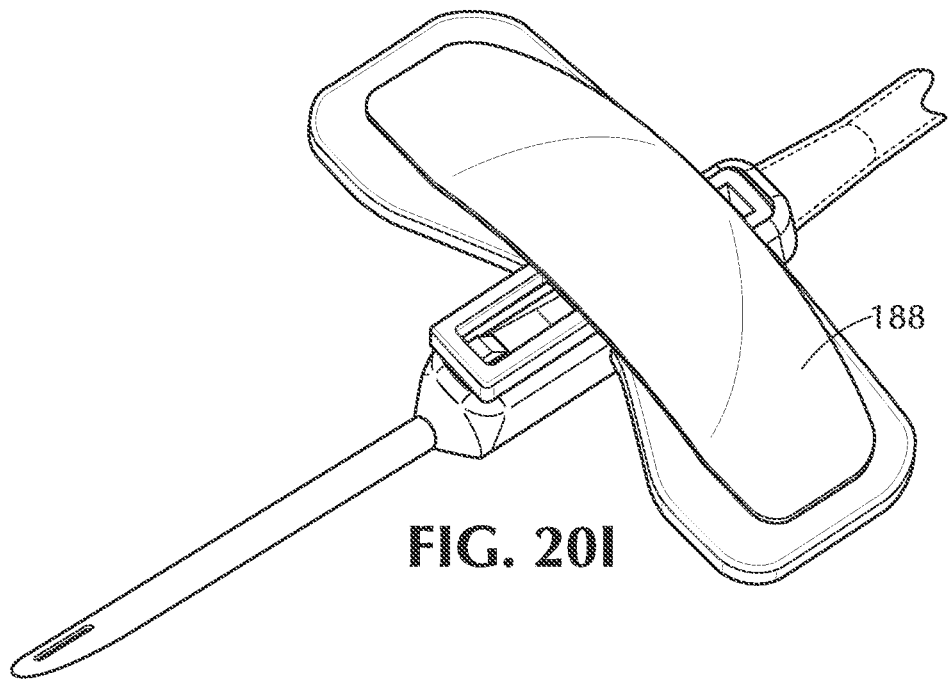

FIG. 20I illustrates another variation of the strap 188.

Figure 21D:
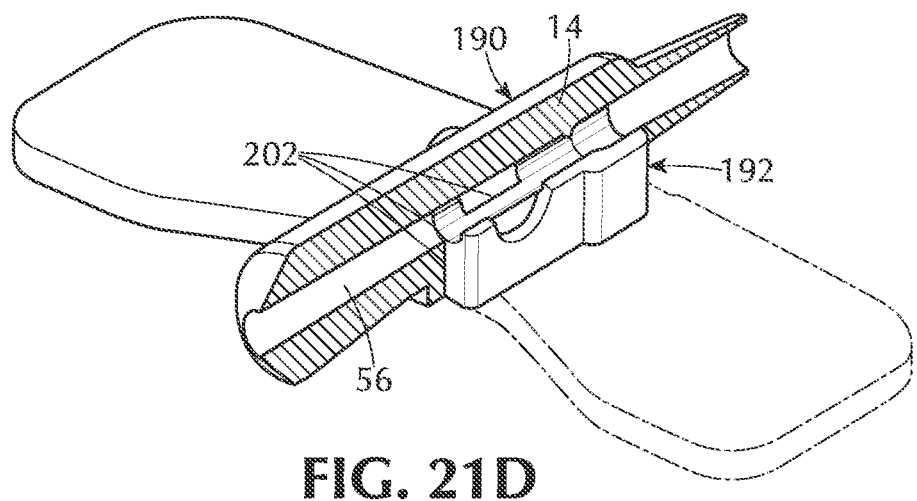

FIGS. 21A-21I illustrate that the device 10 can be manufactured using a two-shot mold process having a first-shot mold 190 and a second-shot mold 192. FIG. 21A illustrates a variation of the first-shot mold 190. The first-shot mold 190 can be molded with a single material or with a composite material. The first-shot mold 190 can include the needle wings 15*a* and 15*b* and part of the central body (e.g., part of the housing 14). FIG. 21B illustrates a variation of the second-shot mold 192. The second-shot mold 192 can be molded with a single material or with a composite material. The material of the second-shot mold 192 can be the same or different as the material of the first-shot mold 190. For example, the material of the second-shot mold 192 can be softer, more flexible, more resilient, more deformable, or any combination thereof, than the material of the first-shot mold 190. The second-shot mold 192 can be done within or outside of the needle wing/body unit (e.g., within the housing 14 defined by the first-shot mold 190). The second-shot mold 192 can be attached to the first-shot mold 190, for example, with glue, adhesive, and/or welds (e.g., sonic welds). The second-shot mold 192 can incorporate a compressible membrane (e.g., membrane 54). The compressible membrane can be a thin compressible membrane, for example, having a thickness of about 0.5 mm to about 2.0 mm, including every 0.1 mm increment within this range (e.g., 0.5 mm, 1.0 mm). The compressible membrane (e.g., membrane 54) can be a pinch point for the sensor 18 to act upon when the needle 12 is inadvertent withdrawn from the patient. The second-shot mold 192 can be the insert 17.

FIG. 21A illustrates that at least a portion of the housing 14 can define the housing conduit 56. FIG. 21A further illustrates that the first-shot mold 190 can include the protrusion 198.

FIG. 21B illustrates that at least a portion of the second-shot mold 192 can define the housing conduit 56.

FIG. 21C illustrates a variation of a sensor 18 being attached (arrow 183) to the housing 14 after the second-shot mold 192 is complete.

FIG. 21D illustrates that the first-shot and second-shot molds 190, 192 can be attached to maintain a fluid tight seal 202. The fluid tight seal 202 can withstand the high flow pressures associated with hemodialysis treatment. FIG. 21D illustrates that at least a portion of the first-shot mold 190 (e.g., the housing 14) and at least a portion of the second-shot mold 192 (e.g., the insert 17) can define the housing conduit 56. The first-shot and second-shot molds 190, 192 can together define the housing 14.

Figure 21E:
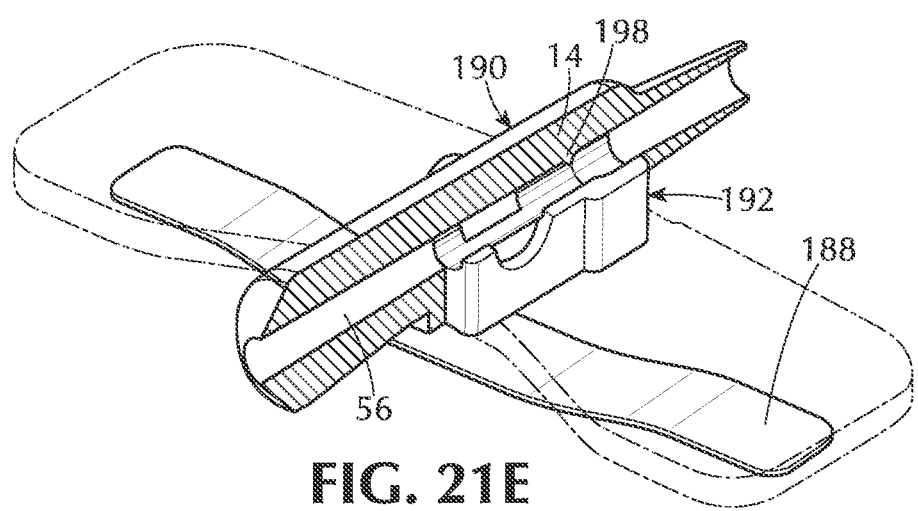

FIG. 21E illustrates the strap 188 relative to the first-shot and second-shot molds 190, 192.

FIGS. 21F and 21G illustrate the two-shot mold manufacturing process 204 for the first-shot mold 190 (FIG. 21F) and the second-shot mold 192 (FIG. 21G).

Figure 21H:
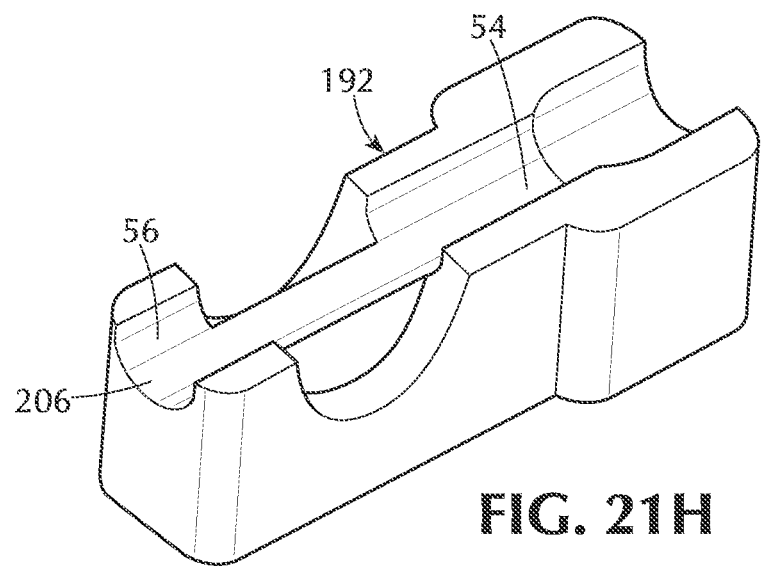
Figure 21I:
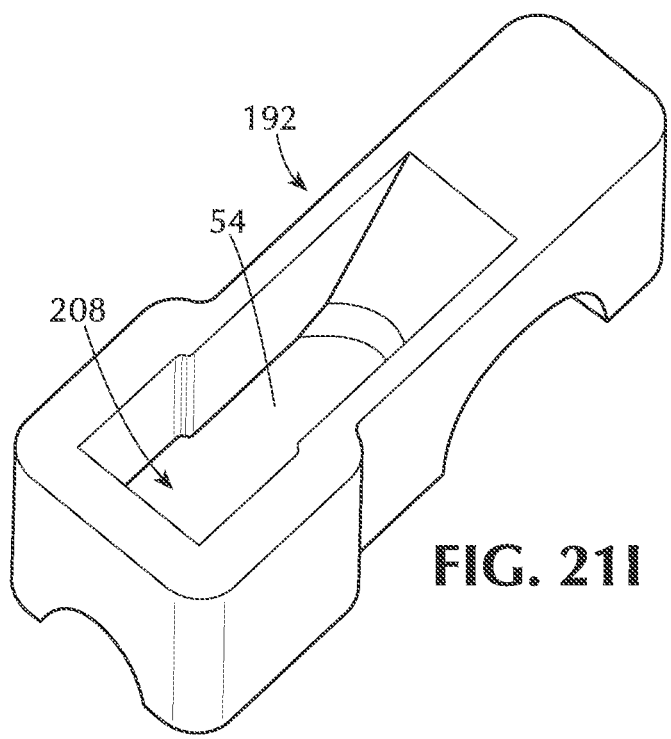

FIGS. 21H and 21I illustrate a variation of the second-shot mold 192. FIG. 21H illustrates that the second-shot mold 192 can have surface 206 that at least partly defines the housing conduit 56. FIG. 21H further illustrates a variation of the location of the membrane 54 on the insert 17 (also referred to as the second-shot mold 192). FIG. 21 illustrates that the second-shot mold 192 can have a recess 208 for the flow restrictor 28 to move in. The recess 208 can give the sensor 18 access to the housing conduit 56 by allowing the occluder 32 to deflect the membrane 54 toward the protrusion 198, for example, when the sensor moves from an open position to a closed position.

FIGS. 10A, 10B, 13A-13E, 14A, 14B, 20A-20I and 21C further illustrate that the sensor 18 can have a straight sensor distal end 18*b*. FIGS. 10A, 10B, 13A-13E, 14A, 14B, 20A-20I and 21C further illustrate the sensor distal end 18*b* without a curve 21.

Figure 22A:
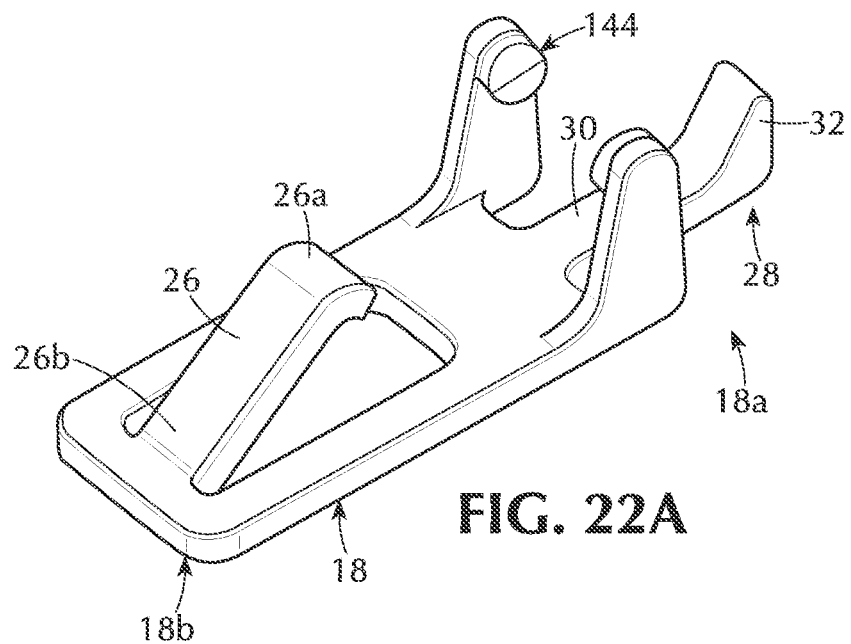
FIGS. 22A and 22B illustrate various views of the sensor of FIGS. 20A-20G.
Figure 22B:
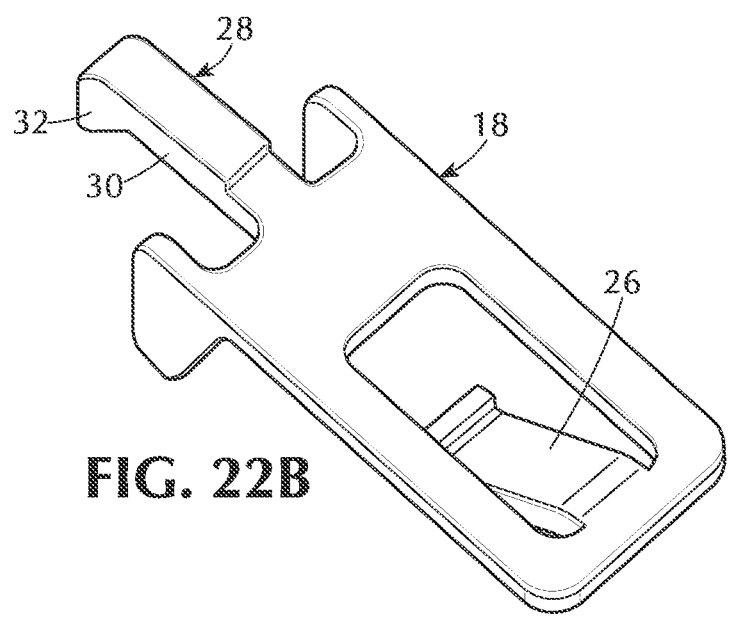

FIGS. 22A and 22B illustrate that the sensor 18 can have the features shown.

Figure 23A:
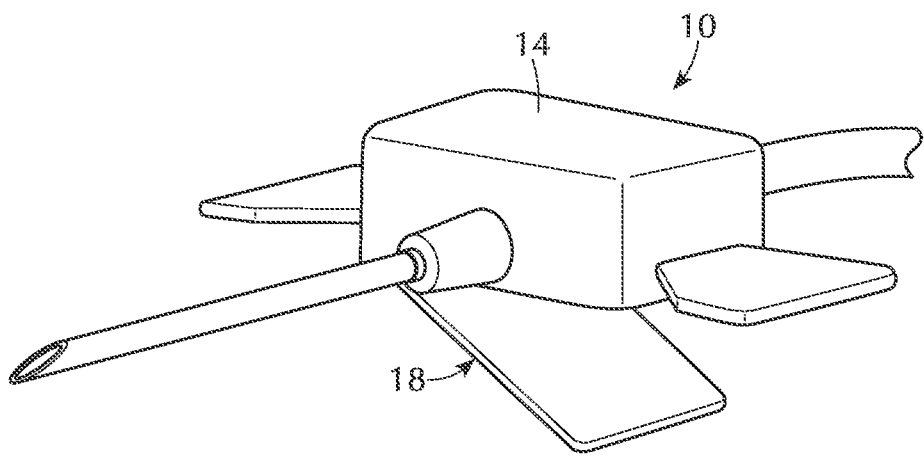
FIGS. 23A and 23B illustrate a variation of a tissue access device.
Figure 23B:
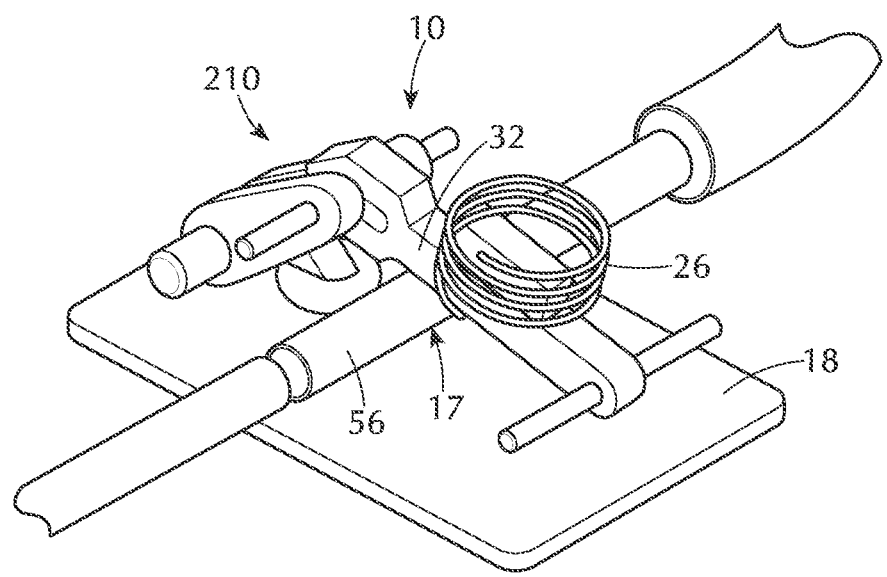

FIGS. 23A and 23B illustrate a variation of a spring loaded member 32 (also referred to as an occluder) that pushes from above when induced by a blade mechanism 18 (also referred to as a sensor) that pivots against the skin in a direction lateral to that of the fluid flow. The linkage assembly 210 works to push the member 32 against a compressible tube 17 (labeled as 17 because the compressible tube can be an insert) which acts to block the flow path through the needle. The spring loaded member 32 can be spring loaded with spring 26. FIG. 23A illustrates the device 10 in an occluded configuration and FIG. 23B illustrates the device 10 in a non-occluded configuration.

Figure 24A:
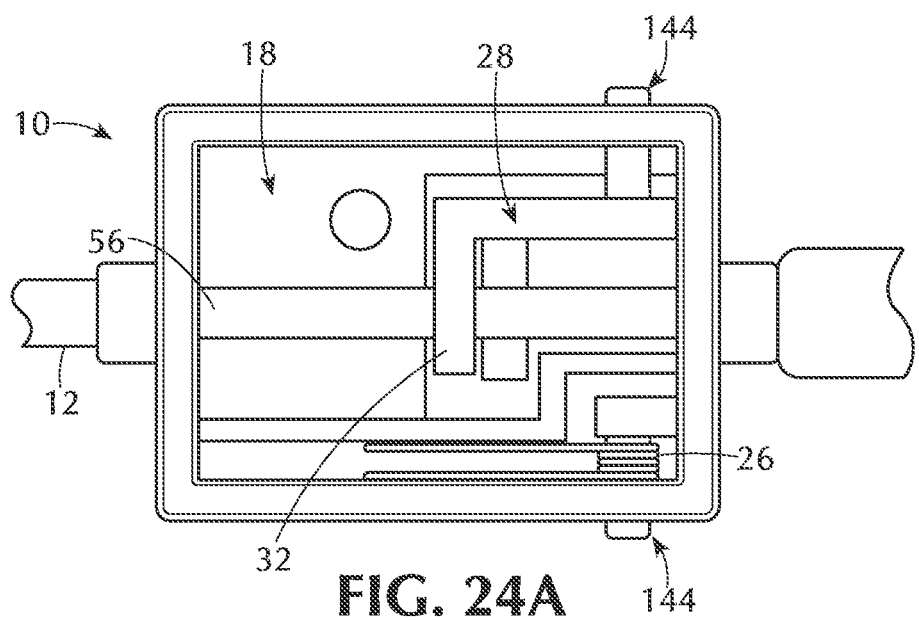
FIGS. 24A and 24B illustrate a variation of a tissue access device.
Figure 24B:
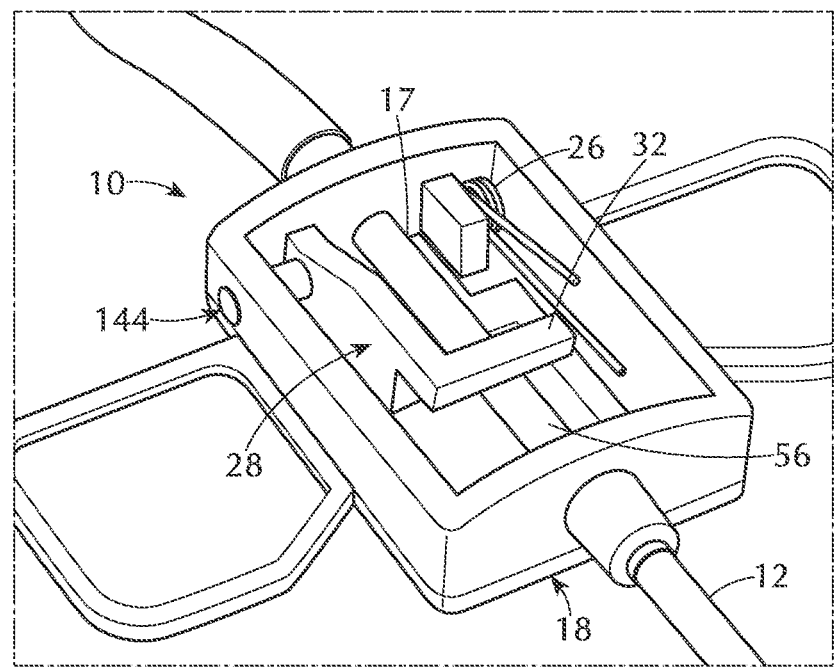

FIGS. 24A and 24B illustrate a variation of a skin sensing blade mechanism 18 hinged such that the direction of motion is in the same direction as the flow path. Like FIGS. 23A and 23B, an assembly linkage pushes a member 32 with structural integrity against a compressible internal tube 17 to block flow through the needle when the skin sensing blade 18 is permitted to swing open during dislodgement. For example, the assembly linkage can push the member 32 against the compressible internal tube 17 to block flow through the needle when and only when the skin sensing blade 18 is permitted to swing open during dislodgement. The member 32 can be spring loaded with spring 26. The sensing blade can rotate about the hinge connection 144. FIGS. 24A and 24B illustrate the device 10 in a non-occluded configuration.

Figure 25A:
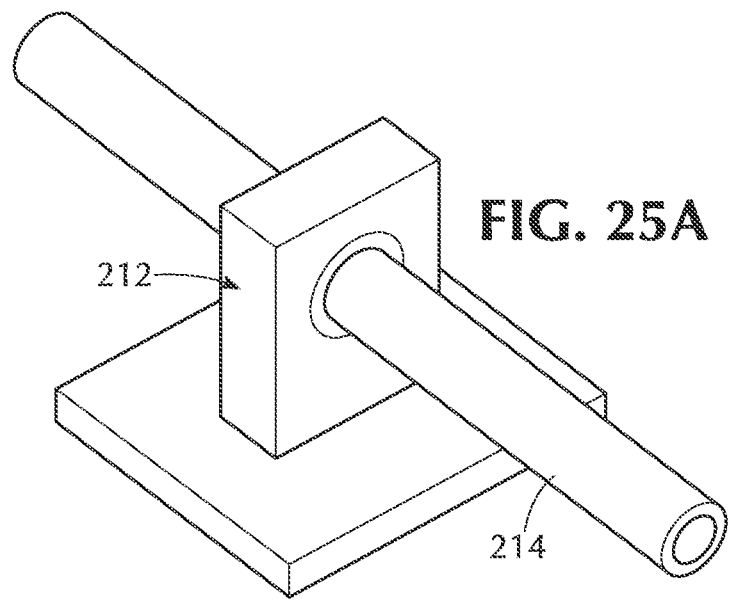
FIGS. 25A-25D illustrate a variation of a flow restrictor.
Figure 25B:
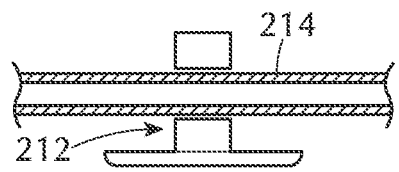
Figure 25C:
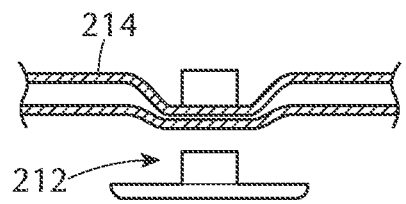
Figure 25D:
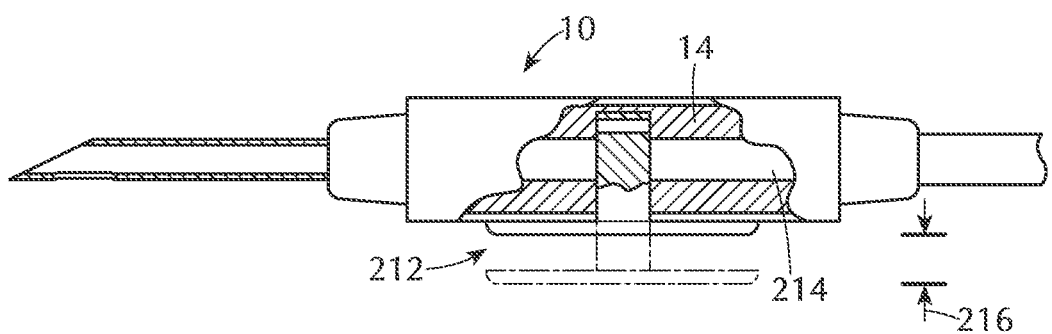

FIGS. 25A-25D illustrate a variation of a button-like skin sensing actuator 212 (also referred to more generally throughout as a flow restrictor 28) with a central through-hole that dictates flow status depending on the position of the through-hole relative to an internal flow path 214. When the central piston 212 is aligned (e.g., partially or entirely) with the through-hole next to the internal flow path 214, flow can proceed through internal flow path 214. This system stops flow whenever the needle is dislodged. For example, only when the central piston 212 is aligned with the through-hole next to the internal flow path will the flow proceed. The base of the piston 212 can be a sensor 18. FIG. 25B illustrates the sensor (e.g., sensor 18) against the skin and the actuator 212 in an open configuration with the through-hole of the actuator 212 aligned with the flow path 214. FIG. 25C illustrates the sensor off the skin and the actuator 212 in a closed configuration with the through-hole of the actuator 212 misaligned with the flow path 214, resulting in the flow path 214 being occluded. FIG. 25D illustrates a variation of the device 10 having the actuator 212. FIG. 25D further illustrates that the actuator 212 can fully occlude the flow path 214 when device 10 is dislodged and the skin sensor moves away from the bottom surface of the device by a dimension 216. The dimension 216 can be, for example, about 5 mm to about 25 mm, including every 1 mm increment within this range (e.g., 8 mm, 10 mm, 15 mm, 15 mm).

Figure 26:
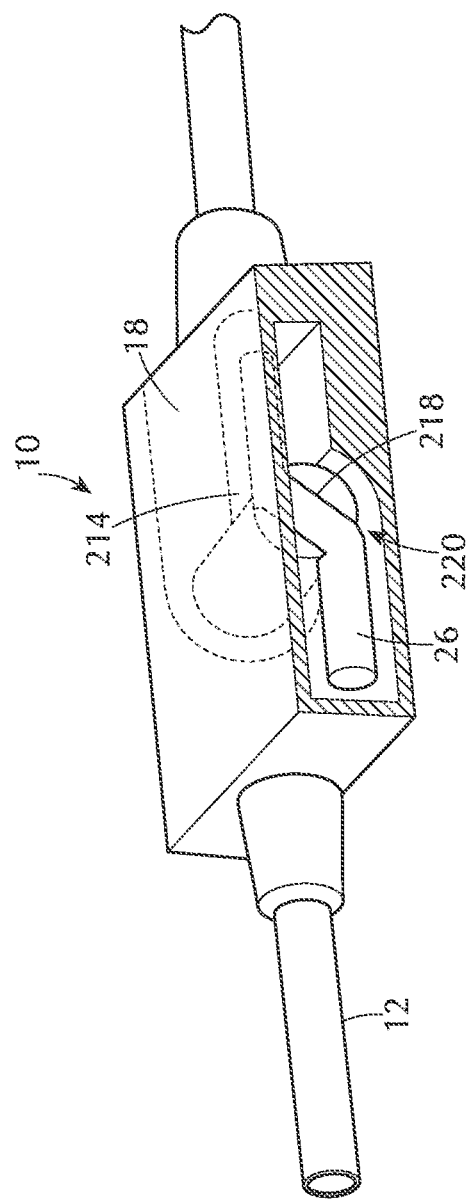
FIG. 26 illustrates a variation of a flow restrictor.

FIG. 26 illustrates a variation of a flow restrictor 28. For example, FIG. 26 illustrates an internal rotary mechanism 220 that is linked to an armature 18 that acts as the skin sensor. A compressible tube 214 allows fluid flow through the needle when the skin sensor 18 is placed in a position against the skin. For example, the compressible tube 214 can allow fluid flow through the needle only when the skin sensor 18 is placed in a position against the skin. During dislodgement a spring 26 rotates an internal flow block mechanism 220 and acts on a compressible tube 214, blocking off fluid flow. The spring member 26 is shown in a "z-like" position as the needle is pressed tight against the skin. This spring will straighten during dislodgement, creating the flow blockage. The spring 26 can be in a channel 218 of the rotary mechanism 220.

FIG. 27 illustrates a variation of a cut away side view of a fluid flow control technique that is created via compression of a soft side wall 214 in an embedded flow path 56 within the needle body 14. This flow control mechanism avoids the need for placement of an internal compressible tube during manufacture. FIG. 27 illustrates the occluder 32 occluding the compressible tube 214, for example, when the device 10 becomes dislodged from tissue.

Figure 28F:
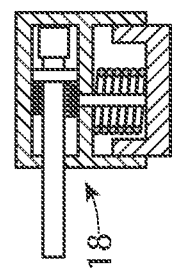
Figure 28D:
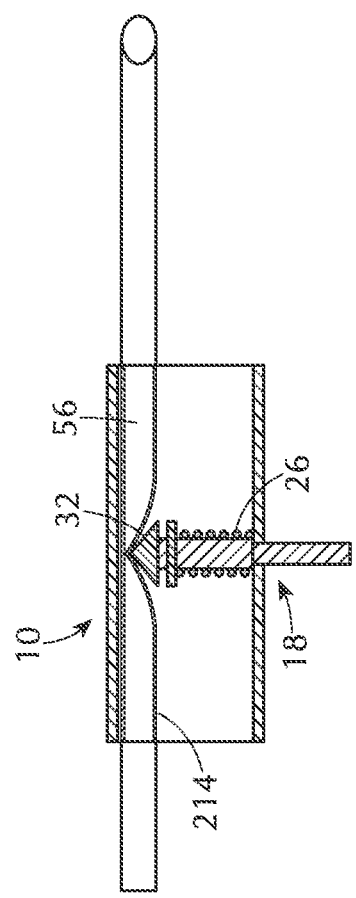
Figure 28E:
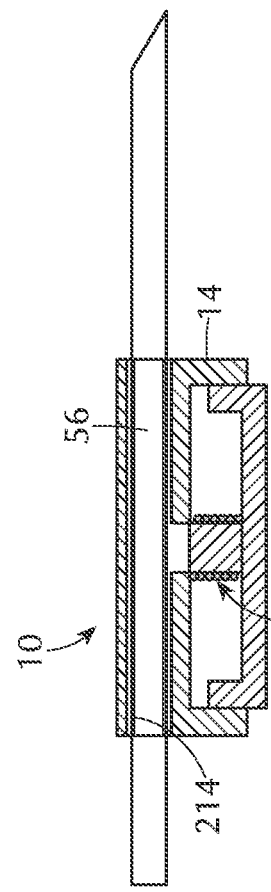

FIGS. 28A-28F illustrate multiple views of a dual flow control actuation system that results in flow blockage or passage based on a skin sensor 18 in which flow is blocked from compression from the bottom of a soft tube 214. With this technique a secondary actuator is used to block off fluid flow after an initial actuator is triggered by dislodgement. FIGS. 28A-28C illustrate an open flow path and FIGS. 28D-28F illustrate an occluded flow path.

Figure 29:
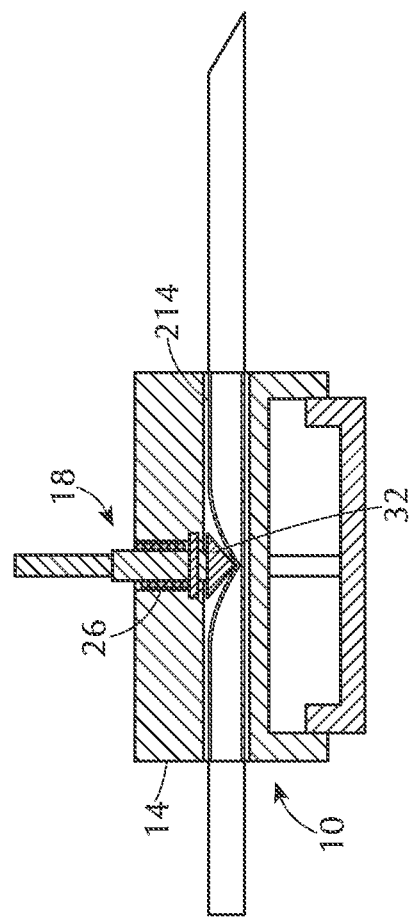
FIG. 29 illustrates a variation of a flow restrictor.

FIG. 29 illustrates a flow control mechanism in which flow is blocked by actuation delivered through the top of a compressible tube 214. In this variation, the sensor 18 used for skin-sensing is integrated into the body of the needle (e.g., housing 14) providing mechanical stabilization and protection.

FIGS. 30A-30D illustrate a side cut away view of a diaphragm and pin technique to block flow during dislodgement. The skin-sensor blade 18 uses an actuator 26 to press a molded pin 32 into the flow path 56, blocking flow during dislodgement. The actuator 26 in FIG. 30 is a spring 26, which rises and falls with the skin-sensor blade 18. The pin 32 can be integrated with a diaphragm valve 222. The valve 222 can be connected to the spring 26 such that the valve 222 rises and falls with movement of the spring 26. The spring 26 can be anchored to the housing via a spring anchor 224.

Figure 31:
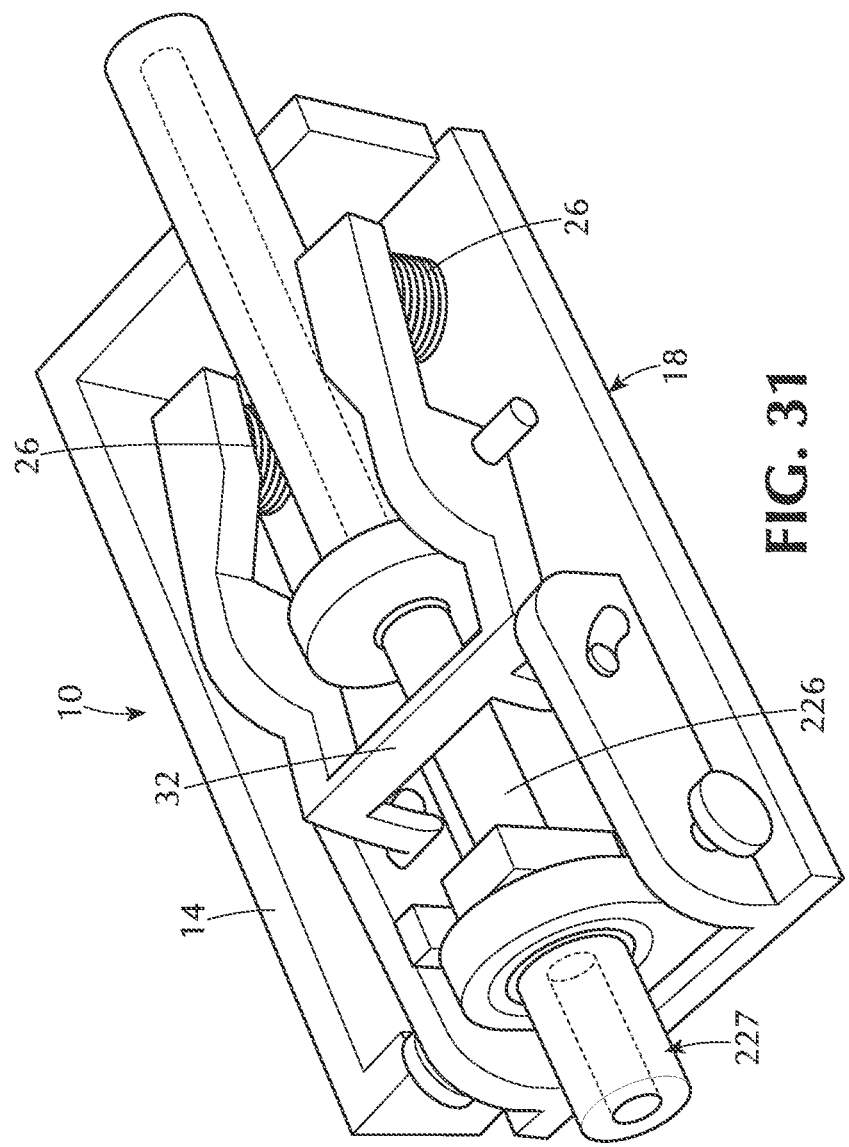
FIG. 31 illustrates a variation of a multi-component system.

FIG. 31 illustrates an internal view showing a drop-in formed soft tube 226 that is pinched during dislodgement via the occluder 32 to stop flow by a lever system powered by springs 26. Drop in tubes may result in decreased manufacturing costs. A needle attachment point 227 for outgoing flow is also shown.

Figure 32A:
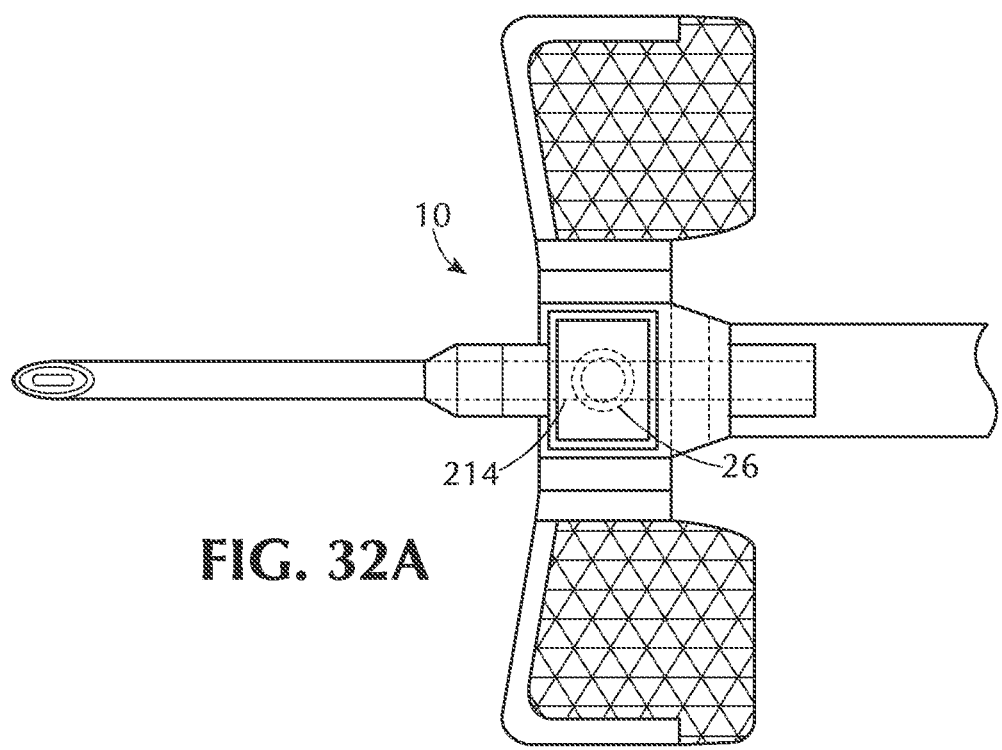
FIGS. 32A and 32B illustrate a variation of a tissue access device.
Figure 32B:
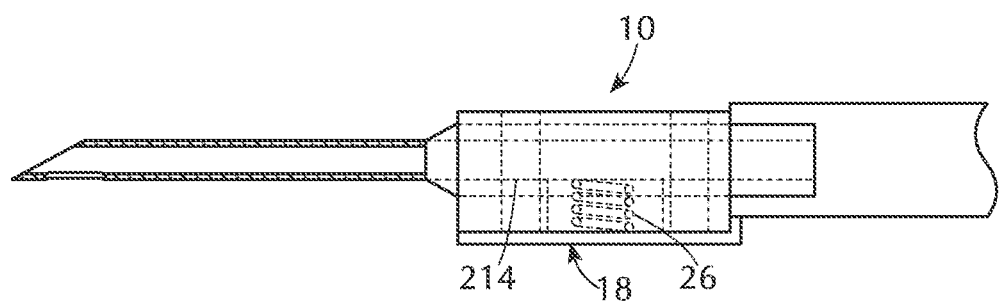

FIGS. 32A and 32B illustrate a device 10 that stops flow during dislodgement based on a bottom skin-sensing footplate 18 that detects dislodgement and a loop piece which compresses a soft tube via a central helical spring 26.

Figure 33A:
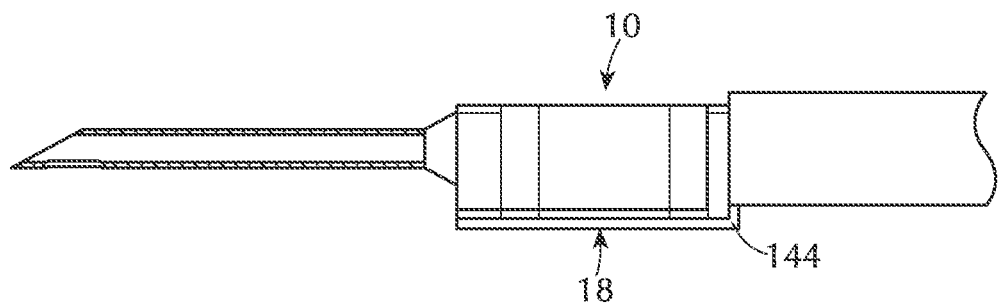
FIGS. 33A and 33B illustrate a variation of a tissue access device.
Figure 33B:
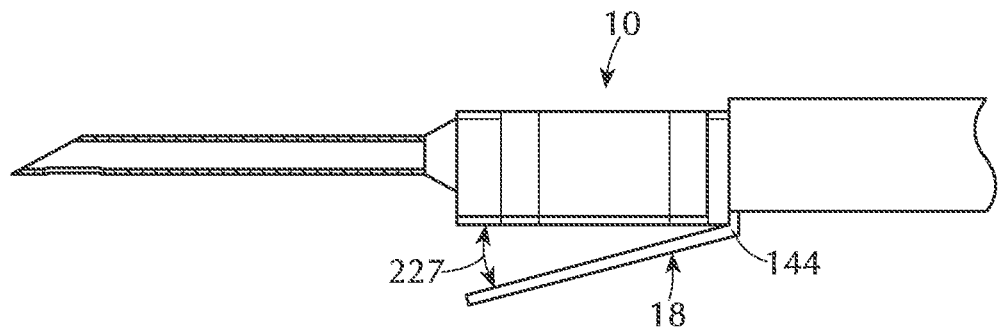

FIGS. 33A and 33B 18 illustrate a device 10 having a blade-like skin sensing system 18 for dislodgement protection. Like the mechanism in FIGS. 32A and 32B, it uses a central helical spring 26 to move a wire loop that is used to block flow during dislodgement. FIGS. 33A and 33B further illustrate that the hinge 144 can be a polymer hinge. FIG. 33B further illustrates that the sensor 18 can rotate away from the bottom of the device an angle 227. The angle 227 can range, for example, from about 10 degrees to about 45 degrees or more, including every 1 degree increment within this range (e.g., 15 degrees, 20 degrees, 30 degrees).

Figure 34A:
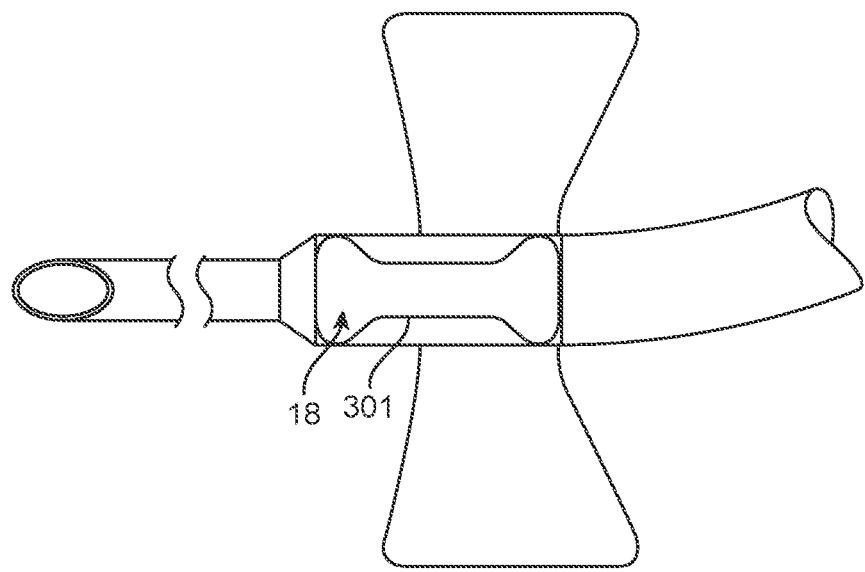
FIGS. 34A and 34B illustrate variations of sensors.
Figure 34B:
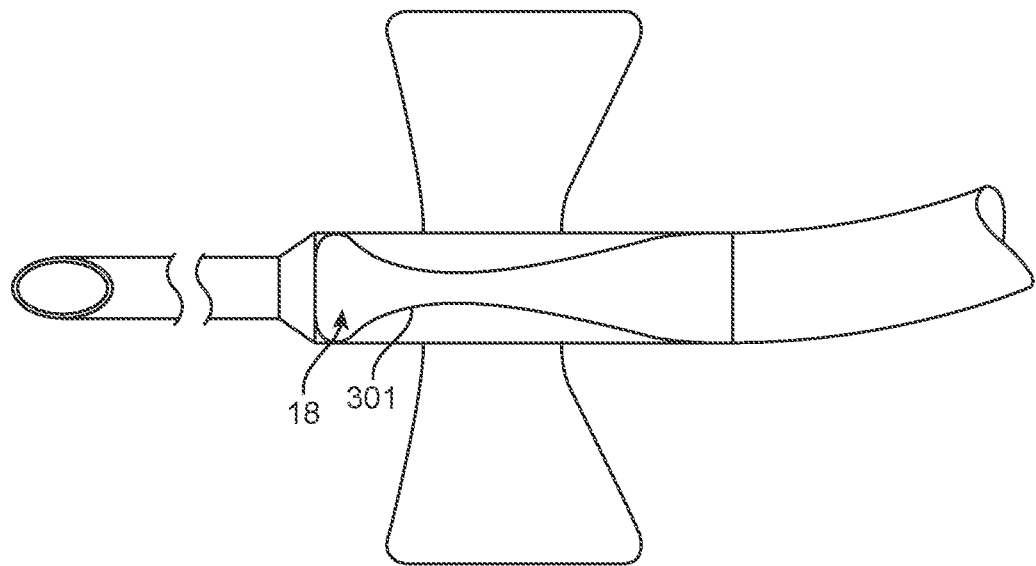

FIGS. 34A and 34B illustrate a bottom view of how a blade can be modified to better prepare it for certain dislodgement features (e.g., via the scooped sides 301 or differing lengths). For example, the sensor 18 in FIG. 34A is shorter than the sensor 18 in FIG. 34B. FIGS. 34A and 34B illustrate that the sensors 18 can have scooped sides/edges 301.

Figure 35A:
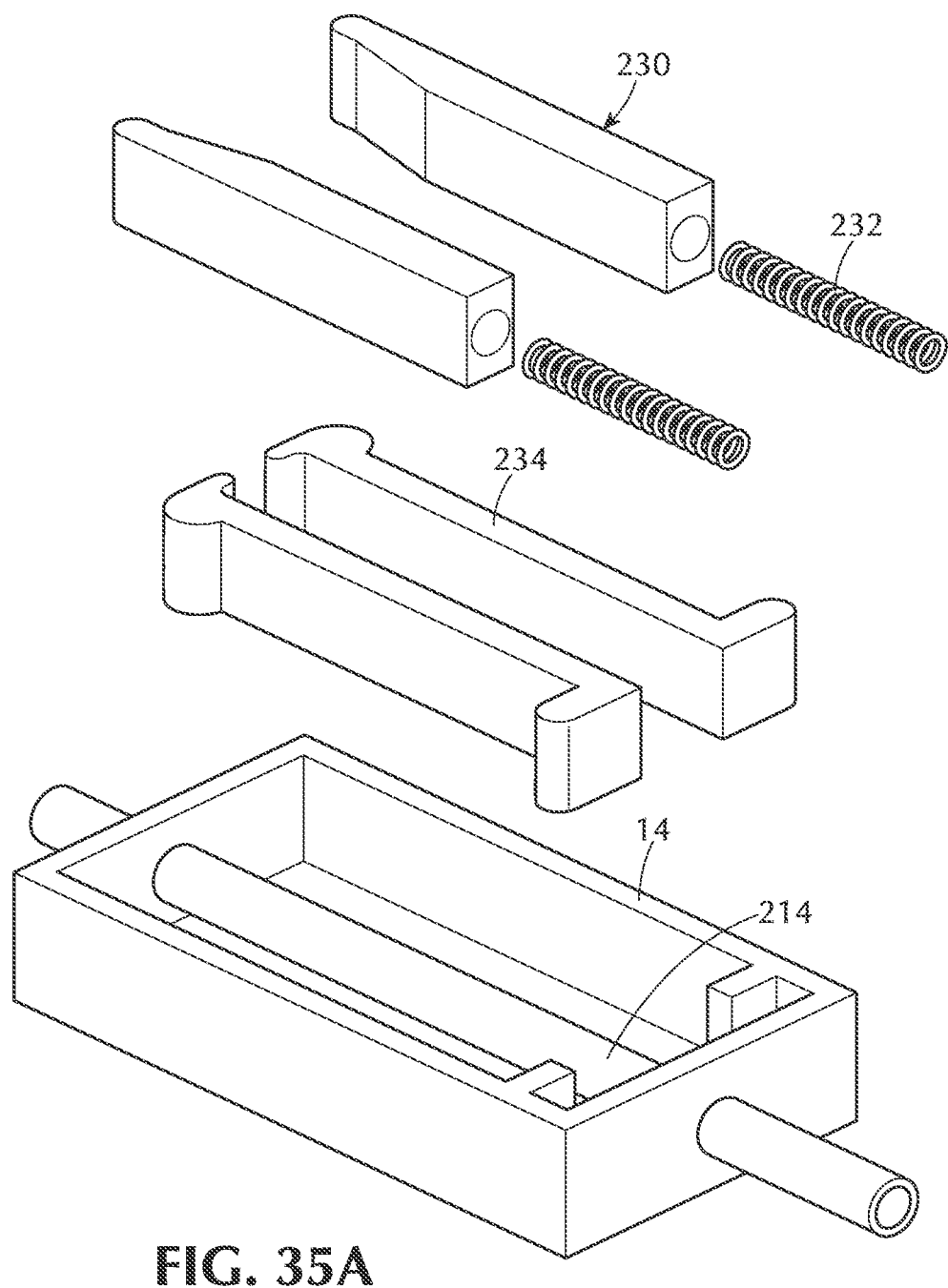
Figure 35B:
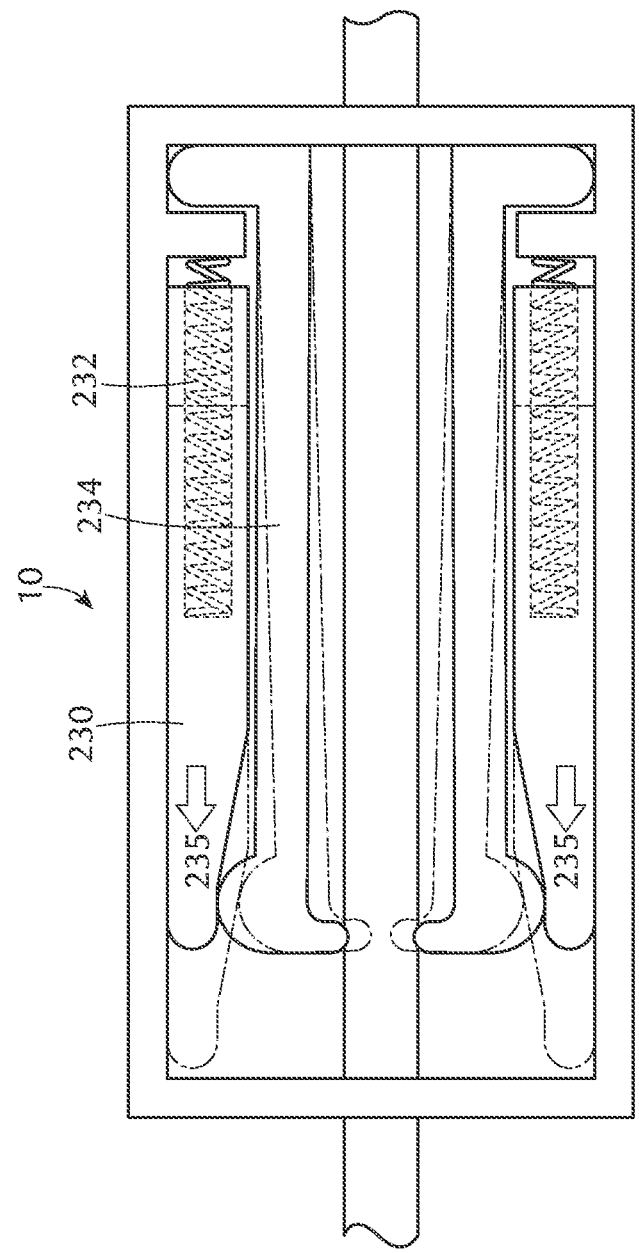

FIGS. 35A-35C illustrate a tube pinching system in which sliders 230 are used in combination with pinch arms 234 to pinch an internal tube 214 upon dislodgement. The system can also have springs 232. FIG. 35A illustrates an exploded view of the tube pinching system. FIG. 35B illustrates that the springs 232 can push the sliders 230 in direction 235 to force the pinch arms 230 toward the tube 214 to pinch the tube 214. The dashed lines in FIG. 35B illustrate this movement. This system also benefits from drop-in components for ease and lower cost of manufacture.

Figure 36A:
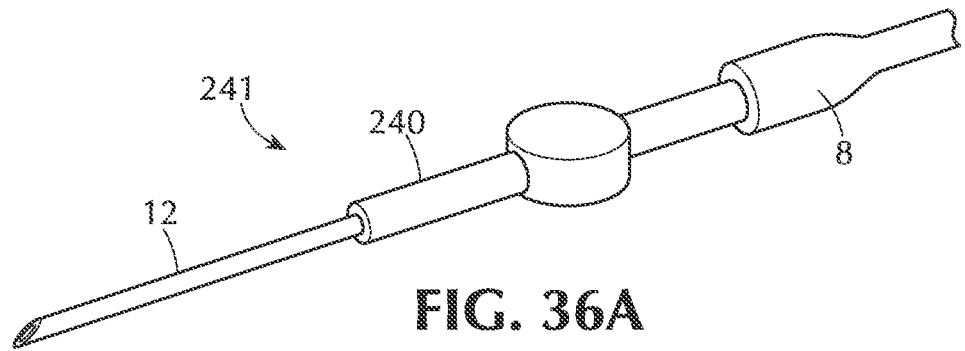
FIGS. 36A and 36B illustrate a variation of a drop-in component.
Figure 36B:
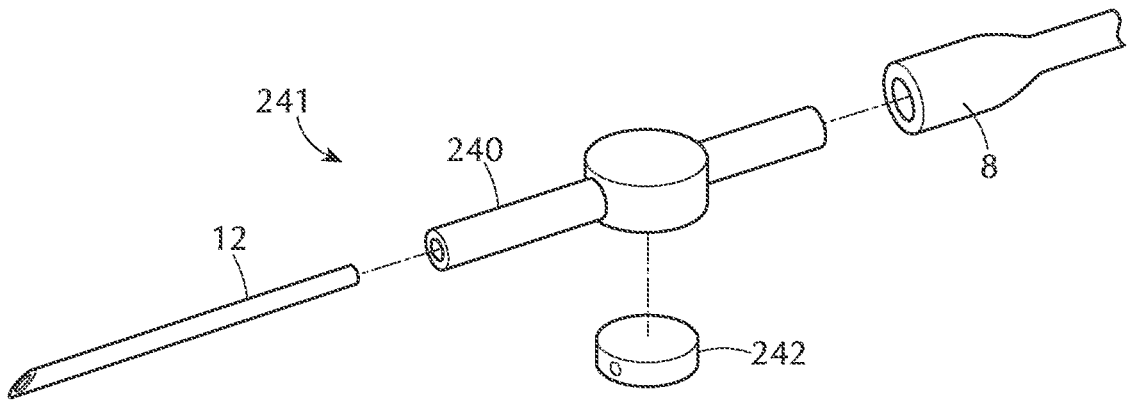
Figure 36C:
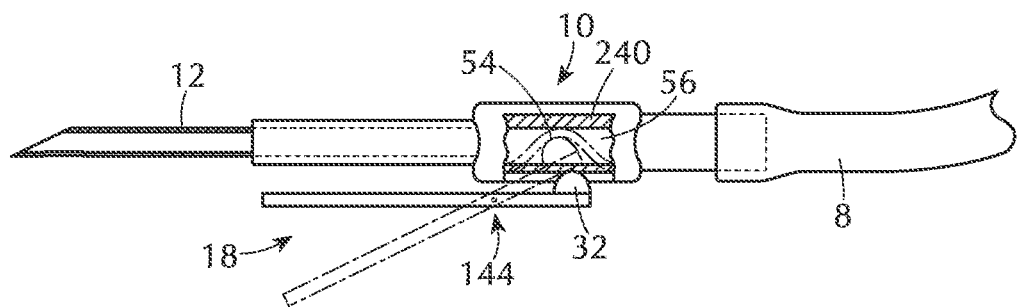
FIG. 36C illustrates a variation of a tissue access device.

FIG. 36A illustrates a hybrid version of a drop-in component 241 having a needle 12 and a body 240 connectable to the tube 8. FIG. 36B illustrates that the component 241 can have a shut-off valve 242. FIG. 36C illustrates a blade/diaphragm system that is made to closely resemble an actual needle and will stop fluid flow upon dislodgement using the dislodgement mechanisms described herein.

FIGS. 37A-37C illustrate a variation of an insert 17 configured to support flow stoppage during dislodgement. It uses a molded through-path 56 with a thinned wall 54 to act as a closing point for a structural assembly that is part of or linked to a blade skin-sensing arm 18. FIG. 37A illustrates a device 10 with the drop-in component 241. FIG. 37B illustrates a longitudinal cross-sectional view of the insert 17 in an open configuration. FIG. 37C illustrates a transverse cross-sectional view of the insert 17 in an open configuration. FIG. 37C further illustrates that the through-path 56 can be closed by applying a force 249 against the membrane 54.

Figure 38A:
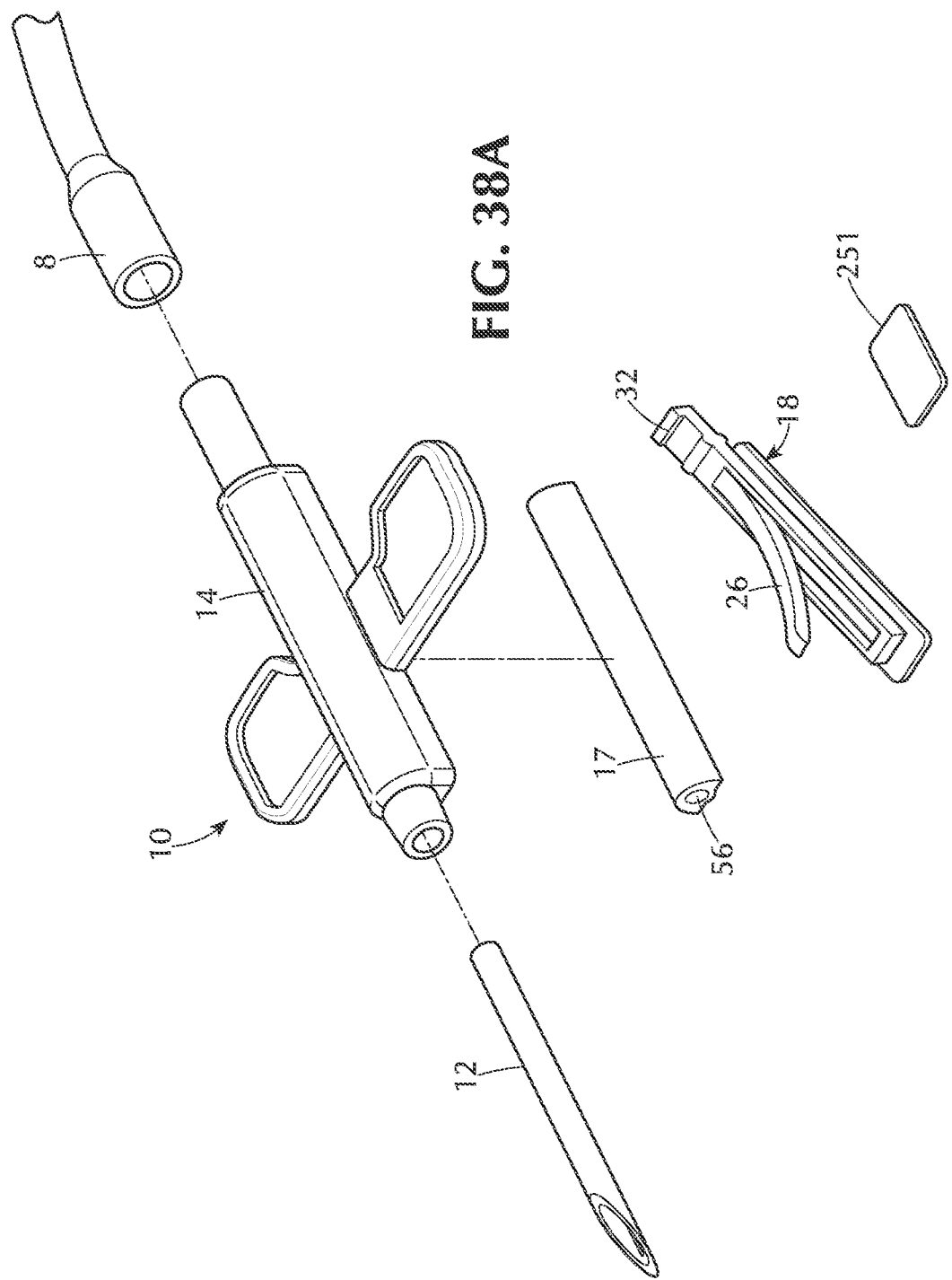
FIGS. 38A-38F illustrate a variation of a tissue access device and components thereof.
Figure 38B:
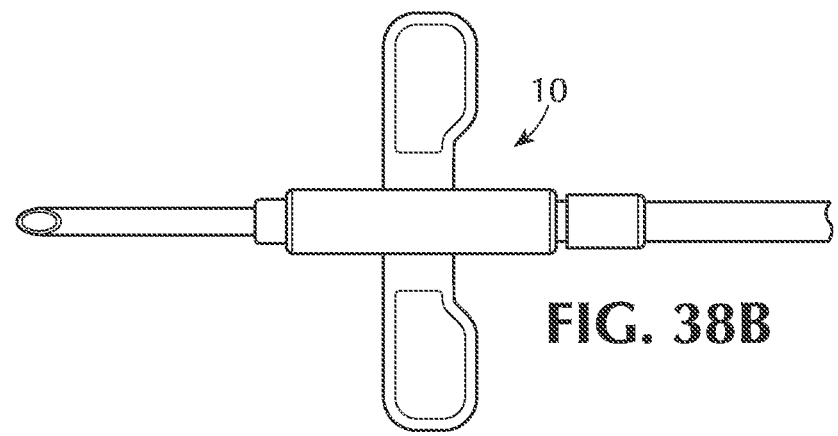
Figure 38C:
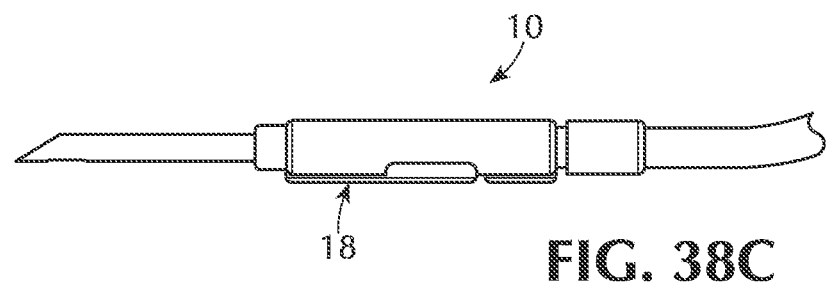
Figure 38D:
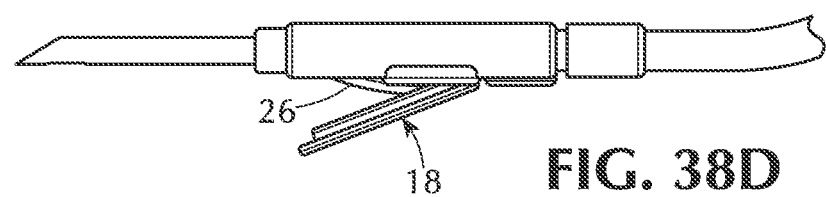
Figure 38E:
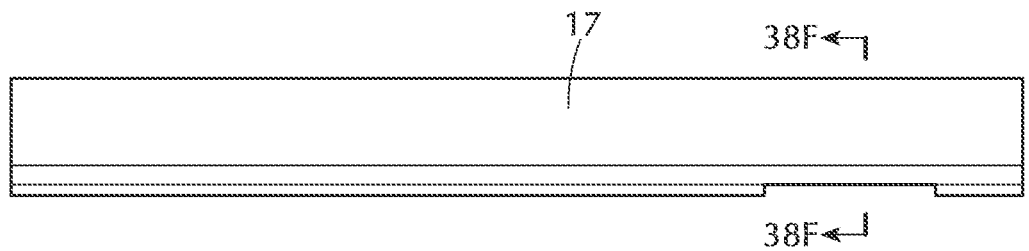
Figure 38F:
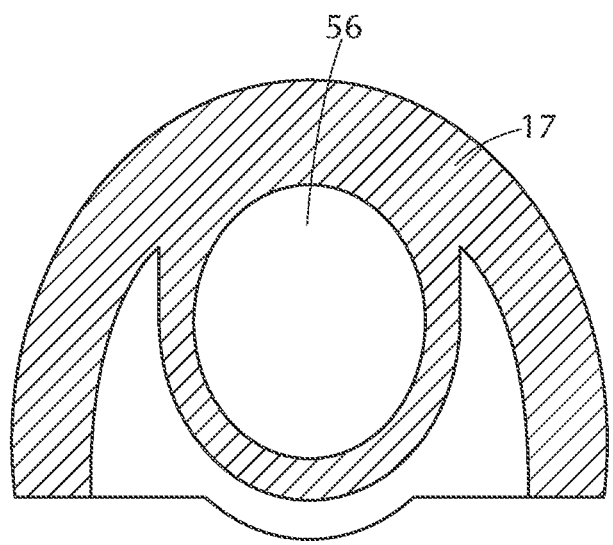
Figure 39A:
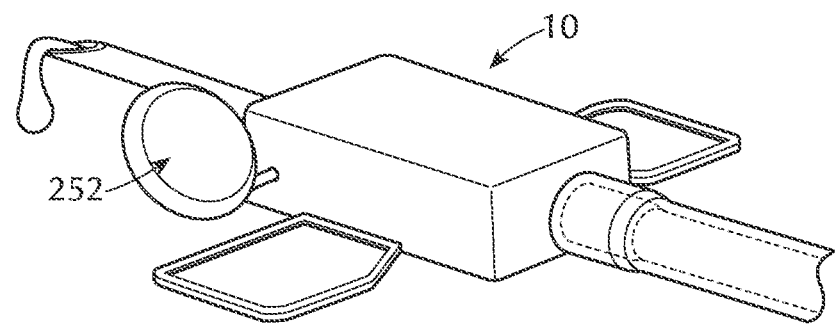
FIGS. 39A-39C illustrate a variation of a flow control mechanism.
Figure 39B:
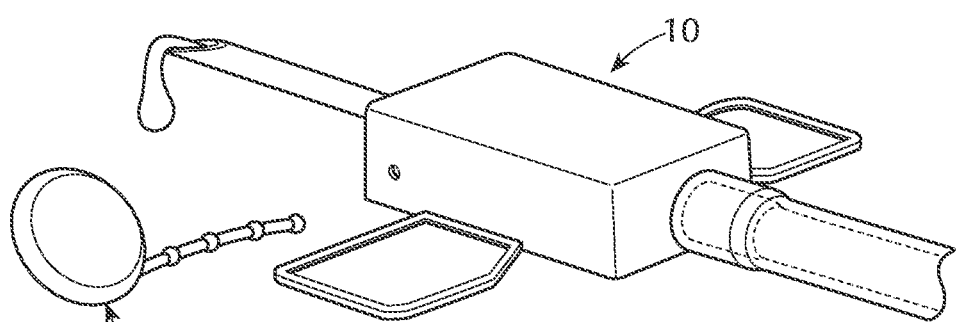
Figure 39C:
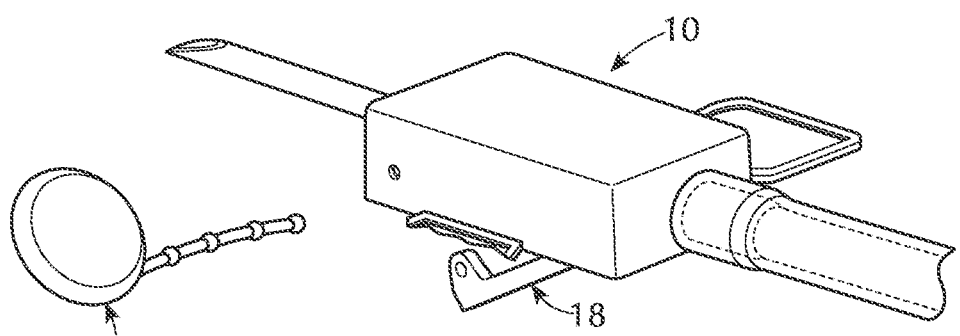

FIGS. 38A-38F illustrate a variation of a device 10 having an insert 17 defining a housing conduit 56. A finishing cap 251 can be placed over a proximal end of the spring 26. FIG. 38C illustrates the device 10 in an attached configuration. FIG. 38D illustrates the device 10 in an occluded configuration, with the spring 26 forcing the distal end of the sensor 18 away from the flow path 56 and the occluder 32 into the membrane 54 to close the flow path.

Figure 40A:
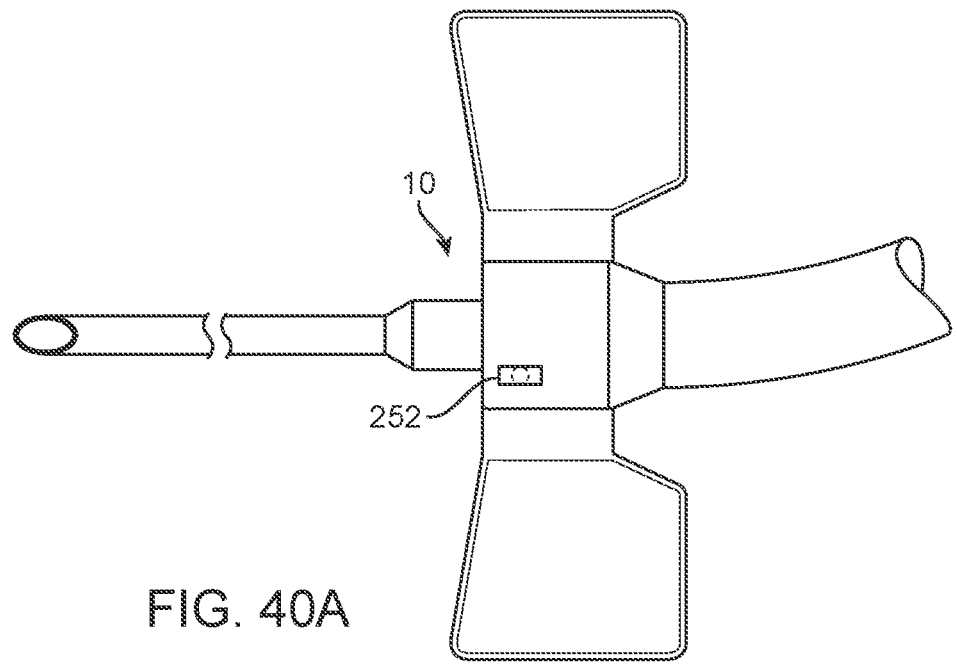
FIGS. 40A-40C illustrate a variation of a flow control mechanism.
Figure 40B:
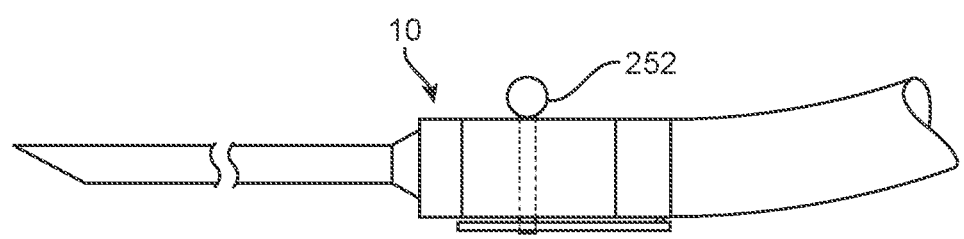
Figure 40C:
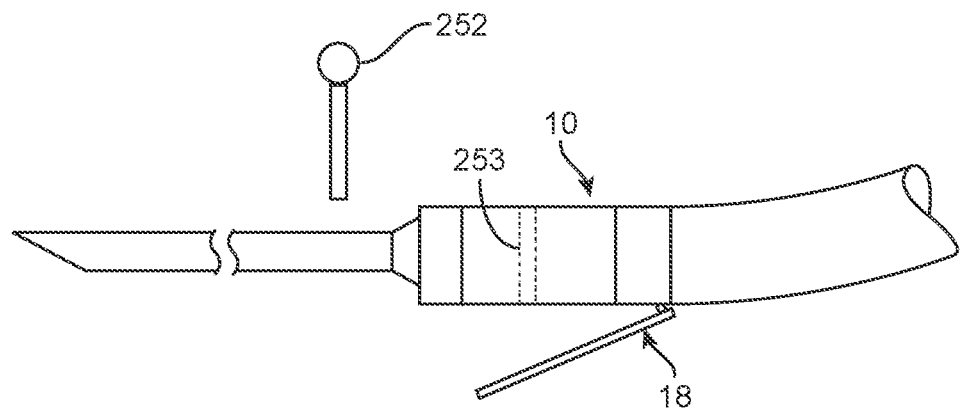

FIGS. 39A-39C and 40A-40C illustrate two variations of a manual actuation pin 252 which can be pulled by a user when the needle dislodgement mechanisms are to be actively engaged. Users would cannulate the patient first before pulling the pin 252. With the pin 252 in the device 10, the flow path is always on (flow path is open). The pin 252 insures that the mechanism for blocking the flow path through the needle cannot be activated, which can be useful, for example, during cannulation. The pins 252 can be snapped, slid, and/or threaded into and/or out of the device 10. The pin 252 can be positioned at any point within the structure and take any number for forms (e.g., pin, plug, ribbon, collar, screw). Pulling the pin 252 would allow for any of the dislodgement mechanisms disclosed herein to become active for the duration of fluid delivery therapy. The pin 252 can also take the form of a collar wrapped around the standard tubing connected to the needle body 14. Such a position would maximize the ability of the pin 252 to be accessed by clinical staff within the standard needle taping regimen. As another example, the pin 252 can also take the form of a ribbon or mechanical assembly that runs underneath the needle body and tubing as a means to avoid being taped over during insertion. When the pin 252 is in the device 10, the sensors 18 can be prevented from activating such that the flow path is always open (e.g., FIGS. 39A and 40A). When the pin 252 is removed from the device 10, the sensor 18 can become active such that the flow path is open only while the needle remains attached (e.g., FIGS. 39B and 40B). When the pin 252 is removed and the needle becomes dislodged, the sensor 18 can actuate and close the flow path (e.g., FIGS. 39C and 40C). FIG. 40C illustrates that the housing 14 can have a pin channel 253 for the pin 252.

Figure 41A:
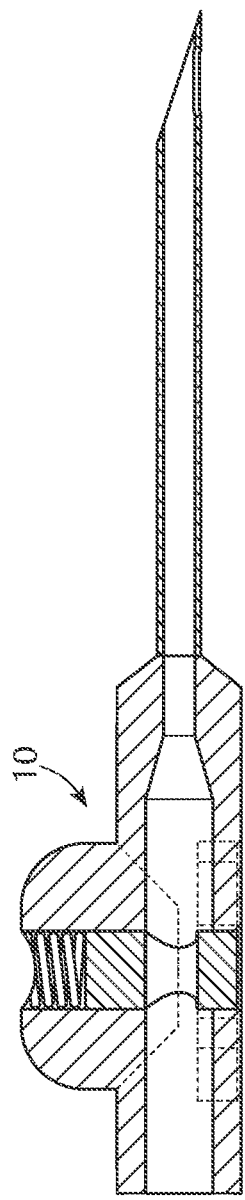
FIGS. 41A and 41B illustrate a variation of a flow control mechanism.
Figure 41B:
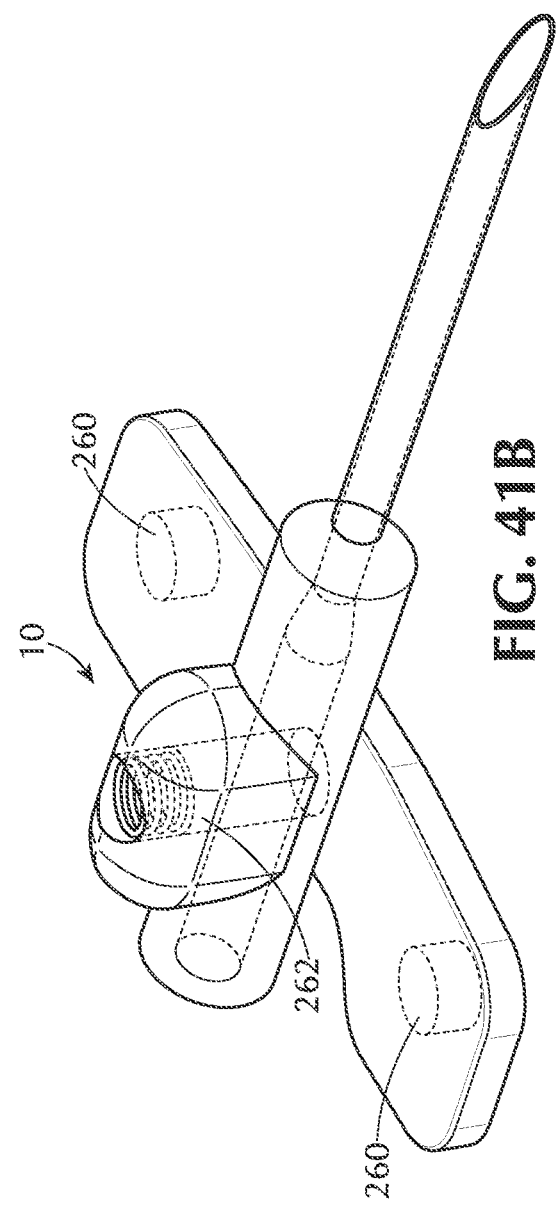

FIGS. 41A and 41B illustrate a multi-magnet system that provides the needle 12 with a built in mechanism to automatically insure fluid flow through the needle 12 at any time when the needle wings are bent, as they typically are during cannulation or insertion into the patient. Moving the wings into the bent upright position aligns a set of magnets 260 embedded in each wing such as to influence another magnet or magnet 262 within the needle body. This magnetic interaction induces the fluid flow valve to always remain in the flow on state as along as the magnets 260 and 262 are appropriately positioned. Bending the wings can deactivate the dislodgement detection mechanisms via interaction between the magnets. When the wings are then taped down for therapy, any skin sensing dislodgement mechanism 18 is then activated.

FIGS. 42A-42E illustrate that the device 10 can have a wetness detection system 270 (also referred to as a fluid detection system). FIGS. 42A-42E illustrate that the device 10 can have one or more expanders and/or fluid detectors. For example, FIGS. 42A-42E illustrate a device 10 designed to have an expander (e.g., a material, any material) which responds with a physical change in response to exposure to fluid serve as the actuating method. For example, FIGS. 42A-42E illustrate a wetness detection system 270. The wetness detection system 270 can have an expander 272. The expander 272 can be a fluid sensitive material, for example, a mass of fluid sensitive material. The expander 272 can be an occluder, for example, an expandable occluder. The wetness detection system 270 can have a fluid detector 274. The device 10 can have one or multiple expanders 272 (e.g., 1, 2, 3, or more expanders). The device 10 can have one or multiple fluid detectors 274 (e.g., 1, 2, 3, or more fluid detectors). The expander 272 can be configured to change shape (e.g., expand) upon contact with fluid. For example, the expander 272 can be configured to change shape upon contact with blood. The expander 272 (e.g., fluid sensitive material) can be an actuatable flow restrictor (e.g., an actuatable flow restrictor 28). The expander 272 can be an actuator configured to occlude blood flow through the device 10 by obstructing all or a portion of the device flow channel 62 upon contact with fluid. For example, in the design illustrated in FIGS. 42A-42E, an expander 272, such as a fluid sensitive material (e.g., hydrogel) is used as an actuator to close off the fluid flow from dislodgement when a liquid spill (such as blood) from dislodgement is detected based on swelling of the material. When the expander 272 contacts fluid, the expander 272 can swell/expand into the flow path (e.g., housing conduit 56) to occlude flow through the flow path. Additionally or alternatively, when the expander 272 contacts fluid, the expander 272 can swell/expand into a dislodgement mechanism actuator (i.e., an actuator that when engaged by the expander 272 activates the dislodgement mechanism to occlude flow through the flow path), or can swell/expand into a dislodgement mechanism and force it into an occluded position in the flow path.

FIGS. 42A-42E illustrate that the expander 272 can be in a cavity (e.g., in a small cavity) on the needle body (e.g., on housing 14 of the device 10). A first end of the cavity can be sealed and in contact with a fluid detector 274. A second end of the cavity can be open to the flow path in the device 10 or have a membrane across it. The membrane can be a breakable membrane. The membrane can be a deformable membrane. The membrane can be between the expander 272 and the flow path in the device 10. For example, the membrane can be at the bottom of the cavity (e.g., close to the flow path) such that a first side of the membrane faces or is in contact with the expander 272 and a second side of the membrane faces the flow path or defines at least a portion of the device channel 62. Expansion of the expander 272 (e.g., fluid sensitive material) upon contact with fluid (e.g., via a fluid detector 274 such as a capillary member) can apply force to the membrane to break the membrane and then expand into the flow path to occlude flow through the device 10. In such variations, the membrane can break without first deforming or break after first partially deforming into the flow path (e.g., by about 1 mm to about 3 mm). As another example, expansion of the expander 272 (e.g., fluid sensitive material) upon contact with fluid (e.g., via a fluid detector 274 such as a capillary member) can apply force to the membrane to deform the membrane into the flow path without breaking the membrane to occlude flow through the device 10 such that the expander 272 is contained within the expander cavity and a membrane cavity in the flow path after the expander 272 has expanded. In such variations, the membrane can fill up like a balloon into the flow path when the expander 272 is expanded. The ballooned portion or the membrane extension (e.g., the portion of the membrane in the flow path having the expanded expander 272) can function as a piston to occlude flow through the device 10 when the expander 272 is actuated. When the expander cavity is open to the flow path without a membrane, the cavity can be designed such that fluid that flows past the expander cavity does not flow into the cavity and contact the expander 272 when the device 10 is being used and the expander 272 has not yet been actuated. With and without a membrane, the expander 272 can occlude the flow path when expanded. Additionally or alternatively, the expander 272 can force an occluder into the flow path upon expanding after coming into contact with fluid. For example, an occluder (e.g., a piston, a rod) can be in the expander cavity. When the expander 272 (e.g., fluid sensitive material) expands, the expander 272 can force/push the occluder (e.g., the piston, the rod) into the flow path to occlude flow through the device 10. As another example, the occluder can be part of a dislodgement mechanism disclosed herein. As yet another example, the expander 272 can actuate a dislodgement mechanism disclosed herein to occlude the flow path upon expanding after coming into contact with fluid. When the expander 272 is a fluid sensitive material, the sealed top portion of the cavity can force the material to expand into the flow path when the expander 272 expands.

Figure 42D:
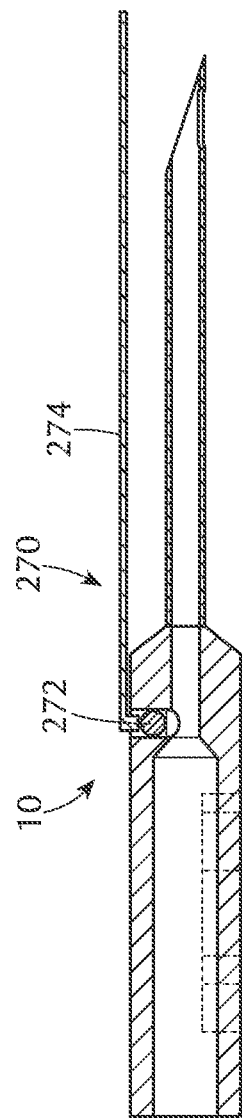
Figure 42E:
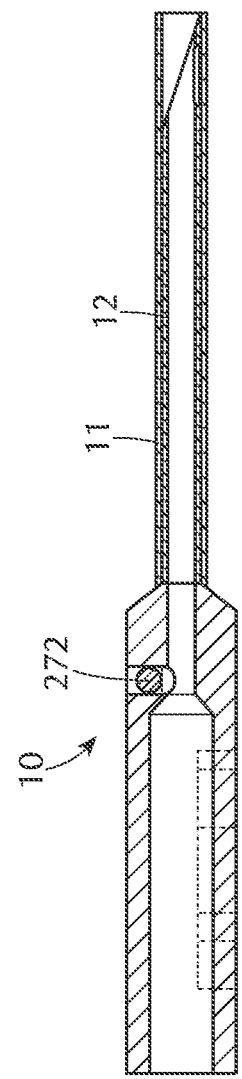

To insure that fluid loss from dislodgement of the needle is detected after insertion has occurred, a method to insure that fluid is detected by and/or communicated to the expander 272 (e.g., fluid sensitive material) embedded in the needle body is used. This can involve using a fluid detector 274. The fluid detector 274 can act as a conduit (e.g., as a mechanical conduit) from the needle tip back to the expander 272 (e.g., hydrogel or other material) that is serving as the flow stop actuator. The fluid detector 274 can be configured to be a capillary member that can wick fluid toward the expander 272. The fluid detector 274 can wick fluid to the expander 272. For example, the fluid detector 274 can wick fluid to the expander 272 in the expander cavity. The fluid detector 274 can be directly or indirectly connected to the expander 272. The fluid detector 274 can be contiguous with the expander 272. The fluid detector 274 can be an extension or a flap. The fluid detector 274 can be a sheath. The fluid detector 274 can be a retractable sheath. The fluid detector 274 can extend at least partially along an axis parallel to the device longitudinal axis A1 toward the tip of the need. The fluid detector 274 can extend past the tip of the needle. One example of a fluid detector 274 (e.g., a flap) is shown extending over the needle tip in FIGS. 42A-42D. This fluid detector 274 can use capillary action or other techniques to signal the presence of spilled fluid emanating from the dislodged needle tip down to the needle body. The expander 272 (e.g., hydrogel or other material) would then receive this wetness and then activate. Upon activation, the expander 272 can occlude the flow path, and/or can activate any of the flow restrictor mechanisms disclosed herein to block fluid flow through the device 10 with or without expanding into the flow path. When the expander 272 activates a flow restrictor mechanism when expanded, the expander 272 may or may not expand into the flow path. For example, when the expander 272 does not itself occlude the flow path when expanded, the expander 272 can actuate a separate occluder or flow restrictor (e.g., any of the occluder and flow restrictor mechanisms described herein). In addition to or in lieu of a flap as the fluid detector, a sheath or a retractable needle sheath 11 can be used as a conduit for delivering the presence of errant fluid to the needle body for actuation upon dislodgement. The sheath 11 can be a fluid detector 274. The sheath 11 can be exposed to the fluid flow at the needle bevel as shown in FIG. 42E. The sheath 11 can be contiguous with the fluid sensing expander 272 (e.g., fluid sensitive material). The fluid sensing material 272 (e.g., hydrogel) can be configured to expand into the flow path when exposed to fluid, and/or can expand to activate any of the flow restrictor mechanisms disclosed herein to block fluid flow through the device 10 with or without expanding into the flow path. The wick member 274 can be used to wick any fluid lost from the needle tip during therapy during dislodgement. The devices (e.g., devices 10) that have a fluid detection system 270 (e.g., an expander 272 and/or a fluid detector 274) can have a skin-sensing sensor 18. As another example, the devices (e.g., devices 10) that have a fluid detection system 270 (e.g., an expander 272 and/or a fluid detector 274) can have no skin-sensing sensor 18. For example, the sensors 18 in FIGS. 1-51E can be omitted from these devices 10.

FIGS. 43A-43D illustrate a needle with a mechanism 304 that detects both slip dislodgement and full off-the-body dislodgement and acts in either case to block fluid flow through the needle using mechanical compression of an internal tube 56. The mechanism 304 relies on tape or a high frictional force in place between the bottom skin sensing element and the skin itself. The physical act of sliding pulls a connecting arm to act on the compression piece 32 stopping flow during slip. The mechanism 304 can also be activated via the skin sensor during off-the-body dislodgement. The mechanism 304 is able to stop flow upon a change in horizontal or lateral position relative to the button/sensor 18 which is adhered to the skin with adhesive 310. The adhesion to the skin can be accomplished from various techniques, an example of a few are adhesive tape between the sensor 18 and the skin or magnets between the sensor 18 and magnetic tape on the skin.

Figure 43A:
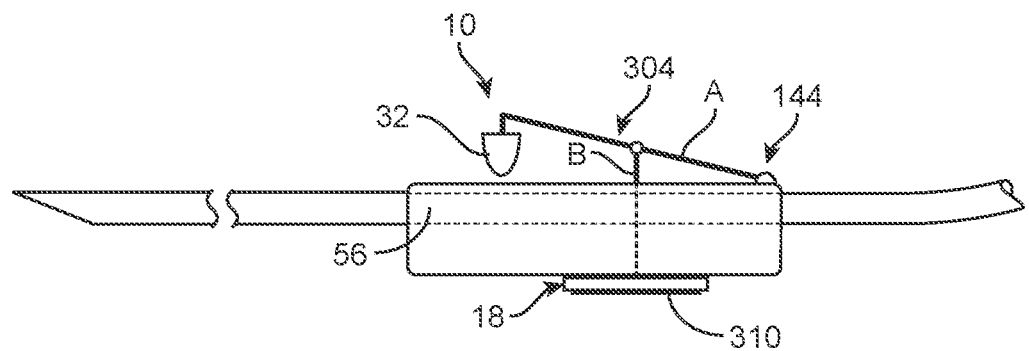
FIGS. 43A-43D illustrate a variation of a flow control system.
Figure 43B:
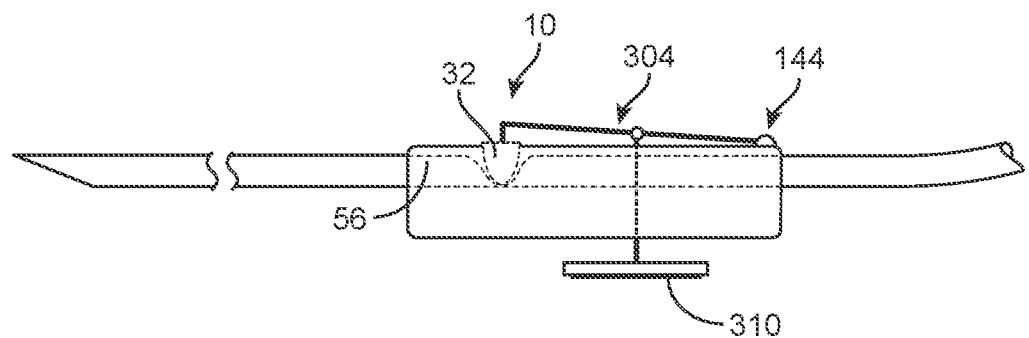
Figure 43C:
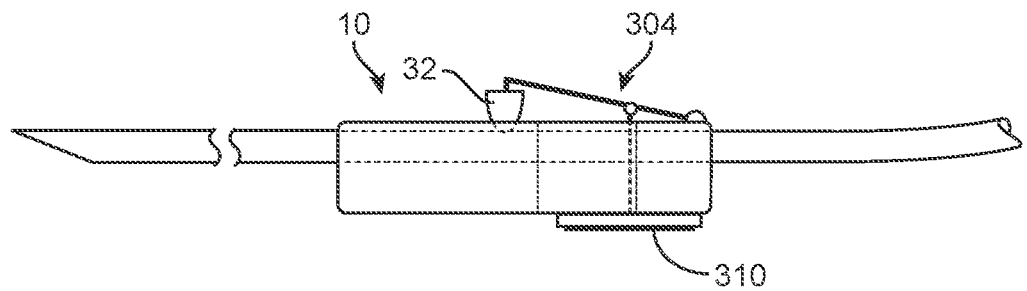
Figure 43D:
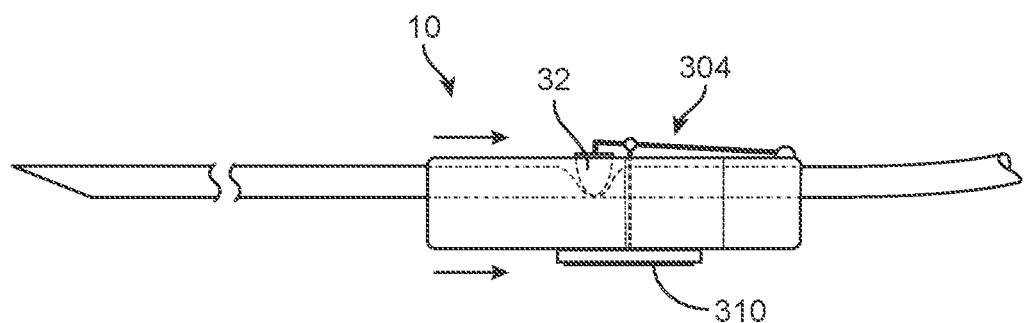

FIG. 43A illustrates the device 10 in a spring loaded state. In the spring loaded state, segment A is spring loaded. Segment A is in its natural state only when it is flat. When taped to the arm, segment A is bent up by a segment B and is under compression. FIG. 43B illustrates that when the device 10 falls off the arm, segment A moves into its natural state and closes the fluid path, allowing or pushing the occluder 32 into the flow path to block it. FIGS. 43C and 43D illustrate that when the needle butterfly is pulled in the opposite direction of the needle, the button/sensor 17 stays attached to the skin, and segment A moves relative to segment B via a sliding mechanism. Segment A moves into its natural state and closes the fluid path.

Figure 44A:
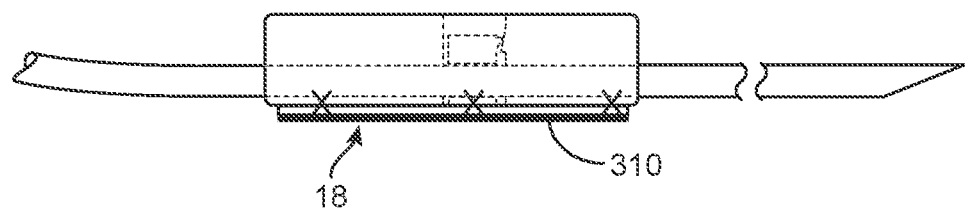
FIGS. 44A and 44B illustrate a variation of a flow control mechanism.
Figure 44B:
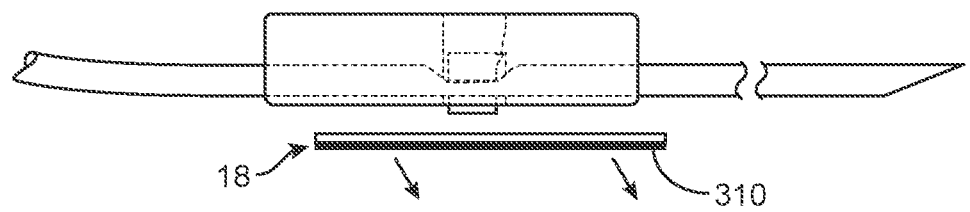

FIGS. 44A and 44B illustrate a needle system designed to stop both off-the-body and slip dislodgement within a combination mechanism built into a single needle. FIG. 44A shows a system that is able to stop flow upon a change in horizontal or lateral position relative to the button/sensor 18 which is adhered to the skin (e.g., using adhesive 310). The adhesion to the skin can be accomplished from various techniques, an example of a few are adhesive tape between the sensor and the skin or magnets between the sensor and magnetic tape on the skin. When the needle set is pulled off the arm or pulled in the horizontal direction (as shown by the two parallel arrows in FIG. 44B, the button/sensor 18 stays adhered to the skin and the device 10 breaks at the break points, represented as "X" on the drawing. Once the system breaks at the break point, a preloaded fluid path closing mechanism is triggered to shut off the fluid path.

Figure 45A:
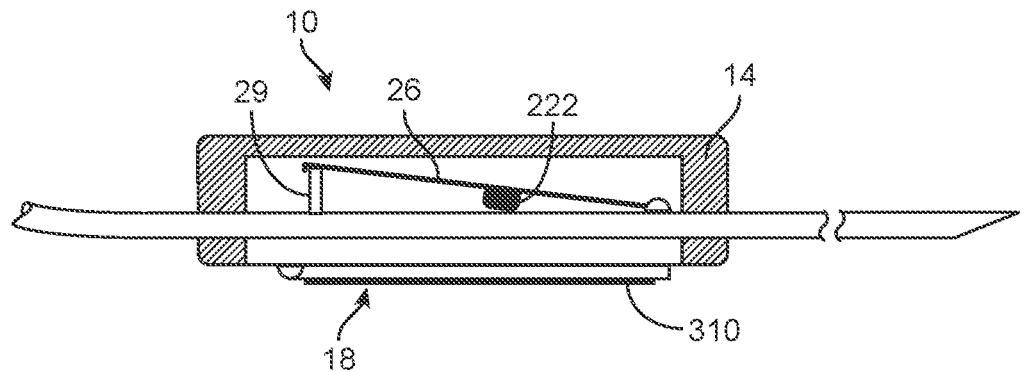
FIGS. 45A-45C illustrate a variation of a slip detector.
Figure 45B:
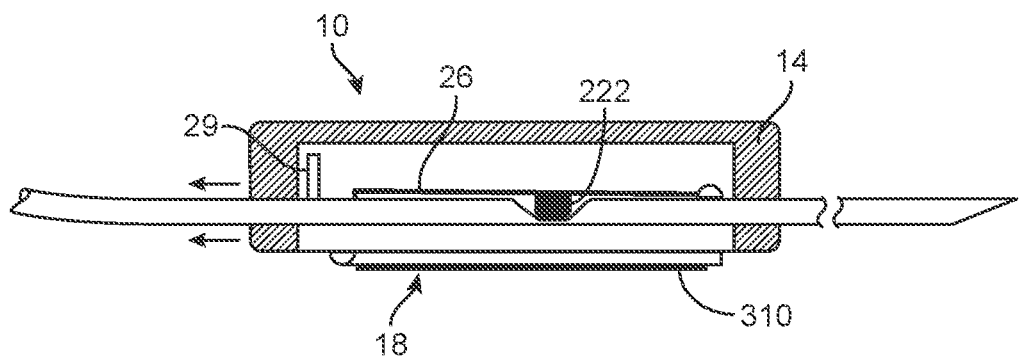
Figure 45C:
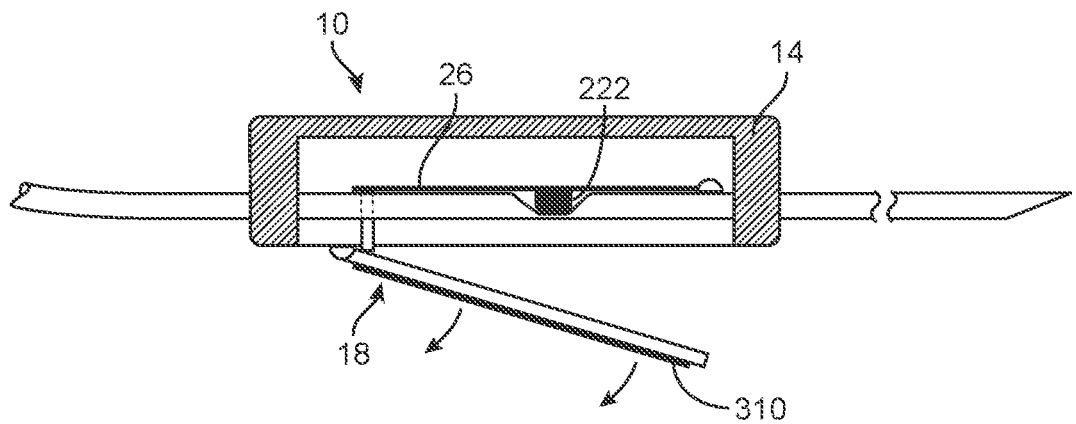

FIGS. 45A-45C illustrate a system that is able to stop flow upon a change in horizontal or lateral position relative to the hinge blade 18 which is adhered to the skin (e.g., using adhesive 310). The adhesion to the skin can be accomplished from various techniques, an example of a few are adhesive tape between the sensor and the skin or magnets between the sensor and magnetic tape on the skin.

FIG. 45A illustrates the device 10 in a spring loaded state. In the spring loaded state, a flat spring 26 is spring loaded. The flat spring 26 is in its natural state, for example, only when it is flat. The flat spring 26 does not need to be a flat spring. It can be non-flat. The flat surface of the spring 26 can be a flat rigid surface that is spring loaded. When taped to the arm, the flat spring 26 is bent up by a notch 29 and is under compression. FIG. 45B illustrates that when the needle butterfly is pulled in the opposite direction of the needle (as indicated by the two parallel arrows on the left side of FIG. 45B), the button/sensor 18 stays attached to the skin, and the rest of the needle segment moves a critical horizontal distance, in which the notch 29 disengages from the flat spring 26. The flat spring 26 moves into its natural state and closes the fluid path valve, which can take on many different types, for example a diaphragm (e.g., valve 222), ball, or pinch, valve, or any combination thereof. FIG. 45C illustrates that when the device 10 falls off the arm, the spring-loaded flat spring 26 moves into its natural position and closes the fluid path valve.

Figure 46A:
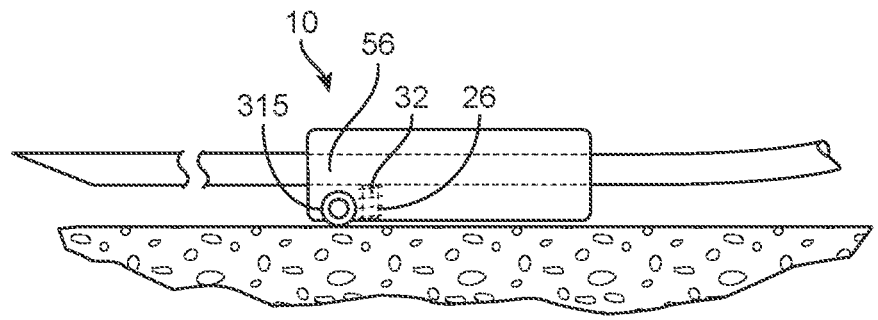
FIGS. 46A-46C illustrate a variation of a slip detector.
Figure 46B:
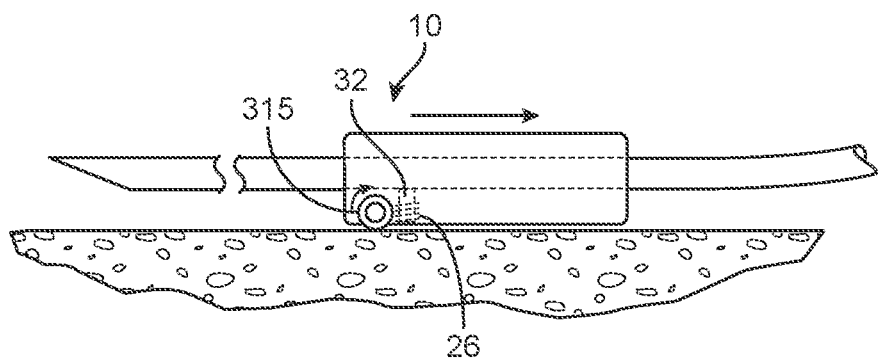
Figure 46C:
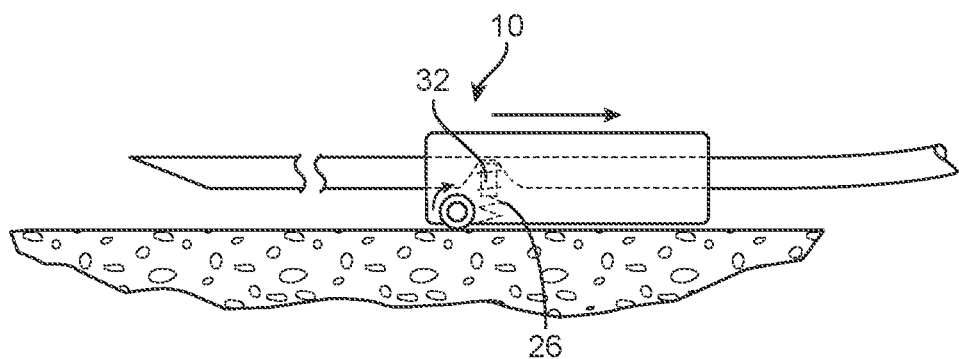

FIGS. 46A-46C illustrate a mechanism for detecting slip dislodgement. The mechanism for detecting slip dislodgement can be a roller wheel 315 which can measure the relative distance a needle body moved during slip. Movement of a threshold distance by the wheel 315 can trigger one of the flow stop mechanisms (also referred to as dislodgement mechanisms). FIG. 36B illustrates a slip below the threshold distance and FIG. 46C illustrates a slip satisfying the threshold distance such that the spring 26 forces the occluder 32 into the flow path.

Figure 47A:
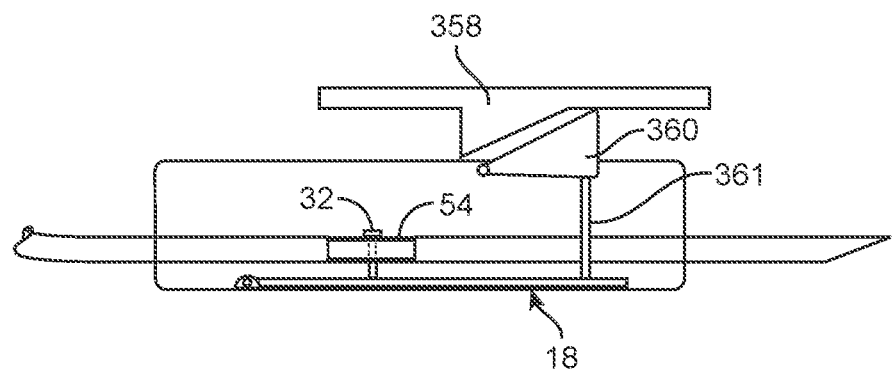
FIGS. 47A and 47B illustrate a variation of a slip detector.
Figure 47B:
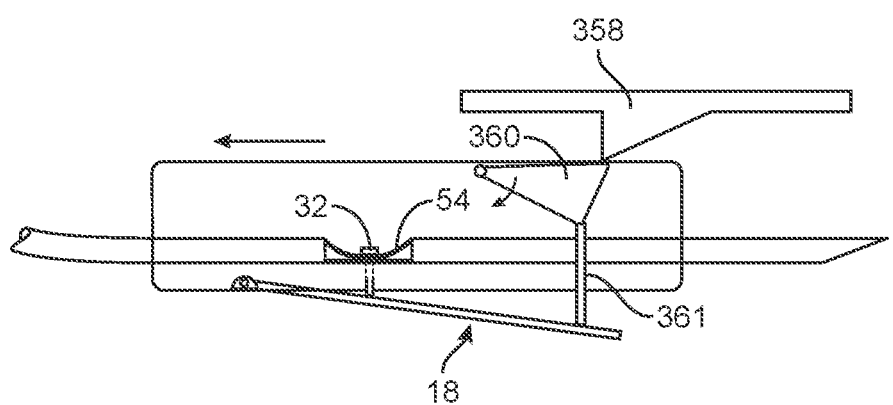

FIGS. 47A and 47B illustrate a sliding detection mechanism which is based on relative motion of the needle body against tape applied to a top member 358. Relative movement of the tape induces mechanical motion which is translated via the specific shape of the membrane into a mechanism which blocks flow through an internal tube.

Relative movement of the top member 358 can engage a hinged member 360 which can move the sensor 18 via an arm 361. FIG. 47B illustrates that downward movement (e.g., toward the bottom of the page) of the sensor 18 causes the occluder 32 to occlude the flow path. A linkage can connect the occluder 32 to the sensor 18.

Figure 48:
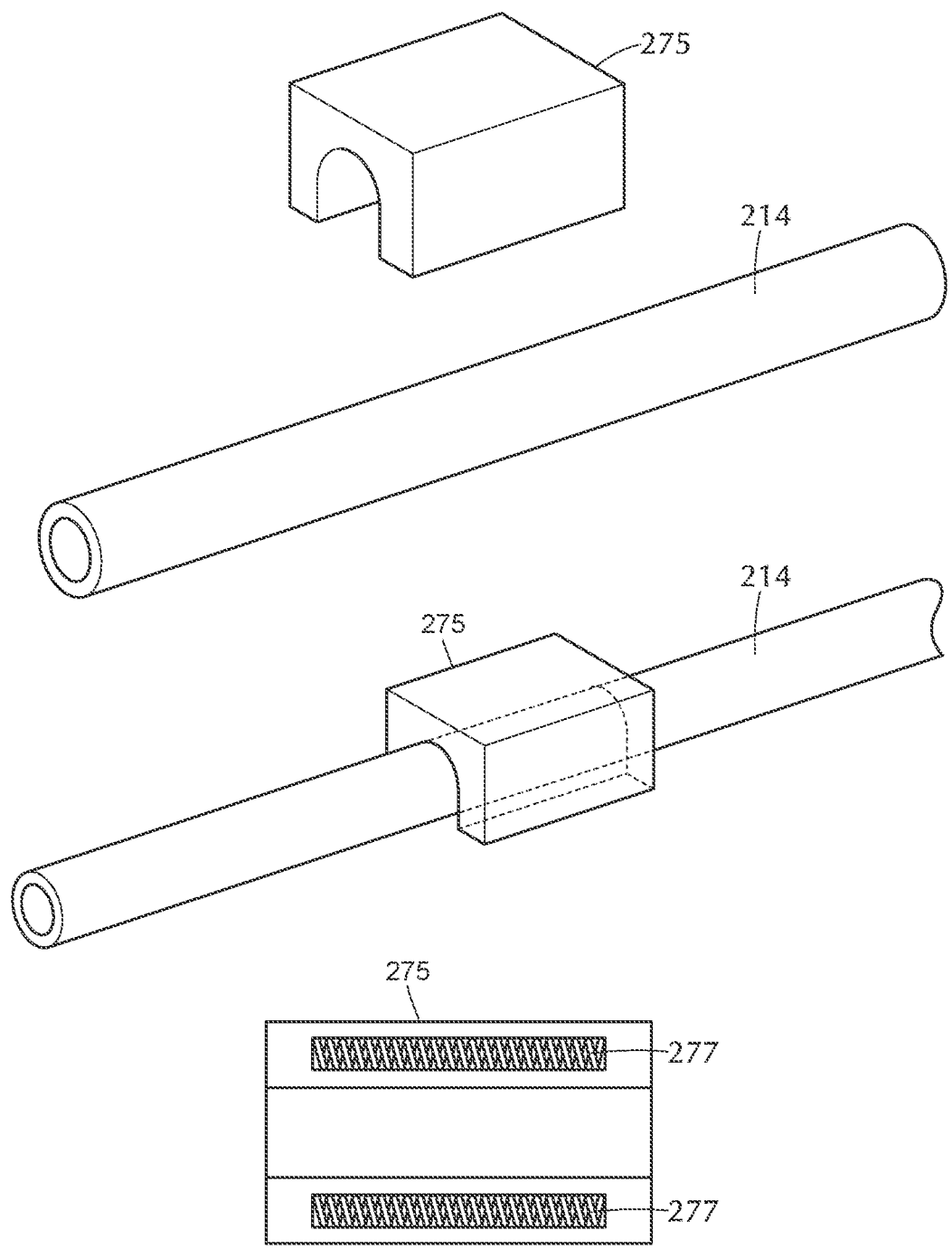
FIG. 48 illustrates a variation of an external flow control system.

FIG. 48 illustrates a variation of an add-on system. This is an external unit that contains dislodgement detection systems for either slip or full dislodgement or both. Such a unit is applied to the tubing (e.g., tubing 8) of a standard inserted AV fistula needle and snapped onto the tubing and taped in place. If the needle/tubing is dislodged in any way, the mechanisms detect dislodgement and immediately apply pressure to the tube, closing off flow. For example, the external unit can include a valve pinch housing 275. The valve pinch housing 275 can have spring-loaded contact points 277. The pinch valve 275 can operate when the contact points 277 come off the skin. The valve pinch housing can be pinched onto tube (e.g., tube 214) outside of the housing 14 of the device 10. The valve pinch housing 275 can snap onto the tube 214 behind the needle body.

Figure 49A:
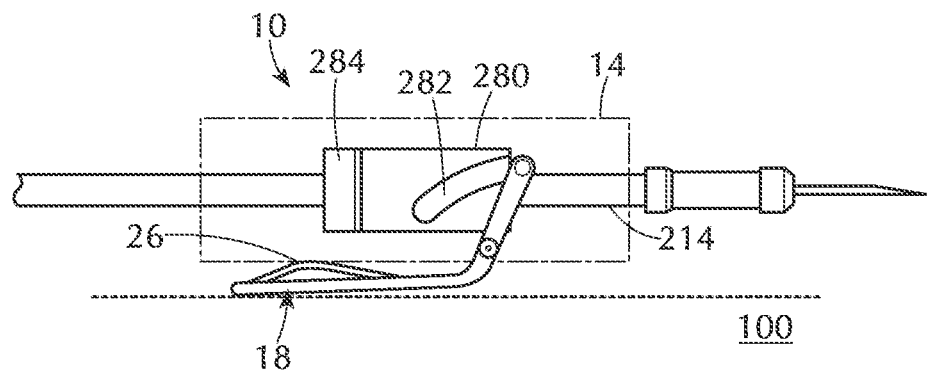
FIGS. 49A-49D illustrate a variation of a flow control system.
Figure 49B:
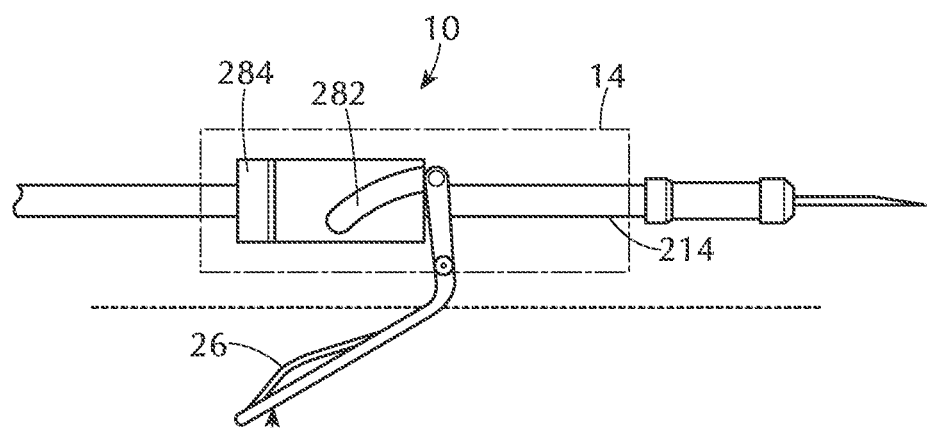
Figure 49C:
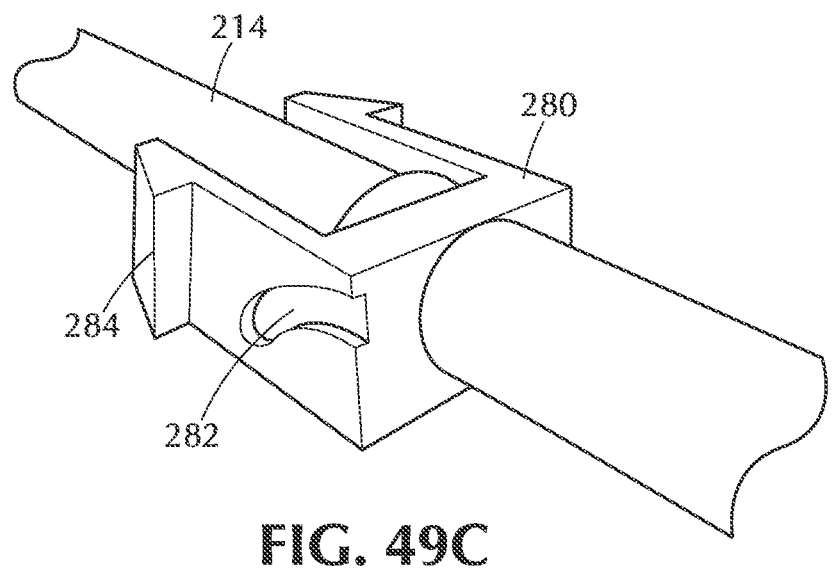
Figure 49D:
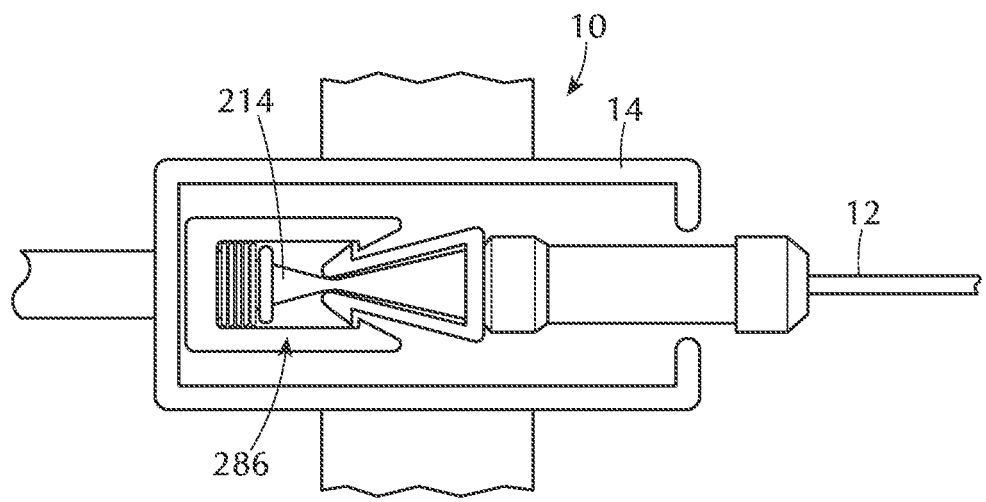

FIGS. 49A-49D illustrate a system 180 with both slip and full dislodgement detection and flow stop capabilities. A sliding shuttle 284 is attached to an articulating blade member 18 that acts as the skin sensing element. In the case of full dislodgement, the blade 18 opens and moves the shuttle 184 so that an internal compressible tube 214 is pinched closed via two cam wedges 284, blocking flow. A guide groove 282 in the side of the shuttle 284 may be used to refine the actuation process and result. The pinch mechanism 280 can also be activated if the needle body slips outward from its original insertion point a threshold distance. This slip motion could result for example from pull on the proximal end of the tubing, away from the needle insertion point. If this motion induces a threshold force higher than the spring holding the shuttle in place against the needle body, it can result in a closing motion of the cam wedges 284 that will pinch off the tube. Essential to this design is a change in the force applied via the slip motion. When the device slips, a certain force can be placed on the slide detection mechanism and the system is designed so that only above a certain force will the actuation for shut off be triggered. The device 10 can have a pinch lock system 286. FIG. 49D illustrates the tube 214 compressed by the cam wedges 284 and the cam wedges 284 locked into the pinch lock system 286.

Figure 50A:
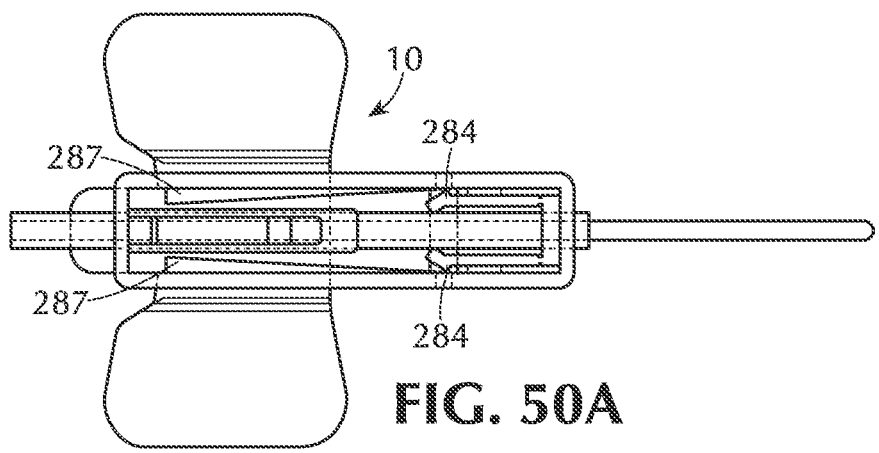
FIGS. 50A-50E illustrate a variation of a flow control system.
Figure 50B:
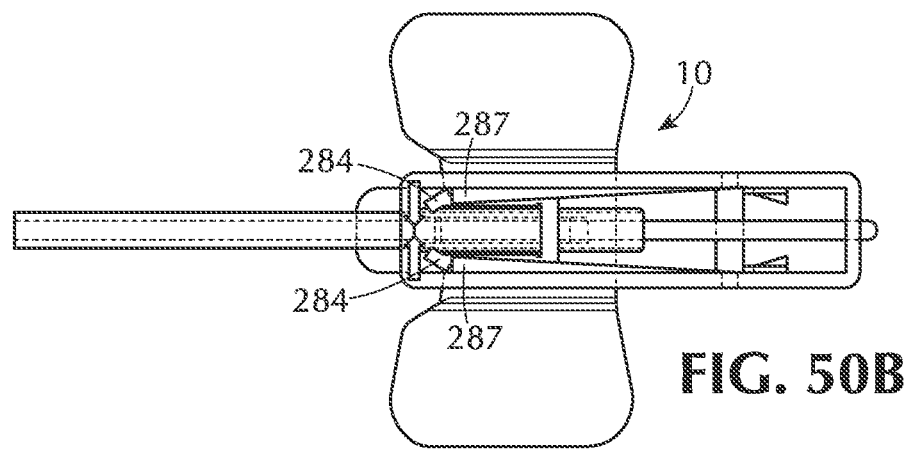
Figure 50C:
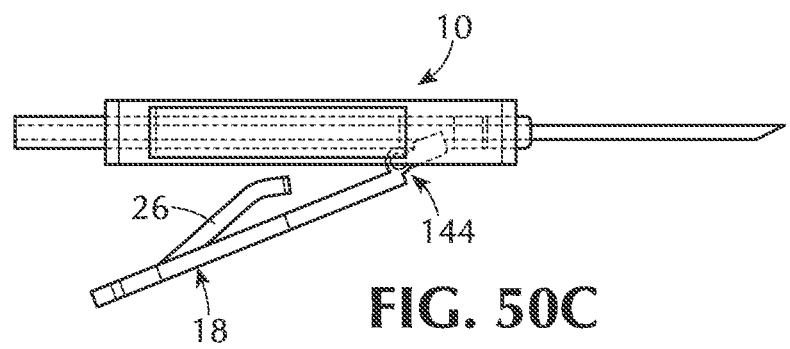
Figure 50D:
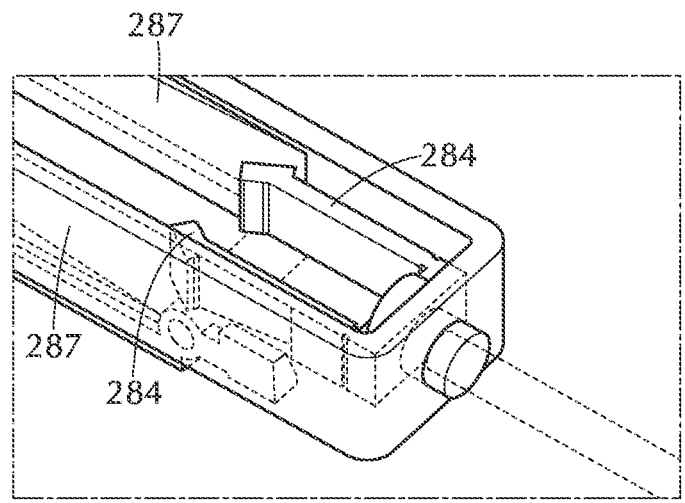
Figure 50E:
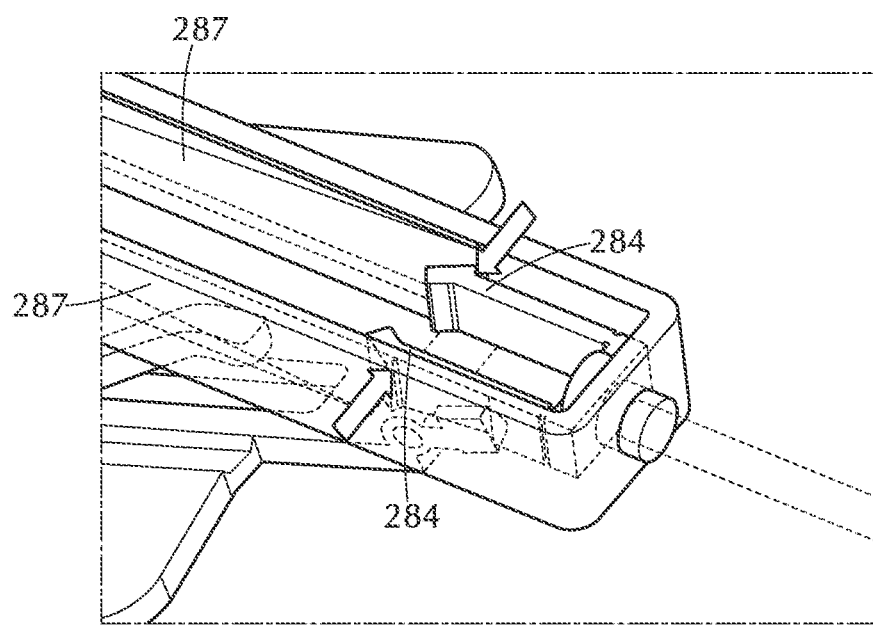
Figure 51A:
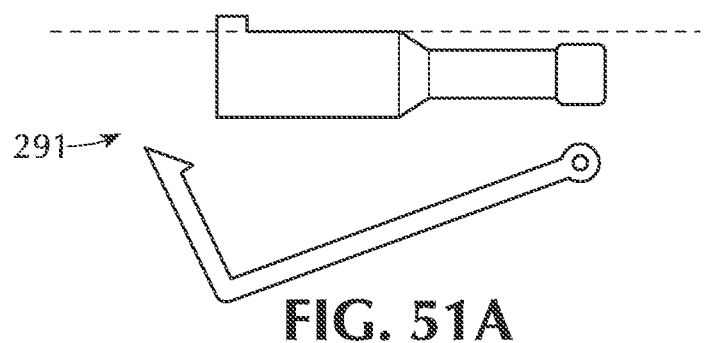
Figure 51B:
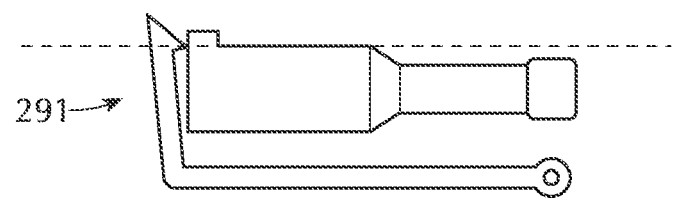
Figure 51C:
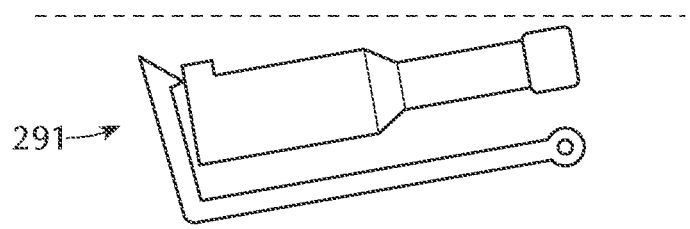

FIGS. 50A-50E illustrate another variation of the design shown in FIGS. 49A-49D. In this design, slip of a certain threshold distance is required to actuate the closing mechanism. In this type of arrangement, any pull of tubing above a threshold force limit will result in removal of the needle or needle housing from the vascular—but only a pull which also exceeds a certain distance will result in the closing mechanism being triggered. A cam wedge system is used to trigger closure and it can also be activated via articulation of a blade skin-sensing unit (e.g., sensor 18) in the case of full dislodgement. The cam wedges 284 can be forced inward toward the tube by wedges 287. FIG. 50A illustrates the cam wedges 284 in a neutral position and FIG. 50B illustrates the cam wedges 284 compressing the tube, as indicated by the two opposing arrows on the left side of FIG. 50B.

FIGS. 51A-51E illustrate a mechanism for creating a sliding detection system. In this variation a blade system 291 can activate a sliding shuttle or carriage 292 whose position is controlled by internal carriage bosses that direct the shuttle into a pinched position upon actuation due to slip or full dislodgement.

The devices 10 disclosed can be designed to very closely approximate a regular needle.

All the devices (e.g., devices 10) disclosed herein can have any combination of the features described herein. For example, all the devices (e.g., devices 10) disclosed herein can have a dislodgement sensor 18 and/or a pincher system 101. All the devices (e.g., devices 10) disclosed herein can have the external pincher subsystem and/or the internal pincher subsystem. For example, all the devices (e.g., devices 10) disclosed herein can have two or more external pinchers 104, one or more external pinch gaps 106, a movable shuttle 108, one or more internal pinchers 110, or any combination thereof. All the devices (e.g., devices 10) disclosed herein can have a cannulation control feature. All the devices (e.g., devices 10) disclosed herein can have a visual indicator. All the devices (e.g., devices 10) disclosed herein can have any of the sensors 18 (e.g., the sensor 18 can be a blade, blade member, button, button member, footplate, footplate member, and any of the other sensor skin-sensing mechanisms disclosed, or any combination thereof). For example, the sensor 18 described with reference to FIGS. 1-5 can be integrated with the device 10 described with reference to FIGS. 20A-21I, or vice versa. As another example, one or more features of the sensor 18 described with reference to FIGS. 1-5 can be incorporated with the device 10 described with reference to FIGS. 20A-21I, for example, the curved distal end 18b of the sensor 18 to ease insertion and/or act as a barrier to over insertion. All the devices (e.g., devices 10) disclosed herein can have any of the flow restrictors disclosed herein. All the devices (e.g., devices 10) disclosed herein can have any of the slip detectors disclosed herein. All the devices (e.g., devices 10 can have the wetness detection systems 270 disclosed herein. All the devices (e.g., devices 10) disclosed herein can have any combination of the features disclosed in FIGS. 1-22B. All the devices (e.g., devices 10) can have any combination of the features in FIGS. 23A-51E (e.g., the wetness detection system 270). All the devices (e.g., devices 10) can have any combination of the features in FIGS. 1-51E. For example, one or more features of the wetness detection system 270 can be incorporated with the device 10 described with reference to FIGS. 1-21I. None of the examples in this paragraph limit this disclosure. None of the examples in this paragraph exclude combinations of features not specifically provided in this paragraph as an example. In addition to all combinations of the features, devices, systems, and methods described herein (e.g., those illustrated in FIGS. 1-51E) being hereby explicitly disclosed, one of ordinary skill in the art will also readily appreciate how to integrate all of the features, devices, systems, and methods disclosed herein as their individual and collective disclosure is specifically taught herein.

Additional variations, features, elements and methods of use of needle safety systems (e.g., for automatic restriction or termination of flow due to needle dislodgement) are described in PCT Patent Application No. PCT/US2014/072573 filed Dec. 29, 2014, U.S. patent application Ser. No. 15/286,274 filed Oct. 5, 2016, and U.S. Provisional Application No. 61/978,671 filed Apr. 11, 2014, each of which is incorporated herein by reference in its entirety for all purposes, and can be combined with the present disclosure in any combination.

The variations disclosed herein are offered by way of example only. The claims are not limited to the variations shown in the drawings, but instead can claim any feature disclosed or contemplated in the disclosure as a whole. Any elements described herein as singular can be pluralized (i.e., anything described as "one" can be more than one). Any elements described herein as plural can be singularized (i.e., anything described as more than one can be "one."). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

We claim:

1. A tissue access device having a device longitudinal axis, the device comprising:
   a needle having a needle proximal end and a needle distal end;
   a housing having a housing opening and a housing conduit, wherein the housing conduit extends from a housing proximal end to a housing distal end;
   a deformable membrane, wherein the deformable membrane defines a portion of the housing conduit; and
   a movable footplate having a footplate proximal end, a footplate distal end, a footplate first surface, a spring, and an occluder, wherein the footplate is attached to the housing,
   wherein the movable footplate has a footplate first configuration when the footplate first surface applies a first force to a non-footplate surface and a footplate second configuration when the footplate first surface applies a second force less than the first force to the non-footplate surface,
   wherein the spring is biased to move the movable footplate from the footplate first configuration to the footplate second configuration when the first force decreases to the second force,
   wherein at least a first portion of the occluder occludes the housing conduit when the movable footplate is in the footplate second configuration, and
   wherein at least a second portion of the occluder is in the housing opening when the movable footplate is in the footplate second configuration and outside the housing opening when the movable footplate is in the footplate first configuration.

2. The device of claim 1, wherein the deformable membrane is less deformed by the occluder when the moveable footplate is in the footplate first configuration than when the moveable footplate is in the footplate second configuration.

3. The device of claim 1, wherein the footplate distal end is closer to the needle and the housing conduit when the moveable footplate is in the footplate first configuration than when the footplate is in the footplate second configuration, and wherein the spring is biased to move the footplate distal end away from the needle and the housing conduit when the movable footplate moves from the footplate first configuration to the footplate second configuration.

4. The device of claim 1, wherein the footplate distal end is configured to reduce friction against the non-footplate surface when the needle is inserted in a vessel.

5. The device of claim 1, wherein the footplate distal end has a curved surface configured to reduce friction against the non-footplate surface when the needle is inserted into a vessel.

6. The device of claim 1, wherein the footplate distal end comprises a barrier configured to prevent over insertion of the needle into a vessel.

7. The device of claim 6, wherein at least a portion of the barrier abuts or is next to a side of the needle when the moveable footplate is in the footplate first configuration.

8. The device of claim 6, wherein at least a portion of the barrier is closer to the needle when the moveable footplate is in the footplate first configuration than when the moveable footplate is in the footplate second configuration.

9. The device of claim 1, wherein the spring is integrated with the moveable footplate.

10. A tissue access device having a device longitudinal axis, the device comprising:
    a needle having a needle proximal end and a needle distal end;
    a housing having a housing opening and a housing conduit, wherein the housing conduit extends from a housing proximal end to a housing distal end;
    a deformable membrane, wherein the deformable membrane defines a portion of the housing conduit; and
    a movable footplate having a footplate proximal end, a footplate distal end, a footplate first surface, a spring, and an occluder, wherein the footplate is attached to the housing,
    wherein the spring is biased to move the moveable footplate from a footplate first configuration to a footplate second configuration when a force applied by the footplate first surface against a non-footplate surface changes from a first force to a second force less than the first force,
    wherein at least a first portion of the occluder occludes the housing conduit when the movable footplate is in the footplate second configuration,
    wherein at least a second portion of the occluder is in the housing opening when the movable footplate is in the footplate second configuration and outside the housing opening when the movable footplate is in the footplate first configuration, and
    wherein the footplate distal end comprises a barrier configured to prevent over insertion of the needle into a vessel, and wherein at least a portion of the barrier is closer to the needle when the moveable footplate is in the footplate first configuration than when the moveable footplate is in the footplate second configuration.

11. The device of claim 10, wherein the deformable membrane is less deformed by the occluder when the moveable footplate is in the footplate first configuration than when the moveable footplate is in the footplate second configuration.

12. The device of claim 10, wherein the footplate distal end is closer to the needle and the housing conduit when the moveable footplate is in the footplate first configuration than when the footplate is in the footplate second configuration, and wherein the spring is biased to move the footplate distal end away from the needle and the housing conduit when the movable footplate moves from the footplate first configuration to the footplate second configuration.

13. The device of claim 10, wherein the footplate distal end has a curved surface configured to reduce friction against the non-footplate surface when the needle is inserted into the vessel.

14. The device of claim 10, wherein the footplate distal end has a curved surface configured to reduce friction against the non-footplate surface when the needle is inserted into the vessel, and wherein at least a portion of the curved surface is closer to the needle when the moveable footplate is in the footplate first configuration than when the moveable footplate is in the footplate second configuration.

15. A vessel access device having a device longitudinal axis, the device comprising:
- a needle having a needle proximal end and a needle distal end;
- a housing having a housing opening and a housing conduit, wherein the housing conduit extends from a housing proximal end to a housing distal end;
- a deformable membrane, wherein the deformable membrane defines a portion of the housing conduit; and
- a movable footplate having a footplate proximal end, a footplate distal end, a footplate first surface, a spring, and an occluder, wherein the footplate is attached to the housing,
- wherein the spring is biased to move the moveable footplate from a footplate first configuration to a footplate second configuration when a force applied by the footplate first surface against a non-footplate surface changes from a first force to a second force less than the first force,
- wherein at least a first portion of the occluder occludes the housing conduit when the movable footplate is in the footplate second configuration,
- wherein at least a second portion of the occluder is in the housing opening when the movable footplate is in the footplate second configuration and outside the housing opening when the movable footplate is in the footplate first configuration, and
- wherein the footplate distal end has a curved surface configured to reduce friction against the non-footplate surface when the needle is inserted into a vessel, and wherein at least a portion of the curved surface is closer to the needle when the moveable footplate is in the footplate first configuration than when the moveable footplate is in the footplate second configuration.

16. The device of claim 15, wherein the deformable membrane is less deformed by the occluder when the moveable footplate is in the footplate first configuration than when the moveable footplate is in the footplate second configuration.

17. The device of claim 15, wherein the footplate distal end is closer to the needle and the housing conduit when the moveable footplate is in the footplate first configuration than when the footplate is in the footplate second configuration, and wherein the spring is biased to move the footplate distal end away from the needle and the housing conduit when the movable footplate moves from the footplate first configuration to the footplate second configuration.

* * * * *